(12) United States Patent
Summar et al.

(10) Patent No.: US 6,743,823 B1
(45) Date of Patent: Jun. 1, 2004

(54) THERAPEUTIC METHODS RELATING TO HUMAN CARBAMYL PHOSPHATE SYNTHETASE I POLYMORPHISM

(75) Inventors: Marshall L. Summar, Brentwood, TN (US); Brian W. Christman, Nashville, TN (US)

(73) Assignee: Vanderbilt University, Nashville, TN (US)

(*) Notice: Subject to any disclaimer, the term of this patent is extended or adjusted under 35 U.S.C. 154(b) by 99 days.

(21) Appl. No.: 09/585,077

(22) Filed: Jun. 1, 2000

Related U.S. Application Data

(63) Continuation-in-part of application No. 09/323,472, filed on Jun. 1, 1999, now Pat. No. 6,346,382.

(51) Int. Cl.⁷ .................. A61K 31/195; C07H 21/04; C12Q 1/68; C12N 9/12
(52) U.S. Cl. .................. 514/565; 536/23.2; 536/23.5; 435/6; 435/194
(58) Field of Search .................. 514/565; 536/23.2, 536/23.5; 435/6, 194

(56) References Cited

U.S. PATENT DOCUMENTS 5,217,997 A * 6/1993 Levere et al.

OTHER PUBLICATIONS

Mizutani et al. Oral Administration of Arginine and Citrulline in the Treatment of Lysinuric Protein Intolerance. J. Exp. Med. (1984), 142, pp. 15–24.*

Hoshide et al. Carbamyl Phosphate Synthetase I Deficiency. J. Clin. Invest. May 1993, 91(5), pp. 1884–1887.*

Finckh et al. Prenatal Diagnosis of Carbamoyl Phosphate Synthetase I Deficiency by Identification of a Missense Mutation in CPSI, Human Mutation. (1998), 12, pp. 206–211.*

Davies, et al. Idiopathic hyperammonemia: a frequently lethal complication of bone marrow transplantation. Bone Marrow Transplantation. (1996), 17, pp. 1119–1125.*

Vassa et al. Busulfan disposition and hepatic veno–occlusive disease in children undergoing bone marrow transplantation. Cancer Chemother Pharmacol. (1996), 37, pp. 247–253.*

Alonso et al., "Affinity Cleavage of Carbomoyl–Phosphate Synthetase I Localizes Regions of the Enzyme Interacting with the Molecule of ATP that Phosphyorylates Carbamate," Eur. J. Biochem , p. 377–384, (1995).

Guillou et al., "*Escherichia coli* Carbamoyl–Phosphate Synthetase: Domains of Glutaminase and Synthetase Subunit Interaction," Proc. Natl. Acad. Sci. USA, p. 8304–8308, (Nov. 14, 1989).

Guy et al., "Substructure of the Amidotransferase Domain of Mammalian Carbamyl Phosphate Synthetase," J. Biol. Chem, vol. 270 (No. 5), p. 2190–2197, (Feb. 3, 1995).

Lagace et al., "Rat Carbamyl–Phosphate Synthetase I Gene," J. Biol. Chem, vol. 262 (No. 22), p. 10415–10418, (Aug. 5, 1987).

Nyunoya et al., "Characterization and Derivation of the Gene Coding for Mitochondrial Carbamyl Phosphate Synthetase I of Rat," J. Biol. Chem., vol. 260 ( No. 16), p. 9346–9356, ( Aug. 5, 1985).

PCT International Search Report for International Application No. PCT/US00/15079, (date, p. Nos. NA).

Fearon et al., "Genetic Analysis of Carbamyl Phosphate Synthetase I Deficiency," *Human Genetics*, vol. 70, No. 3, pp. 207–210 (1985).

Finckh et al., "Prenatal Diagnosis of Carbamoyl Phosphate Synthetase I Deficiency by Identification of a Missense Mutation in CPS1," *Human Mutation*, Wiley–Liss, NY, vol. 12, No. 3, pp. 206–211 (1998).

Ghishan et al., "Polymerase Chain Reaction (PCR) Detectable Polymorphisms in the Prenatal Diagnosis of Carbamyl Phosphate Synthetase I Deficiency," *Gastroenterology*, vol. 106, No. 4 Suppl., p. A1028 (1994).

Haraguchi et al., "Cloning and Sequence of a CDNA Encoding Human Carbamyl Phosphate Synthetase I Molecular Analysis of Hyperammonemia," *Gene*, vol. 107, No. 2, pp. 335–340 (1991).

Vnencak–Jones et al., "Efficacy of Prenatal DNA Testing for Carbamyl Phosphate Synthetase I Deficiency," *Am. Jour. Human Genetics*, vol. 51, No. 4 Suppl., p. A357 (1992).

* cited by examiner

*Primary Examiner*—Carla J. Myers
*Assistant Examiner*—Diana Johannsen
(74) *Attorney, Agent, or Firm*—Jenkins, Wilson & Taylor, P.A.

(57) ABSTRACT

Isolated polynucleotide molecules and peptides encoded by these molecules are used in the analysis of human carbamyl phosphate synthetase I phenotypes, as well as in diagnostic and therapeutic applications, relating to a human carbamyl phosphate synthetase I polymorphism. By analyzing genomic DNA or amplified genomic DNA, or amplified cDNA derived from mRNA, it is possible to type a human carbamyl phosphate synthetase I with regard to the human carbamyl phosphate synthetase I polymorphism, for example, in the context of diagnosing and treating hepatic veno-occlusive disease (HVOD) associated with bone marrow transplants.

15 Claims, 12 Drawing Sheets

FIGURE 10

```
1
ctacttctca tgttcagcaa tttcttcttc tttatgtttt aaattacatg ttccataaaa ataagaaat
71
cactgtgata cggtaattga tttttcatt ttaaatgcag/(intron exon boundary)
111       (U4295)
CTGTTTGCCA CGGAAGCCAC ATCAGACTGG CTCAACGCCA ACAATGTCCC TGCCACCCCA GTGGCATGGC
181
CGTCTCAAGA AGGACAGAAT CCCAGCCTCT CTTCCATCAG AAA/ (intron exon boundary)
224                   GTCGGAGA GAAGGTAGTC TT    L(135a)
gtaagaacta ggcatactgt tttctgaaat aatttagagg attaactttg agaaccagta tatgaatatt
294
caccttgctt gattgcaagt cttttaaaac aaatttaaaa atgaatacat ttgtggatga ttgtcaagtt
364                                                    (L135b)
tcactctcca tcactatgga atacataacg tcatgtgtac atggtgatat gaaacgtgtt tcaaaatact
434
tcttagtaag gatactttcc ttgacggaaa caagtgagag tatgaagaat gtaatgcagc ac
```

| Primer | Begins | Size | SEQ ID NO: |
|---|---|---|---|
| U4295 | 119 | 20 | 8 |
| L135a | 220 | 21 | 9 |
| L135b | 370 | 24 | 10 |
| Spanner 1 | agctgtttgccacggaagcc | | 6 |
| Spanner 2 | cccagcctctcttccatcagaaagtaag | | 7 |

Pairs

U4295 - L135a   101 base fragment

U4295 - L135b   251 base fragment

Spanner1 - Spanner2   119 base fragment

FIGURE 11

CPSI T1405 SEQUENCE (SEQ ID NO:4)

```
MTRILTAFKV VRTLKTGFGF TNVTAHQKWK FSRPGIRLLS VKAQTAHIVL EDGTKMKGYS
FGHPSSVAGE VVFNTGLGGY PEAITDPAYK GQILTMANPI IGNGGAPDTT ALDELGLSKY
LESNGIKVSG LLVLDYSKDY NHWLATKSLG QWLQEEKVPA IYGVDTRMLT KIIRDKGTML
GKIEFEGQPV DFVDPNKQNL IAEVSTKDVK VYGKGNPTKV VAVDCGIKNN VIRLLVKRGA
EVHLVPWNHD FTKMEYDGIL IAGGPGNPAL AEPLIQNVRK ILESDRKEPL FGISTGNLIT
GLAAGAKTYK MSMANRGQNQ PVLNITNKQA FITAQNHGYA LDNTLPAGWK PLFVNVNDQT
NEGIMHESKP FFAVQFHPEV TPGPIDTEYL FDSFFSLIKK GKATTITSVL PKPALVASRV
EVSKVLILGS GGLSIGQAGE FDYSGSQAVK AMKEENVKTV LMNPNIASVQ TNEVGLKQAD
TVYFLPITPQ FVTEVIKAEQ PDGLILGMGG QTALNCGVEL FKRGVLKEYG VKVLGTSVES
IMATEDRQLF SDKLNEINEK IAPSFAVESI EDALKAADTI GYPVMIRSAY ALGGLGSGIC
PNRETLMDLS TKAFAMTNQI LVEKSVTGWK EIEYEVVRDA DDNCVTVCNM ENVDAMGVHT
GDSVVVAPAQ TLSNAEFQML RRTSINVVRH LGIVGECNIQ FALHPTSMEY CIIEVNARLS
RSSALASKAT GYPLAFIAAK IALGIPLPEI KNVVSGKTSA CFEPSLDYMV TKIPRWDLDR
FHGTSSRIGS SMKSVGEVMA IGRTFEESFQ KALRMCHPSI EGFTPRLPMN KEWPSNLDLR
KELSEPSSTR IYAIAKAIDD NMSLDEIEKL TYIDKWFLYK MRDILNMEKT LKGLNSESMT
EETLKRAKEI GFSDKQISKC LGLTEAQTRE LRLKKNIHPW VKQIDTLAAE YPSVTNYLYV
TYNGQEHDVN FDDHGMMVLG CGPYHIGSSV EFDWCAVSSI RTLRQLGKKT VVVNCNPETV
STDFDECDKL YFEELSLERI LDIYHQEACG GCIISVGGQI PNNLAVPLYK NGVKIMGTSP
LQIDRAEDRS IFSAVLDELK VAQAPWKAVN TLNEALEFAK SVDYPCLLRP SYVLSGSAMN
VVFSEDEMKK FLEEATRVSQ EHPVVLTKFV EGAREVEMDA VGKDGRVISH AISEHVEDAG
VHSGDATLML PTQTISQGAI EKVKDATRKI AKAFAISGPF NVQFLVKGND VLVIECNLRA
SRSFPFVSKT LGVDFIDVAT KVMIGENVDE KHLPTLDHPI IPADYVAIKA PMFSWPRLRD
ADPILRCEMA STGEVACFGE GIHTAFLKAM LSTGFKIPQK GILIGIQQSF RPRFLGVAEQ
LHNEGFKLFA TEATSDWLNA NNVPATPVAW PSQEGQNPSL SSIRKLIRDG SIDLVINLPN
NNTKFVHDNY VIRRTAVDSG IPLLTNFQVT KLFAEAVQKS RKVDSKSLFH YRQYSAGKAA
X
```

FIGURE 12

CPSI N1405 SEQUENCE (SEQ ID NO:2)

```
MTRILTAFKV VRTLKTGFGF TNVTAHQKWK FSRPGIRLLS VKAQTAHIVL EDGTKMKGYS
FGHPSSVAGE VVFNTGLGGY PEAITDPAYK GQILTMANPI IGNGGAPDTT ALDELGLSKY
LESNGIKVSG LLVLDYSKDY NHWLATKSLG QWLQEEKVPA IYGVDTRMLT KIIRDKGTML
GKIEFEGQPV DFVDPNKQNL IAEVSTKDVK VYGKGNPTKV VAVDCGIKNN VIRLLVKRGA
EVHLVPWNHD FTKMEYDGIL IAGGPGNPAL AEPLIQNVRK ILESDRKEPL FGISTGNLIT
GLAAGAKTYK MSMANRGQNQ PVLNITNKQA FITAQNHGYA LDNTLPAGWK PLFVNVNDQT
NEGIMHESKP FFAVQFHPEV TPGPIDTEYL FDSFFSLIKK GKATTITSVL PKPALVASRV
EVSKVLILGS GGLSIGQAGE FDYSGSQAVK AMKEENVKTV LMNPNIASVQ TNEVGLKQAD
TVYFLPITPQ FVTEVIKAEQ PDGLILGMGG QTALNCGVEL FKRGVLKEYG VKVLGTSVES
IMATEDRQLF SDKLNEINEK IAPSFAVESI EDALKAADTI GYPVMIRSAY ALGGLGSGIC
PNRETLMDLS TKAFAMTNQI LVEKSVTGWK EIEYEVVRDA DDNCVTVCNM ENVDAMGVHT
GDSVVVAPAQ TLSNAEFQML RRTSINVVRH LGIVGECNIQ FALHPTSMEY CIIEVNARLS
RSSALASKAT GYPLAFIAAK IALGIPLPEI KNVVSGKTSA CFEPSLDYMV TKIPRWDLDR
FHGTSSRIGS SMKSVGEVMA IGRTFEESFQ KALRMCHPSI EGFTPRLPMN KEWPSNLDLR
KELSEPSSTR IYAIAKAIDD NMSLDEIEKL TYIDKWFLYK MRDILNMEKT LKGLNSESMT
EETLKRAKEI GFSDKQISKC LGLTEAQTRE LRLKKNIHPW VKQIDTLAAE YPSVTNYLYV
TYNGQEHDVN FDDHGMMVLG CGPYHIGSSV EFDWCAVSSI RTLRQLGKKT VVVNCNPETV
STDFDECDKL YFEELSLERI LDIYHQEACG GCIISVGGQI PNNLAVPLYK NGVKIMGTSP
LQIDRAEDRS IFSAVLDELK VAQAPWKAVN TLNEALEFAK SVDYPCLLRP SYVLSGSAMN
VVFSEDEMKK FLEEATRVSQ EHPVVLTKFV EGAREVEMDA VGKDGRVISH AISEHVEDAG
VHSGDATLML PTQTISQGAI EKVKDATRKI AKAFAISGPF NVQFLVKGND VLVIECNLRA
SRSFPFVSKT LGVDFIDVAT KVMIGENVDE KHLPTLDHPI IPADYVAIKA PMFSWPRLRD
ADPILRCEMA STGEVACFGE GIHTAFLKAM LSTGFKIPQK GILIGIQQSF RPRFLGVAEQ
LHNEGFKLFA TEATSDWLNA NNVPANPVAW PSQEGQNPSL SSIRKLIRDG SIDLVINLPN
NNTKFVHDNY VIRRTAVDSG IPLLTNFQVT KLFAEAVQKS RKVDSKSLFH YRQYSAGKAA
X
```

THERAPEUTIC METHODS RELATING TO HUMAN CARBAMYL PHOSPHATE SYNTHETASE I POLYMORPHISM

RELATED APPLICATION INFORMATION

This is a continuation-in-part of U.S. patent application Ser. No. 9/323,472, filed Jun. 1, 1999, now U.S. Pat. No. 6,346,382, the entire contents of which are herein incorporated by reference.

GRANT STATEMENT

This work was supported by NIH grants R29-DK46965, NIH HL 55198, NIH ES 09915 and NIH 1 P30 CA 68485. Thus, the U.S. Government has certain rights in the invention.

TECHNICAL FIELD

The present invention relates to isolated polynucleotide molecules useful for analyzing carbamyl phosphate synthetase I phenotypes, to peptides encoded by these molecules, and to the diagnostic and therapeutic uses thereof relating to a newly identified carbamyl phosphate synthetase I polymorphism. Among such uses are methods for determining the susceptibility of a subject to hyperammonemia, decreased production of arginine and to bone marrow transplant toxicity based on an analysis of a sample isolated from tissue biopsies from the subject.

| Table of Abbreviations | |
|---|---|
| ABG | arterial blood gas(es) |
| ALI | acute lung injury |
| ASO | allele-specific oligonucleotide |
| ATP | adenosine triphosphate |
| BCAA | branched chain amino acid(s) |
| BMT | bone marrow transplant |
| BSA | bovine serum albumin |
| BuCy | busulfan, cyclophosphamide |
| BUN | blood urea nitrogen |
| CBVP16 | cyclophosphamide, bis-chloroethylnitrosourea, etoposide |
| cc | cubic centimeters |
| CPSI | carbamyl phosphate synthetase I |
| CTC | cyclophosphamide, thiotepa, carboplatin |
| CVP16TBI | cyclophosphamide, etoposide, total body irradiation |
| ECMO | extracorpreal membrane oxygenation |
| fl | full length |
| GSHosc | glutathione synthetase |
| HAT | hypoxanthine, aminopterin, thymidine |
| HVOD | hepatic veno-occlusive disease |
| iNO | inhaled nitric oxide |
| KDa | kilodalton |
| KLH | keyhole limpet hemocyanin |
| l | liter |
| LAT | ligation activated translation |
| LCR | ligase chain reaction |
| MAS | meconium aspiration syndrome |
| NAG | n-acetyl glutamate |
| NASDA ™ | nucleic acid sequence-based amplification |
| NO or $NO_x$ | nitric oxide |
| NOS | nitric oxide synthetase |
| O/C | omithine/citrulline |
| PBSCT | peripheral blood stem-cell transplantation |
| PPHN | persistant pulmonary hypertension in newborns |
| PCR | polymerase chain reaction |
| RCR | repair chain reaction |
| RDS | respiratory distress syndrome |
| REF | restriction endonuclease finger printing |
| RT | reverse transcriptase |
| SSCP | single strand conformation polymorphism |
| SDA | strand displacement activation |
| SNP | single nucleotide polymorphism |
| TC | thiotepa, cyclophosphamide |
| TEAA | total essential amino adds |
| UC | urea cycle |
| UCF | urea cycle function |
| VPA | valproic acid |

BACKGROUND ART

The in vivo synthetic pathway for arginine commences with ornithine. Omithine is combined with carbamyl phosphate to produce citrulline, which in turn is combined with aspartate, in the presence of adenosine triphosphate (ATP), to produce argininosuccinate. In the final step, fumarate is split from argininosuccinate, to produce arginine. The degradative pathway for arginine is by the hydrolytic action of arginase, to produce omithine and urea. These reactions form the urea cycle. The urea cycle serves as the primary pathway for removing waste nitrogen produced by the metabolism of endogenous and exogenous proteins, and is shown schematically in FIG. 1.

Disruption of metabolic processes is a frequent side effect of chemotherapy. Indeed, the agents used in high-dose chemotherapy affect a number of cellular processes. Metabolic processes localized in chemo-sensitive tissues, such as the liver and gastrointestinal tract, face a particularly great risk to disruption.

The constant turn-over and processing of nitrogen involves all the tissues in the body, but the first critical steps of the urea cycle are limited to the liver and gut. The high-dose chemotherapy associated with bone marrow transplant (BMT) interferes with liver function and is toxic to the intestine. Idiopathic hyperammonemia, which is suggestive of urea cycle dysfunction, has been reported to be associated with high mortality in patients undergoing bone marrow transplant. Davies et al., *Bone Marrow Transplantation*, 17:1119–1125 (1996); Tse et al., *American Journal of Hematology*, 38:140–141 (1991); and Mitchell et al., *American Journal of Medicine*, 85:662–667 (1988).

A common complication of BMT is hepatic veno-occlusive disease (HVOD). HVOD is associated with jaundice, increased liver size and disruption of normal hepatic blood flow. HVOD occurs in approximately 20 to 40% of patients and is associated with severe morbidity and mortality.

Nitric oxide (NO) plays a role in regulating vascular tone and in maintaining patency of hepatic and pulmonary venules following high-dose chemotherapy. Intact urea cycle function is important not only for excretion of ammonia but in maintaining adequate tissue levels of arginine, the precursor of NO.

Carbamyl phosphate synthetase I (CPSI) is the rate limiting enzyme catalyzing the first committed step of ureagenesis via the urea cycle. CPSI is highly tissue specific, with function and production substantially limited to liver and intestines. Genomically encoded, CPSI is produced in the cytoplasm and transported into the mitochondria where it is cleaved into its mature 160 kDA monomeric form. The enzyme combines ammonia and bicarbonate to form carbamyl with the expenditure of two ATP molecules and using the co-factor N-acetyl-glutamate (NAG).

Any genetic predisposition to decreased urea cycle function would lead to hyperammonemia and would likely contribute to the severity of disorders associated with suboptimal urea cycle function, including BMT-related toxicity. Thus, there is a need in the art for characterization of alleles present in populations suffering from disorders associated with suboptimal urea cycle function, undergoing BMT or otherwise facing exposure to environmental or pharmacological hepatotoxins. In view of the role of CPSI in the urea cycle, there is a particular need for characterization of CPSI alleles present in such populations.

SUMMARY OF THE INVENTION

A method of screening for susceptibility to sub-optimal urea cycle function in a subject is disclosed. The method comprising the steps of: (a) obtaining a nucleic acid sample from the subject; and (b) detecting a polymorphism of a carbamyl phosphate synthase I (CPSI) gene in the nucleic acid sample from the subject, the presence of the polymorphism indicating that the susceptibility of the subject to sub-optimal urea cycle function. In accordance with the present invention, detection of the polymorphism is particularly provided with respect to determining the susceptibility of a subject to bone marrow transplant toxicity.

Preferably, the polymorphism of the carbamyl phosphate synthetase polypeptide comprises a C to A transversion in exon 36 of the CPSI gene, more preferably at nucleotide 4340 of a cDNA that corresponds to the CPSI gene. More preferably, the C to A transversion at nucleotide 4340 of the cDNA that corresponds to the CPSI gene further comprises a change in the triplet code from AAC to ACC, which encodes a CPSI polypeptide having an threonine moiety at amino acid 1405.

The present invention also provides an isolated and purified biologically active CPSI polypeptide. Preferably, a polypeptide of the invention is a recombinant polypeptide. More preferably, a polypeptide of the present invention comprises human CPSI having an asparagine moiety at amino acid 1405.

The present invention also provides an isolated and purified polynucleotide that encodes a biologically active CPSI polypeptide. In a preferred embodiment, a polynucleotide of the present invention comprises a DNA molecule from a human. More preferably, a polynucleotide of the present invention comprises a cDNA that corresponds to the CPSI gene and which includes a C to A transversion at nucleotide 4340. Even more preferably, a polynucleotide of the present invention further comprises a cDNA that corresponds to the CPSI gene that includes a change in the triplet code from ACC to AAC at nucleotide 4340, and encodes a CPSI polypeptide having an asparagine moiety at amino acid 1405.

Kits and reagents, including oligonucleotides, nucleic acid probes and antibodies suitable for use in carrying out the methods of the present invention and for use in detecting the polypeptides and polynucleotides of the present invention are also disclosed herein. Methods for preparing the polynucleotides and polypeptides of the present invention are also disclosed herein.

In a further embodiment, this invention pertains to therapeutic methods based upon a polymorphism of a carbamyl phosphate synthase I (CPSI) gene as described herein. Such therapeutic methods include administration of nitric oxide precursors in the treatment and prophylaxis of disorders mediated or modulated by sub-optimal urea cycle function (e.g. bone marrow transplant toxicity) and gene therapy approaches using an isolated and purified polynucleotide of the present invention.

It is therefore an object of the present invention to provide polynucleotide molecules that can be used in analyzing carbamyl phosphate synthetase I (CPSI) in vertebrate subjects.

It is also an object of the present invention to provide for the determination of CPSI phenotype in vertebrate subjects and particularly human subjects, based on information obtained through the analysis of nucleic acids, including genomic DNA and cDNA, derived from tissues from the subject.

It is yet another object of the present invention to provide a ready technique for determining CPSI phenotype.

It is still a further object of the present invention to provide polypeptide and polynucleotide molecules for use in generating antibodies that distinguish between the different forms of CPSI which constitute the CPSI polymorphism.

It is yet a further object of the present invention is to provide methods for diagnosing and treating clinical syndromes related to and associated with the CPSI polymorphism.

Some of the objects of the invention having been stated hereinabove, other objects will become evident as the description proceeds, when taken in connection with the accompanying drawings and examples as best described hereinbelow.

BRIEF DESCRIPTION OF THE DRAWINGS

FIG. 10 is a diagram of exon 36 (SEQ ID NO:5) showing the locations of preferred oligonucleotide primers of the present invention;

FIG. 11 presents the amino acid sequence of T1405 CPSI (SEQ ID NO:4) (stop codon translated as "X", 165049 MW, 1.163602e+07 CN), with the initial amino acid methionine considered to be at a −1 position; and FIG. 12 presents the amino acid sequence of N1405 CPSI (SEQ ID NO:2) (stop codon translated as "X", 165062 MW, 1.161634E+07 CN), with the initial amino acid methionine considered to be at a −1 position.

DETAILED DESCRIPTION OF THE INVENTION

Disclosed herein is the surprising discovery of a polymorphism of carbamyl phosphate synthetase I (CPSI), the enzyme that catalyzes the rate limiting first step of the urea cycle. Particularly, the polymorphism is characterized by an amino acid substitution, threonine/asparagine at amino acid 1405 (heterozygosity=0.44) in CPSI.

Also disclosed herein is the surprising observation that a single nucleotide change in the CPSI gene is responsible for the polymorphism of CPSI. Particularly, a C to A transversion with exon 36 of the CPSI gene changes the triplet code from ACC to AAC and leads to the T1405N change in the encoded CPSI polypeptide.

In light of these discoveries, manipulation of nucleic acid molecules derived from the tissues of vertebrate subjects can be effected to provide for the analysis of CPSI phenotypes, for the generation of peptides encoded by such nucleic acid molecules, and for diagnostic and therapeutic methods relating to the CPSI polymorphism. Nucleic acid molecules utilized in these contexts may be amplified, as described below, and generally include RNA, genomic DNA and cDNA derived from RNA.

A. General Considerations

Most of the currently available structural information on CPSI is derived from studies of the rat CPSI enzyme. The rat CPSI enzyme and the human CPSI enzyme each comprise a single polypeptide of 1,500 residues and exhibit about 95% sequence identity. Rat CPSI polypeptide and nucleic acid sequence information is disclosed by Nyunoya, H., et al., *Journal of Biological Chemistry* 260:9346–9356 (1985) and at GenBank accession numbers AH005315, M12335, M12328, M12327, M12326, M12325, M12324, M12323, M12322, M12321, M12320, M12319, M12318 and M11710, herein incorporated by reference. The structural information about rat CPSI is derived from sequence homology and substrate and co-factor binding studies; however, no crystallographic data is available.

Mature CPSI is modular in nature, containing 2 main regions. The first region, residues 39–406, is homologous to the small subunit of the heterodimeric CPS of *Escherichia coli*. Bacterial and yeast CPSI polypeptide and nucleic acid sequence information is disclosed at GenBank accession numbers AB005063, X67573, M27174, P07258, P03965, BAA21088, SYBYCP, SYBYCS, and SYECCS, herein incorporated by reference.

Figure 2:
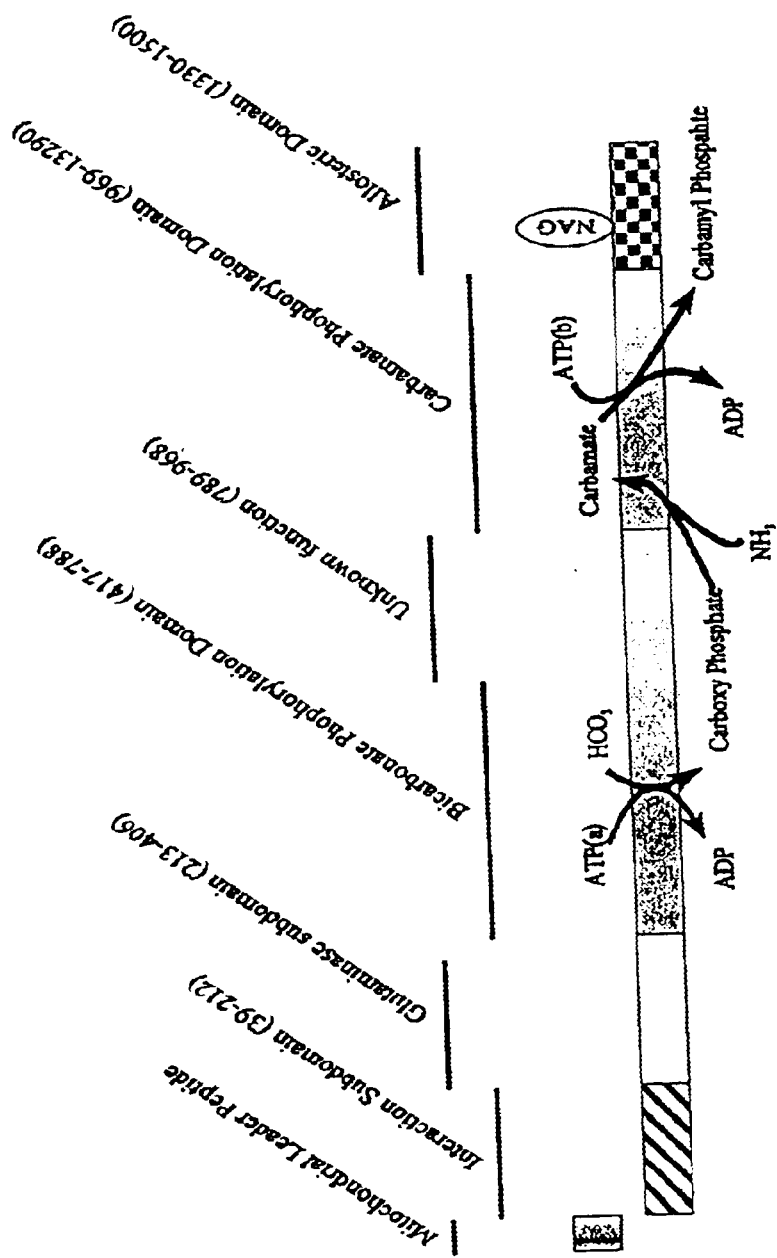
FIG. 2 is a schematic of the consensus CPSI protein which does not reflect recognized mutations.

The other region, residues 417–1500 (referred to herein after as the "CPS domain"), is homologous to the large subunit of *E. coli* CPS. Meister, A., *Adv. Enzymol. Relat. Areas Mol. Biol.* 62:315–374 (1989). This subunit is responsible for carbamyl phosphate synthesis from ammonia and for the binding of the substrates and cofactors. Meister, A., *Adv. Enzymol. Relat. Areas Mol. Biol.* 62:315–374 (1989). The CPS domain arose by gene duplication and tandem fusion in the pro-genome, and, as depicted schematically in FIG. 2, is itself composed of two phosphorylation domains and a C-terminal regulatory domain involved in the binding of n-acetyl-glutamate (NAG). Nyunoya, H., et al., *Journal of Biological Chemistry* 260:9346–9356 (1985).

As depicted schematically in FIG. 2, residues 407–416 act as a bridge between the the two major subunits, and residues 1–38 constitute the leader peptide that directs immature CPSI to the mitochondria prior to being removed. Continuing with FIG. 2, the small subunit-like region is composed of two approximately equal subdomains. The interaction subdomain, residues 39–212, corresponds to the region which, in the small subunit of the CPS from *E. coli*, is necessary for association with the large subunit. The glutaminase subdomain, residues 213–406, is homologous to several glutamine amidotransferases and to the region of CPSI that when generated free from other components exhibited considerable glutaminase activity, as described by Guillou, F., et al. *Proc Natl Acad Sci* 86:8304–8308 (1989); Nyunoya, H., et al., *Journal of Biological Chemistry* 260:9346–9356 (1985); and Guy, H. I. et al., *Journal of Biological Chemistry* 270:2190–2197 (1995). Since CPSI has lost the cysteine residue necessary to split glutamine, the function of the glutaminase subdomain is uncertain in this enzyme.

The CPS domain (corresponding to the large subunit in *E. coli*) is believed to catalyze the synthesis of carbamyl phosphate from ammonia, according to the reaction:

| 2 ATP + bicarbonate + ammonia | → | 2 ADP + phosphate + carbamyl phosphate |

Figure 1:
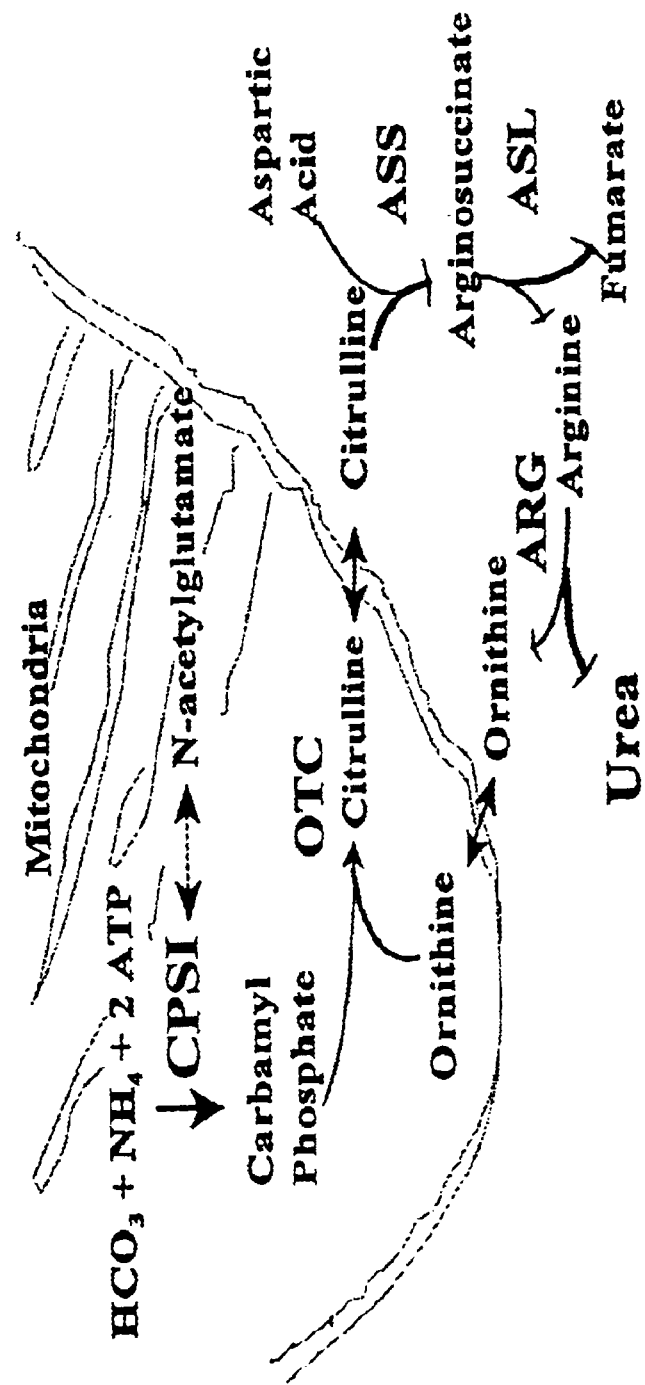
FIG. 1 is a schematic of the urea cycle.

As shown schematically in FIGS. 1 and 2, this reaction comprises three steps: bicarbonate phosphorylation by an ATP molecule that is designated herein as $ATP_A$, giving carboxyphosphate; carbamate synthesis from carboxyphosphate and ammonia; and carbamate phosphorylation by another ATP molecule ($ATP_B$), giving carbamyl phosphate, as described by Rubio, V. and Grisolia, S., *Enzyme* 26:233–239 (1981).

Figure 4:
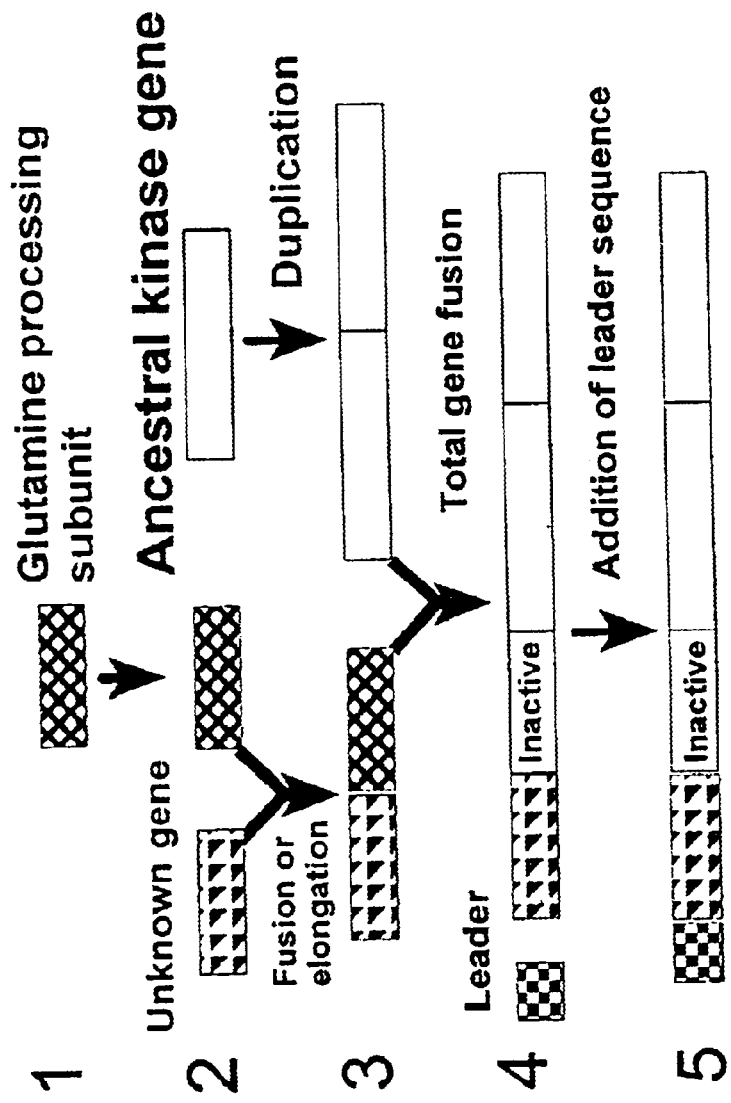
FIG. 4 is a schematic of recognized post-transcriptional modification of CPSI.

As shown schematically in FIG. 4, the CPS domain appears to have arisen by duplication and tandem fusion of the duplicated component; therefore, its amino and COOH-terminal halves are homologous, as described by Nyunoya, H., et al., *Journal of Biological Chemistry* 260:9346–9356 (1985)). Each homologous half comprises an amino- and a COOH-terminal domain of about 40 and 20 kDa, respectively, of which the domain of 40 kDa of the amino-half is believed to be involved in bicarbonate phosphorylation (bicarbonate phosphorylation domain, residues 417–788) (FIG. 2). The corresponding domain in the COOH-half is involved in carbamate phosphorylation via the carbamate phosphorylation domain, residues 969–1329 (FIG. 2), as described by Alonso, E. and Rubio, V., *European Journal of Biochemistry* 229:377–384 (1995)).

These phosphorylation domains are homologous to biotin carboxylase (Toh, H. et al., *European Journal of Biochemistry* 215:687–696 (1993)), an enzyme of known tri-dimensional structure that phosphorylates bicarbonate as well as DD-ligase and glutathione synthetase (GSHase), two enzymes that catalyze analogous reactions (Artymiuk, P. J. et al., *Nature Struct. Biol.* 3:128–132 (1996)). Thus, information on these enzymes is helpful in interpreting the mutations found in homologous domains in the patients with CPSI deficiency.

Referring again to FIG. 2, of the 20-kDa domains of the large subunit-like region, the function of the domain of the amino-terminal half, residues 789–968, remains to be established. In contrast, the corresponding COOH-terminal domain, residues 1330–1500, is called the allosteric domain, because the activator, n-acetyl-glutamate (NAG) of CPSI and the nucleotide effectors of the *E. coli* enzyme, UMP and IMP, bind in this domain, as described by Rodriguez-Aparicio, L. B. et al., *Biochemistry* 28:3070–3074 (1989) and Cervera, J. et al., *Biochemistry* 35:7247–7255 (1996).

A.1. Enzyme Processing.

Human CPSI mRNA encodes a 165 kDA, 1500 amino acid pre-protein. The amino terminus of this precursor contains 38 residues, including 8 basic residues, and 1 acidic residue with a Pro-Gly sequence 4 residues before the start of the mature enzyme (Nyunoya, H. et al., *Journal of Biological Chemistry* 260:9346–9356 (1985); Lagace, M. et al., *Journal of Biological Chemistry* 262:10415–10418 (1987). This highly conserved signal sequence promotes enzyme entry into the mitochondrial matrix, where it is then removed to produce the 160 kDA mature enzyme.

A2. Normal Expression of CPSI.

CPSI enzymatic activity is first detected in human fetal liver by 5–10 weeks gestation (Moorman, A. F. et al. *Histochemical Journal* 22:457–468 (1990)). By 20 weeks gestation, the level of CPSI reaches approximately 50% of the normal adult level, where it remains until birth, after which it gradually increases to adult levels by 20 years of age (Raiha, N. C. R. and Suihkonen, *J. Acta Paediatrica Scand* 57:121–127 (1968)). Tissue expression of CPSI is essentially limited to the liver, with trace amounts of activity in the intestine and kidney. When the liver develops its mature acinar structure in adulthood, CPSI is compartmentalized in parenchymal cells around the terminal portal venules (Moorman, A. F. et al. *Histochemical Journal* 22:457–468 (1990)).

In addition to its compartmentalization, several factors are known to be important in the regulation of CPSI activity and expression. For example, low or absent levels of omithine decrease CPSI activity, presumably due to an inhibitory effect from accumulated carbamyl phosphate (CP) as described by Jackson, M. J. et al., *Annual Review of Genetics* 20:431–464 (1986); and Rubio, V., *Biochemical Society Transactions* 21:198–202 (1993)). Levels of both CPSI mRNA and enzyme increase with a high protein diet, and in response to glucagon and glucocorticoids (Jackson, M. J. et al., *Annual Review of Genetics* 20:431–464 (1986); de Groot, C. J., et al., *Biochemical & Biophysical Research Communications* 124:882–888 (1984)). In normal unstimulated hepatic tissue that has been examined, an abundance of CPSI mRNA has been observed.

B. Screening Techniques

In accordance with the present invention, a method of screening for susceptibility to suboptimal urea cycle function resulting in decreased ammonia clearance and decreased arginine production in a subject is provided. The method comprises: (a) obtaining a nucleic acid sample from the subject; and (b) detecting a polymorphism of a carbamyl phosphate synthase I (CPSI) gene in the nucleic acid sample from the subject, the presence of the polymorphism indicating that the susceptibility of the subject to sub-optimal urea cycle function resulting in decreased ammonia clearance and decreased arginine production. In accordance with the present invention, detection of the polymorphism is particularly provided with respect to determining the susceptibility of a subject to bone marrow transplant toxicity.

It is further noted that the polymorphism of the present invention may be used to predict toxicity in a number of conditions beyond BMT or valproic acid administration as disclosed herein and in the Examples. The polymorphism is also implicated in the mediation or modulation of disrupted ammonia clearance and arginine production in situations such as adult hepatic cirrhosis, other medication toxicities, newborns with impaired hepatic function, and the like.

As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair.

Useful nucleic acid molecules according to the present invention include those which will specifically hybridize to CPSI sequences in the region of the C to A transversion at base 4340 and within exon 36 changing the triplet code from ACC to AAC. This transversion leads to the T1405N change in the encoded CPSI polypeptide. Typically these are at least about 20 nucleotides in length and have the nucleotide sequence corresponding to the region of the C to A transversion at base 4340 of the consensus CPSI cDNA sequence (EC6.3.4.16), which changes the triplet code from ACC to AAC. The term "consensus sequence", as used herein, is meant to refer to a nucleic acid or protein sequence for CSPI, the nucleic or amino acids of which are known to occur with high frequency in a population of individuals who carry the gene which codes for a normally functioning protein, or which nucleic acid itself has normal function.

Provided nucleic acid molecules can be labeled according to any technique known in the art, such as with radiolabels, fluorescent labels, enzymatic labels, sequence tags, etc. According to another aspect of the invention, the nucleic acid molecules contain the C to A transversion at base 4340. Such molecules can be used as allele-specific oligonucleotide probes to track a particular mutation, for example, through a family of subjects.

Body samples can be tested to determine whether the CPSI gene contains the C to A transversion at base 4340. Suitable body samples for testing include those comprising DNA, RNA or protein obtained from biopsies, including liver and intestinal tissue biopsies; or from blood, prenatal; or embryonic tissues, for example.

In one embodiment of the invention a pair of isolated oligonucleotide primers are provided: 5'-AGCTGTTTGCCACGGAAGCC-3'SEQ ID NO:6) and 5'-CCCAGCCTCTCTTCCATCAGAAAGTAAG-3'SEQ ID NO:7). These primers are derived from CPSI exon 36 (the location of the polymorphism of the present invention) and related intronic sequences (SEQ ID NO:5) and produce a 119 base pair fragment. Other primers derived from CPSI exon 36 (the location of the polymorphism of the present invention) and related intronic sequences (SEQ ID NO:5) are provided in SEQ ID NOs:8–10, in FIG. 10, and in Example 2 (SEQ ID NOs:15 and 16).

The oligonucleotide primers are useful in diagnosis of a subject at risk for hyperammonemia such as can result as a BMT complication or toxicity. The primers direct amplification of a target polynucleotide prior to sequencing. These unique CPSI exon 36 oligonucleotide primers were designed and produced based upon identification of the C to A transversion in exon 36.

In another embodiment of the invention isolated allele specific oligonucleotides are provided. Sequences substantially similar thereto are also provided in accordance with the present invention. The allele specific oligonucleotides are useful in diagnosis of a subject at risk for hyperammonemia, such as can result as a BMT complication or toxicity. These unique CPSI exon 36 oligonucleotide primers were designed and produced based upon identification of the C to A transversion in exon 36.

The terms "substantially complementary to" or "substantially the sequence of" refer to sequences which hybridize to the sequences provided (e.g. SEQ ID NOs: 5–10) under stringent conditions and/or sequences having sufficient homology with any of SEQ ID NOs: 5–10, such that the allele specific oligonucleotides of the invention hybridize to the sequence. The term "isolated" as used herein includes oligonucleotides substantially free of other nucleic acids, proteins, lipids, carbohydrates or other materials with which they may be associated, such association being either in cellular material or in a synthesis medium. A "target polynucleotide" or "target nucleic acid" refers to the nucleic acid sequence of interest e.g., a CPSI-encoding polynucleotide. Other primers which can be used for primer hybridization are readily ascertainable to those of skill in the art based upon the disclosure herein of the CPSI polymorphism.

Figure 5:
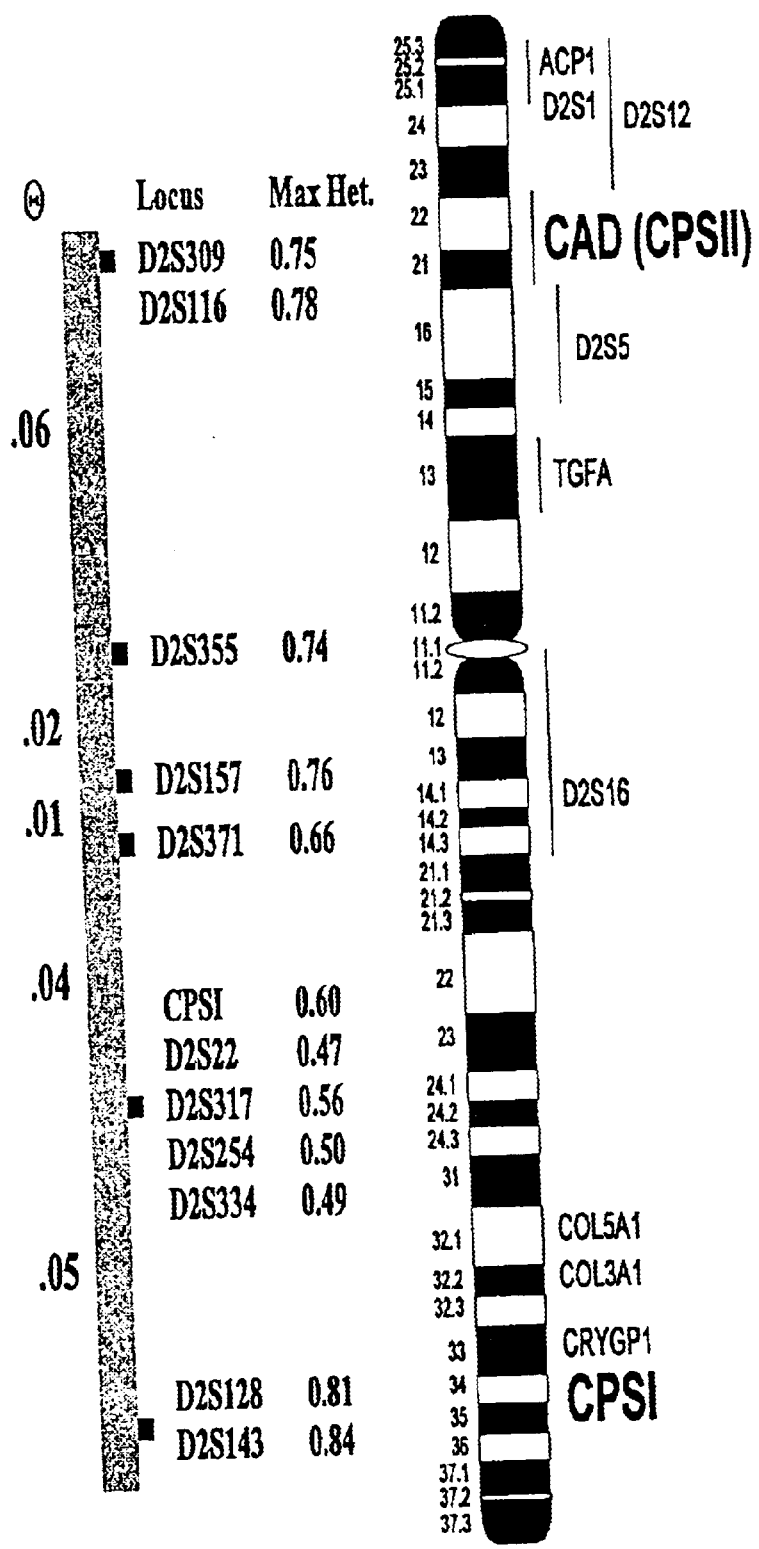
FIG. 5 is a schematic of the human genomic locus for CPSI.

The primers of the invention embrace oligonucleotides of sufficient length and appropriate sequence so as to provide initiation of polymerization on a significant number of nucleic acids in the polymorphic locus. The CPSI locus is depicted schematically in FIG. 5. Specifically, the term "primer" as used herein refers to a sequence comprising two or more deoxyribonucleotides or ribonucleotides, preferably more than three, and more preferably more than eight and most preferably at least about 20 nucleotides of the CPSI gene wherein the DNA sequence contains the C to A transversion at base 4340 relative to CPSI contained in SEQ ID NO's:1 and 3. The allele including cytosine (C) at base 4340 relative to CPSI is referred to herein as the "CPSIa allele", the "T1405 allele", or the "threonine-encoding allele". The allele including adenosine (A) at base 4340 relative to CPSI is referred to herein as the "CPSIb allele", the "N1405 allele", or the "arginine-encoding allele".

An oligonucleotide that distinguishes between the CPSIa and the CPSIb alleles of the CPSI gene, wherein said oligonucleotide hybridizes to a portion of said CPSI gene that includes nucleotide 4340 of the cDNA that corresponds to said CPSI gene when said nucleotide 4340 is adenosine, but does not hybridize with said portion of said CPSI gene when said nucleotide 4340 is cytosine is also provided in accordance with the present invention. An oligonucleotide that distinguishes between the CPSIa and the CPSIb alleles of the CPSI gene, wherein said oligonucleotide hybridizes to a portion of said CPSI gene that includes nucleotide 4340 of the cDNA that corresponds to said CPSI gene when said nucleotide 4340 is cytosine, but does not hybridize with said portion of said CPSI gene when said nucleotide 4340 is adenosine is also provided in accordance with the present invention. Such oligonucleotides are preferably between ten and thirty bases in length. Such oligonucleotides may optionally further comprises a detectable label.

Environmental conditions conducive to synthesis include the presence of nucleoside triphosphates and an agent for polymerization, such as DNA polymerase, and a suitable temperature and pH. The primer is preferably single stranded for maximum efficiency in amplification, but may be double stranded. If double stranded, the primer is first treated to separate its strands before being used to prepare extension products. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementary with the 5' and 3' sequences flanking the transversion to hybridize therewith and permit amplification of the genomic locus.

Oligonucleotide primers of the invention are employed in the amplification method which is an enzymatic chain reaction that produces exponential quantities of polymorphic locus relative to the number of reaction steps involved. Typically, one primer is complementary to the negative (−) strand of the polymorphic locus and the other is complementary to the positive (+) strand. Annealing the primers to denatured nucleic acid followed by extension with an enzyme, such as the large fragment of DNA polymerase I (Klenow) and nucleotides, results in newly synthesized + and − strands containing the target polymorphic locus sequence. Because these newly synthesized sequences are also templates, repeated cycles of denaturing, primer annealing, and extension results in exponential production of the region (i.e., the target polymorphic locus sequence) defined by the primers. The product of the chain reaction is a discreet nucleic acid duplex with termini corresponding to the ends of the specific primers employed.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage et al., *Tetrahedron Letters* 22:1859–1862 (1981). One method for synthesizing oligonucleotides on a modified solid support is described in U.S. Pat. No. 4,458,066.

Any nucleic acid specimen, in purified or non-purified form, can be utilized as the starting nucleic acid or acids, providing it contains, or is suspected of containing, a nucleic acid sequence containing the polymorphic locus. Thus, the method may amplify, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material, preferably liver tissue, and the like by a variety of techniques such as that described by Maniatis et. al. in *Molecular Cloning: A Laboratory Manual*, Cold Spring Harbor, N.Y., p 280–281 (1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

The deoxyribonucleotide triphosphates dATP, dCTP, dGTP, and dTTP are added to the synthesis mixture, either separately or together with the primers, in adequate amounts and the resulting solution is heated to about 90–100° C. from about 1 to 10 minutes, preferably from 1 to 4 minutes. After this heating period, the solution is allowed to cool, which is preferable for the primer hybridization. To the cooled mixture is added an appropriate agent for effecting the primer extension reaction (called herein "agent for polymerization"), and the reaction is allowed to occur under conditions known in the art. The agent for polymerization may also be added together with the other reagents if it is heat stable. This synthesis (or amplification) reaction may occur at room temperature up to a temperature above which the agent for polymerization no longer functions. Thus, for example, if DNA polymerase is used as the agent, the temperature is generally no greater than about 40° C. Most conveniently the reaction occurs at room temperature.

The agent for polymerization may be any compound or system which will function to accomplish the synthesis of primer extension products, including enzymes. Suitable enzymes for this purpose include, for example, $E.$ $coli$ DNA polymerase I, Klenow fragment of $E.$ $coli$ DNA polymerase, polymerase muteins, reverse transcriptase, other enzymes, including heat-stable enzymes (i.e., those enzymes which perform primer extension after being subjected to temperatures sufficiently elevated to cause denaturation), such as Taq polymerase. Suitable enzyme will facilitate combination of the nucleotides in the proper manner to form the primer extension products which are complementary to each polymorphic locus nucleic acid strand. Generally, the synthesis will be initiated at the 3' end of each primer and proceed in the 5' direction along the template strand, until synthesis terminates, producing molecules of different lengths.

The newly synthesized strand and its complementary nucleic acid strand will form a double-stranded molecule under hybridizing conditions described above and this hybrid is used in subsequent steps of the method. In the next step, the newly synthesized double-stranded molecule is subjected to denaturing conditions using any of the procedures described above to provide single-stranded molecules.

The steps of denaturing, annealing, and extension product synthesis can be repeated as often as needed to amplify the target polymorphic locus nucleic acid sequence to the extent necessary for detection. The amount of the specify nucleic acid sequence produced will accumulate in an exponential fashion. *PCR. A Practical Approach*, ILR Press, Eds. McPherson et al. (1992).

The amplification products may be detected by Southern blot analysis with or without using radioactive probes. In one such method, for example, a small sample of DNA containing a very low level of the nucleic acid sequence of the polymorphic locus is amplified, and analyzed via a Southern blotting technique or similarly, using dot blot analysis. The use of non-radioactive probes or labels is facilitated by the high level of the amplified signal. Alternatively, probes used to detect the amplified products can be directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the probe, or will be able to ascertain such, using routine experimentation.

Sequences amplified by the methods of the invention can be further evaluated, detected, cloned, sequenced, and the like, either in solution or after binding to a solid support, by any method usually applied to the detection of a specific DNA sequence such as dideoxy sequencing, PCR, oligomer restriction (Saiki et al., *Bio/Technology* 3:1008–1012 (1985), allele-specific oligonucleotide (ASO) probe analysis (Conner et al., *Proc. Natl. Acad. Sci. U.S.A.* 80:278 (1983), oligonucleotide ligation assays (OLAs) (Landgren et. al., *Science* 241:1007, 1988), and the like. Molecular techniques for DNA analysis have been reviewed (Landgren et. al., *Science* 242:229–237, 1988).

Preferably, the method of amplifying is by PCR, as described herein and in U.S. Pat. Nos. 4,683,195; 4,683,202; and 4,965,188 each of which is hereby incorporated by reference; and as is commonly used by those of ordinary skill in the art. Alternative methods of amplification have been described and can also be employed as long as the CPSI locus amplified by PCR using primers of the invention is similarly amplified by the alternative means. Such alternative amplification systems include but are not limited to self-sustained sequence replication, which begins with a short sequence of RNA of interest and a T7 promoter. Reverse transcriptase copies the RNA into cDNA and degrades the RNA, followed by reverse transcriptase polymerizing a second strand of DNA.

Another nucleic acid amplification technique is nucleic acid sequence-based amplification (NASBA™) which uses reverse transcription and T7 RNA polymerase and incorporates two primers to target its cycling scheme. NASBA™ amplification can begin with either DNA or RNA and finish with either, and amplifies to about $10^8$ copies within 60 to 90 minutes.

Alternatively, nucleic acid can be amplified by ligation activated transcription (LAT). LAT works from a single-stranded template with a single primer that is partially single-stranded and partially double-stranded. Amplification is initiated by ligating a cDNA to the promoter olignucleotide and within a few hours, amplification is about $10^8$ to about $10^9$ fold. The QB replicase system can be utilized by attaching an RNA sequence called MDV-1 to RNA complementary to a DNA sequence of interest. Upon mixing with a sample, the hybrid RNA finds its complement among the specimen's mRNAs and binds, activating the replicase to copy the tag-along sequence of interest.

Another nucleic acid amplification technique, ligase chain reaction (LCR), works by using two differently labeled halves of a sequence of interest which are covalently bonded by ligase in the presence of the contiguous sequence in a sample, forming a new target. The repair chain reaction (RCR) nucleic acid amplification technique uses two complementary and target-specific oligonucleotide probe pairs, thermostable polymerase and ligase, and DNA nucleotides to geometrically amplify targeted sequences. A 2-base gap separates the oligo probe pairs, and the RCR fills and joins the gap, mimicking normal DNA repair.

Nucleic acid amplification by strand displacement activation (SDA) utilizes a short primer containing a recognition site for HincII with short overhang on the 5' end which binds to target DNA. A DNA polymerase fills in the part of the primer opposite the overhang with sulfur-containing adenine analogs. HincII is added but only cuts the unmodified DNA strand. A DNA polymerase that lacks 5' exonuclease activity enters at the cite of the nick and begins to polymerize, displacing the initial primer strand downstream and building a new one which serves as more primer.

SDA produces greater than about a $10^7$-fold amplification in 2 hours at 37° C. Unlike PCR and LCR, SDA does not require instrumented temperature cycling. Another amplification system useful in the method of the invention is the QB Replicase System. Although PCR is the preferred method of amplification if the invention, these other methods can also be used to amplify the CPSI locus as described in the method of the invention. Thus, the term "amplification technique" as used herein and in the claims is meant to encompass all the foregoing methods.

In another embodiment of the invention a method is provided for diagnosing or identifying a subject having a predisposition or higher susceptibility to (at risk of) hyperammonemia, comprising sequencing a target nucleic acid of a sample from a subject by dideoxy sequencing, preferably following amplification of the target nucleic acid.

In another embodiment of the invention a method is provided for diagnosing a subject having a predisposition or higher susceptibility to (at risk of) hyperammonemia, comprising contacting a target nucleic acid of a sample from a subject with a reagent that detects the presence of the CPSI polymorphism and detecting the reagent.

Another method comprises contacting a target nucleic acid of a sample from a subject with a reagent that detects the presence of the C to A transversion at base 4340, i.e. within exon 36, and detecting the transversion. A number of hybridization methods are well known to those skilled in the art. Many of them are useful in carrying out the invention.

Hepatic veno-occlusive disease (HVOD) is a common toxicity in bone marrow transplant (BMT). It occurs in approximately 20 to 40% of patients and is associated with severe morbidity and mortality. In accordance with the present invention, the frequency of both CPSI alleles was tested in an HVOD and a non-HVOD group undergoing BMT in an effort to identify evidence of disequilibrium. The results indicated the CPSI polymorphism disclosed herein effects susceptibility to a BMT toxicity. Thus, a method of screening subjects for susceptibility to BMT toxicity, and particularly to HVOD, via detection of the CPSI polymorphism is provided in accordance with the present invention.

The materials for use in the method of the invention are ideally suited for the preparation of a diagnostic kit. Such a kit may comprise a carrier means being compartmentalized to receive in close confinement one or more container means such as vials, tubes, and the like, each of the container means comprising one of the separate elements to be used in the method. For example, one of the container means may comprise means for amplifying CPSI DNA, the means comprising the necessary enzyme(s) and oligonucleotide primers for amplifying said target DNA from the subject.

The oligonucleotide primers include primers having a sequence selected from the group including, but not limited to: SEQ ID NOs:6–10, or primer sequences substantially complementary or substantially homologous thereto. The target flanking 5' and 3' polynucleotide sequence has substantially the sequence set forth in SEQ ID NO:5, and sequences substantially complementary or homologous thereto. Other oligonucleotide primers for amplifying CPSI will be known or readily ascertainable to those of skill in the art given the disclosure of the present invention presented herein.

A kit in accordance with the present invention can further comprise a reagent or reagents for extracting a nucleic acid sample from a biological sample obtained from a subject. Any such reagents as would be readily apparent to one of ordinary skill in the art are contemplated to fall within the scope of the present invention. By way of particular example, a suitable lysis buffer for the tissue along with a suspension of glass beads for capturing the nucleic acid sample and an elution buffer for eluting the nucleic acid sample off of the glass beads comprise reagents for extracting a nucleic acid sample from a biological sample obtained from a subject.

Other examples include commercially available, such as the GENOMIC ISOLATION KIT A.S.A.P.™ (Boehringer Mannheim, Indianapolis, Ind.). Genomic DNA Isolation System (GIBCO BRL, Gaithersburg, Md.), ELU-QUIK™ DNA Purification Kit (Schleicher & Schuell, Keene, N. H.), DNA Extraction Kit (Stratagene, La Jolla, Calif.), TURBO-GEN™ Isolation Kit (Invitrogen, San Diego, Calif.), and the like. Use of these kits according to the manufacturers instructions is generally acceptable for purification of DNA prior to practicing the methods of the present invention.

C. Definitions Affecting CPSI-encoding Polynucleotide and CPSI Polypeptides Encoded by Same In accordance with the present invention, purified and isolated CPSI-encoding polynucleotides and CPSI polypeptides encoded by same are provided. A particularly provided CPSI-encoding polynucleotide comprises a CPSI encoding polynucleotide which includes a C to A transversion at base 4340, i.e. within exon 36, of the CPSI gene which changes the triplet code from ACC to AAC and leads to the T1405N change in the encoded CPSI polypeptide. The encoded CPSI polypeptide comprising the T1405N change is also particularly provided. Thus, allelic variant polynucleotides and polypeptides encoded by same are provided in accordance with the present invention. Further, a biologically active CPSI polypeptide is also provided in accordance with the present invention, as is a CPSI-encoding polynucleotide encoding such a CPSI polypeptide. Exemplary biological activities include the biological activity of mediating the first step of the urea cycle and the biological activity of cross-reacting with an anti-CPSI antibody.

The provided CPSI-encoding polynucleotides and polypeptides have broad utility given the biological significance of the urea cycle, as is known in the art. By way of example, the CPSI-encoding polynucleotides and polypeptides are useful in the preparation of screening assays and assay kits that are used to detect the presence of the proteins and nucleic acids of this invention in biological samples. Additionally, it is well known that isolated and purified polypeptides have utility as feed additives for livestock and polynucleotides encoding the polypeptides are thus useful in producing the polypeptides.

Preferably, the provided CPSI polynucleotides and polypeptides are isolated from vertebrate and invertebrate sources. Thus, homologs of CPSI, including, but not limited to, mammalian, yeast and bacterial homologs are provided in accordance with the present invention. Preferred mammalian homologs of CPSI members include, but are not limited to, rat and human homologs.

The terms "CPSI gene product", "CPSI protein" and "CPSI polypeptide" refer to proteins having amino acid sequences which are substantially identical to the native amino acid sequences in CPSI and which are biologically active in that they are capable of mediating the synthesis of carbamyl phosphate in the urea cycle, or cross-reacting with anti-CPSI antibodies raised against a CPSI polypeptide.

The terms "CPSI gene product", "CPSI protein" and "CPSI polypeptide" also include analogs of CPSI molecules which exhibit at least some biological activity in common with native CPSI gene products. Furthermore, those skilled in the art of mutagenesis will appreciate that other analogs, as yet undisclosed or undiscovered, may be used to construct CPSI analogs. There is no need for an "CPSI gene product", "CPSI protein" or "CPSI polypeptide" to comprise all, or substantially all of the amino acid sequence of a native CPSI gene product. Shorter or longer sequences are anticipated to be of use in the invention. Thus, the term "CPSI gene product" also includes fusion or recombinant CPSI polypeptides and proteins. Methods of preparing such proteins are described herein.

The terms "CPSI-encoding polynucleotide", "CPSI gene", "CPSI gene sequence" and "CPSI gene segment" refer to any DNA sequence that is substantially identical to a polynucleotide sequence encoding a CPSI gene product, CPSI protein or CPSI polypeptide as defined above. The terms also refer to RNA, or antisense sequences, compatible with such DNA sequences. "CPSI-encoding polynucleotide", "CPSI gene", "CPSI gene sequence" and "CPSI gene segment" may also comprise any combination of associated control sequences.

The term "substantially identical", when used to define either a CPSI gene product or CPSI amino acid sequence, or a CPSI gene or CPSI nucleic acid sequence, means that a particular sequence, for example, a mutant sequence, varies from the sequence of a natural CPSI by one or more deletions, substitutions, or additions, the net effect of which is to retain at least some of biological activity of CPSI. Alternatively, DNA analog sequences are "substantially identical" to specific DNA sequences disclosed herein if: (a) the DNA analog sequence is derived from coding regions of the natural CPSI gene; or (b) the DNA analog sequence is capable of hybridization of DNA sequences of (a) under moderately stringent conditions and which encode biologically active CPSI gene product; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

C.1. Percent Similarity

Percent similarity may be determined, for example, by comparing sequence information using the GAP computer program, available from the University of Wisconsin Geneticist Computer Group. The GAP program utilizes the alignment method of Needleman et al., *J. Mol. Biol.* 48:443 (1970), as revised by Smith et al., *Adv. Appl. Math.* 2:482 (1981). Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., *Nucl. Acids. Res.* 14:6745 (1986), as described by Schwartz et al., eds., *Atlas of Protein Sequence and Structure*, National Biomedical Research Foundation, pp. 357–358 (1979); (2) a penalty of 3.0 for each gap and an additional 0.01 penalty for each symbol and each gap; and (3) no penalty for end gaps. Other comparison techniques are described in the Examples.

The term "homology" describes a mathematically based comparison of sequence similarities which is used to identify genes or proteins with similar functions or motifs. Accordingly, the term "homology" is synonymous with the term "similarity" and "percent similarity as defined above. Thus, the phrases "substantial homology" or "substantial similarity" have similar meanings.

C.2. Nucleic Acid Sequences

In certain embodiments, the invention concerns the use of CPSI genes and gene products that include within their respective sequences a sequence which is essentially that of a CPSI gene, or the corresponding protein. The term "a sequence essentially as that of a CPSI gene", means that the sequence substantially corresponds to a portion of a CPSI polypeptide or CPSI encoding polynucleotide and has relatively few bases or amino acids (whether DNA or protein) which are not identical to those of a CPSI protein or CPSI gene, (or a biologically functional equivalent of, when referring to proteins). The term "biologically functional equivalent" is well understood in the art and is further defined In detail herein. Accordingly, sequences which have between about 70% and about 80%; or more preferably, between about 81% and about 90%; or even more preferably, between about 91% and about 99%; of amino acids which are identical or functionally equivalent to the amino acids of a CPSI protein or CPSI gene, will be sequences which are "essentially the same".

CPSI gene products and CPSI genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1).

TABLE 1

Table of the Genetic Code

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See e.g., Wetmur & Davidson, *J. Mol. Biol.* 31:349–370 (1968)).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species, Furthermore, a DNA segment encoding a CPSI polypeptide refers to a DNA segment which contains CPSI coding sequences, yet is isolated away from, or purified free from, total genomic DNA of a source species, such as Homo sapiens. Included within the term "DNA segment" are DNA segments and smaller fragments of such segments, and also recombinant vectors, including, for example, plasmids, cosmids, phages, viruses, and the like.

Similarly, a DNA segment comprising an isolated or purified CPSI gene refers to a DNA segment including CPSI coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the CPSI gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a CPSI polypeptide that includes within its amino acid sequence an amino acid sequence of any of SEQ ID NOs:2, 4, 12 and 14. In other particular embodiments, the invention concerns isolated DNA segments and recombinant vectors incorporating DNA sequences which encode a protein that includes within its amino acid sequence the amino acid sequence of a CPSI polypeptide corresponding to human tissues.

It will also be understood that this invention is not limited to the particular nucleic acid and amino acid sequences of SEQ ID NO's:1–4 and 11–14. Recombinant vectors and isolated DNA segments may therefore variously include the CPSI polypeptide-encoding region itself, include coding regions bearing selected alterations or modifications in the basic coding region, or include encoded larger polypeptides which nevertheless include CPSI polypeptide-encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of SEQ ID NOs:2, 4, 12 and 14. Naturally, where the DNA segment or vector encodes a full length CPSI gene product, the most preferred nucleic acid sequence is that which is essentially as set forth in any of SEQ ID NOs: 1, 3, 11 and 13 and which encode a protein that exhibits activity in the urea cycle, as may be determined by, for example, calorimetric assays to detect production of carbonyl phosphate from ammonia, as disclosed herein in Example 3.

The term "a sequence essentially as set forth in any of SEQ ID NO:2, 4, 12 and 14" means that the sequence substantially corresponds to a portion an amino acid sequence either of SEQ ID NOs:2, 4, 12 and 14 and has relatively few amino acids which are not identical to, or a biologically functional equivalent of, the amino acids of an amino acid sequence of any of SEQ ID NOs:2, 4. 12 and 14. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids in any of SEQ ID NOs: 2, 4, 12 and 14, will be sequences which "a sequence essentially as set forth in SEQ ID NOs:2, 4, 12 and 14".

In particular embodiments, the invention concerns gene therapy methods that use isolated DNA segments and recombinant vectors incorporating DNA sequences which encode a protein that includes within its amino acid sequence an amino acid sequence of any of SEQ ID NOs:2, 4, 12 and 14, SEQ ID NOs:2, 4, 12 and 14 including sequences which are derived from human tissue. In other particular embodiments, the invention concerns isolated DNA sequences and recombinant DNA vectors incorporating DNA sequences which encode a protein that includes within its amino acid sequence the amino acid sequence of the CPSI protein from human hepatic tissue.

In certain other embodiments, the invention concerns isolated DNA segments and recombinant vectors that include within their sequence a nucleic acid sequence essentially as set forth in any of SEQ ID NO:1, 3, 11 and 13. The term "a sequence essentially as set forth in any of SEQ ID NO:1, 3, 11 and 13" is used in the same sense as described above and means that the nucleic acid sequence substantially corresponds to a portion of any of SEQ ID NOs:1, 3, 11 and 13, respectively, and has relatively few codons which are not identical, or functionally equivalent, to the codons of any of SEQ ID NOs:1, 3, 11 and 13, respectively. Again, DNA segments which encode gene products exhibiting activity in the urea cycle, cross-reactivity with an anti-CPSI antibody, or other biological activity of the CPSI gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to a nucleic acid sequence set for in any of SEQ ID NOs:1, 3, 11 and 13 respectively, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent CPSI proteins and peptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged, e.g. substitution of Ile and Leu at amino acids 4 and 5 is SEQ ID NOs:11–14. Changes designed by man may be introduced through the application of site-directed mutagenesis techniques, e.g., to introduce improvements to the antigenicity of the protein or to test CPSI mutants in order to examine activity in the urea cycle, or other activity at the molecular level.

If desired, one may also prepare fusion proteins and peptides, e.g., where the CPSI coding region is aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the CPSI gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a CPSI gene in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems provided for use in high-level expression include, but are not limited to, the vaccina virus promoter and the baculovirus promoter.

In an alternative embodiment, the present invention provides an expression vector comprising a polynucleotide that encodes a CPSI polypeptide having activity in the urea cycle, cross-reacting with an anti-CPSI antibody, or other biological activity in accordance with the present invention. Also preferably, an expression vector of the present invention comprises a polynucleotide that encodes a human CPSI gene product. More preferably, an expression vector of the present invention comprises a polynucleotide that encodes a polypeptide comprising an amino acid residue sequence of any of SEQ ID NOs:2, 4, 12 and 14. More preferably, an expression vector of the present invention comprises a polynucleotide comprising the nucleotide base sequence of any of SEQ ID NO:1, 3, 11 and 13.

Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a CPSI polypeptide having activity in the modulation of the urea cycle, cross-reactivity with an anti-CPSI antibody, or other biological activity in accordance with the present invention. SEQ ID NO's: 1–4 and 11–14 set forth nucleotide and amino acid sequences from an exemplary vertebrate, human. Also provided by the present invention are homologous or biologically equivalent polynucleotides and CPSI polypeptides found in other vertebrates, including rat. Also provided by the present invention are homologous or biologically equivalent polynucleotides and CPSI polypeptides found in invertebrates, including bacteria and yeast.

Preferably, a recombinant host cell of the present invention is transfected with the polynucleotide that encodes human CPSI polypeptide. More preferably, a recombinant host cell of the present invention is transfected with the polynucleotide sequence of any of SEQ ID NOs:1, 3, 11 and 13. Even more preferably, a host cell of the invention is a eukaryotic host cell. Still more preferably, a recombinant host cell of the present invention is a vertebrate cell. Preferably, a recombinant host cell of the invention is a mammalian cell.

In another aspect, a recombinant host cell of the present invention is a prokaryotic host cell. Preferably, a recombinant host cell of the invention is a bacterial cell, preferably a strain of *Escherichia coli*. More preferably, a recombinant host cell comprises a polynucleotide under the transcriptional control of regulatory signals functional in the recombinant host cell, wherein the regulatory signals appropriately control expression of the CPSI polypeptide in a manner to enable all necessary transcriptional and post-transcriptional modification.

In yet another embodiment, the present invention provides a method of preparing a CPSI polypeptide comprising transfecting a cell with polynucleotide that encodes a CPSI polypeptide having activity in the urea cycle, cross-reacting with an anti-PSI antibody, or other biological activity in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of *Escherichia coli*. Even more preferably, a polynucleotide transfected into the transformed cell comprises a nucleotide base sequence of any of SEQ ID NOs:1, 3, 11 and 13. SEQ ID NO's:1–4 and 11–14 set forth nucleotide and amino acid sequences for an exemplary vertebrate, human. Also provided by the present invention are homologues or biologically equivalent CPSI polynucleotides and polypeptides found in other vertebrates, particularly warm blooded vertebrates, and more particularly rat. Also provided by the present invention are homologous or biologically equivalent polynucleotides and CPSI polypeptides found in invertebrates, including bacteria and yeast.

As mentioned above, in connection with expression embodiments to prepare recombinant CPSI proteins and peptides, it is contemplated that longer DNA segments will most often be used, with DNA segments encoding the entire CPSI protein, functional domains or cleavage products thereof, being most preferred. However, it will be appreciated that the use of shorter DNA segments to direct the expression of CPSI peptides or epitopic core regions, such as may be used to generate anti-CPSI antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 4,500 to about 4,600 nucleotides for a protein in accordance with any of SEQ ID NOs: 2, 4, 12 and 14.

Figure 9:
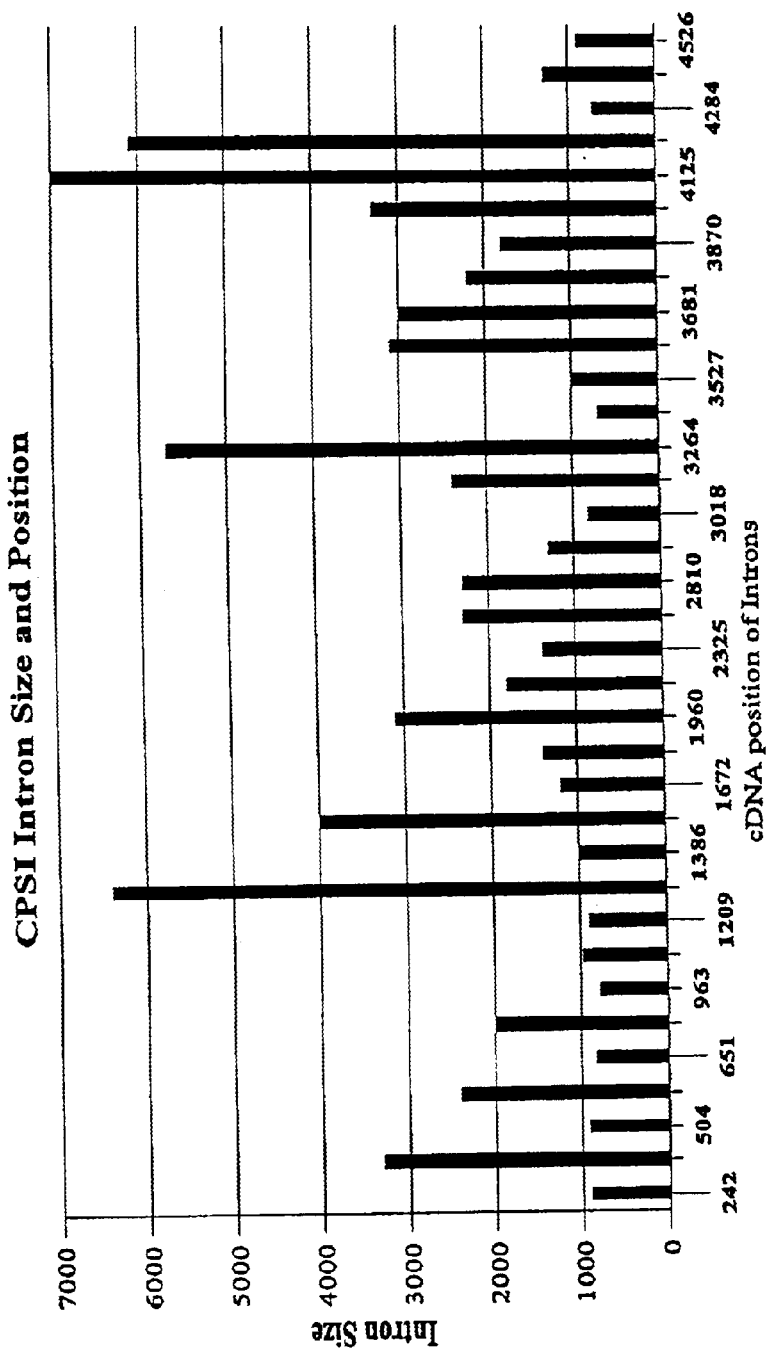
FIG. 9 is a graphical presentation of the size and position of introns in CPSI cDNA.

Naturally, the present invention also encompasses DNA segments which are complementary, or essentially complementary, to the sequences set forth in any of SEQ ID NO's: 1, 3, 11 and 13. The terms "complementary" and "essentially complementary" are defined above. Excepting intronic or flanking regions, details of which are disclosed graphically in FIG. 9, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides in any of SEQ ID NOs:1, 3, 11 and 13 will be sequences which are "a sequence essentially as set forth in any of SEQ ID NOs:1, 3, 11 and 13". Sequences which are essentially the same as those set forth in any of SEQ ID NOs:1, 3, 11 and 13 may also be functionally defined as sequences which are capable of hybridizing to a nucleic acid segment containing the complement in any of SEQ ID NOs:1, 3, 11 and 13 under relatively stringent conditions. Suitable relatively stringent hybridization conditions are described herein and will be well known to those of skill in the art.

C.2. Biologically Functional Equivalents

As mentioned above, modification and changes may be made in the structure of the CPSI proteins and peptides described herein and still obtain a molecule having like or otherwise desirable characteristics. For example, certain amino acids may be substituted for other amino acids in a protein structure without appreciable loss of interactive capacity with structures such as, for example, in the nucleus of a cell. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by applicants that various changes may be made in the sequence of the CPSI proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where if any changes, for example, in the phosphorylation domains of a CPSI polypeptide, could result in a loss of an aspect of the utility of the resulting peptide for the present invention.

Amino acid substitutions, such as those which might be employed in modifying the CPSI proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, *J. Mol. Biol.* 157:105–132 (1982), incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

C.3. Sequence Modification Techniques

Modifications to the CPSI proteins and peptides described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucdeotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, a human CPSI polypeptide. An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful CPSI polypeptide or other species having activity in the urea cycle and is not meant to be limiting as there are other ways in which sequence variants of these peptides may be obtained. For example, recombinant vectors encoding the desired genes may be treated with mutagenic agents to obtain sequence variants (see. e.g., a method described by Eichenlaub, 1979) for the mutagenesis of plasmid DNA using hydroxylamine.

C.4. Other Structural Equivalents

In addition to the CPSI peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

D. Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the CPSI gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., a CPSI promoter for a CPSI gene) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the human CPSI gene including allelic variations thereof, it is proposed that one will desire to preferably employ a vector construct that will deliver the desired gene to the affected cells. This will, of course, generally require that the construct be delivered to the targeted cells, for example, mammalian hepatic cells. It is proposed that this may be achieved most preferably by introduction of the desired gene through the use of a viral vector to carry the CPSI sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency. Suitable vector-CPSI gene constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Where a CPSI gene itself is employed it will be most convenient to simply use a wild type CPSI gene directly. The CPSI gene can thus comprise the threonine encoding allele such that amino acid 1405 of the encoded polypeptide comprises threonine. Alternatively, the CPSI gene comprises the arginine encoding allele such that amino acid 1405 of the encoded polypeptide comprises arginine. Additionally, it is envisioned that certain regions of a CPSI gene can be employed exclusively without employing an entire wild type CPSI gene or an entire allelic variant thereof. It is proposed that it will ultimately be preferable to employ the smallest region needed to modulate the urea cycle so that one is not introducing unnecessary DNA into cells which receive a CPSI gene construct. Techniques well known to those of skill in the art, such as the use of restriction enzymes, will allow for the generation of small regions of an exemplary CPSI gene. The ability of these regions to modulate the urea cycle can easily be determined by the assays reported in the Examples. In general, techniques for assessing the modulation of the urea cycle are known in the art.

D.1. Transgenic Animals

It is also provided within the scope of the present invention to prepare a transgenic non-human animal which expresses a CPSI gene of the present invention or in which expression of a CPSI gene is "knocked-out". Provided transgenic non-human animals express either the T1405 form of CPSI or the N1405 form of CPSI. A preferred transgenic animal is a mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to an exemplary method for the preparation of a transgenic mouse, cloned recombinant or synthetic DNA sequences or DNA segments encoding a CPSI gene product are injected into fertilized mouse eggs. The injected eggs are implanted in pseudo pregnant females and are grown to term to provide transgenic mice whose cells express a CPSI gene product. Preferably, the injected sequences are constructed having promoter sequences connected so as to express the desired protein in hepatic cells of the transgenic mouse.

D.2. Gene Therapy

CPSI genes can be used for gene therapy in accordance with the present invention. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, CPSI gene therapy directed toward modulation of the urea cycle in a target cell is described. Target cells include but are not limited to hepatic cells and intestinal cells. In one embodiment, a therapeutic method of the present invention provides a method for modulating of the urea cycle in a cell comprising the steps of: (a) delivering to the cell an effective amount of a DNA molecule comprising a polynucleotide that encodes a CPSI polypeptide that modulates the urea cycle; and (b) maintaining the cell under conditions sufficient for expression of said polypeptide.

Delivery is preferably accomplished by injecting the DNA molecule into the cell. Where the cell is in a subject delivering is preferably administering the DNA molecule into the circulatory system of the subject. In a preferred embodiment, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a hepatic cell. Means for transforming or transfecting a cell with a DNA molecule of the present invention are set forth above.

Alternatively, the vehicle is a virus or an antibody that specifically infects or immunoreacts with an antigen of the tumor. Retroviruses used to deliver the constructs to the host target tissues generally are viruses in which the 3'-LTR (linear transfer region) has been inactivated. That is, these are enhancerless 3'-LTR's, often referred to as SIN (self-inactivating viruses) because after productive infection into the host cell, the 3'-LTR is transferred to the 5'-end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

Antibodies have been used to target and deliver DNA molecules. An N-terminal modified poly-L-lysine (NPLL)-antibody conjugate readily forms a complex with plasmid DNA. A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

It is also envisioned that this embodiment of the present invention can be practiced using alternative viral or phage vectors, including retroviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

By way of specific example, a human CPSI-encoding polynucleotide or a CPSI-encoding polynucleotide homolog from another warm-blooded vertebrate or a CPSI-encoding homolog from an invertebrate source, such as bacteria or yeast is introduced into isolated hepatic cells or other relevant cells. The re-injection of the transgene-carrying cells into the liver or other relevant tissues provides a treatment for susceptibility to hyperammonemia or other relevant diseases in human and animals.

E. Supplementation Therapy

In addition to its role in nitrogen clearance, the urea cycle is the body's intrinsic source of arginine which acts as a precursor of nitric oxide (NO), a potent vasodilator. Methods of treating suboptimal urea cycle function are provided in accordance with the present invention, including treatment by administration of nitric oxide precursors such as citrulline. Typically, the suboptimal urea cycle function is associated with the polymorphism disclosed herein. The suboptimal urea cycle function can further comprise hyperammonemia or decreased arginine production.

The subject to be treated can be suffering from a disorder associated with sub-optimal urea cycle function. Such disorders include but are not limited to disorders that involve impaired or damaged liver and/or gut tissue. Representative disorders include but are not limited to hepatitis (including hepatitis A, B and C), sclerosis, pulmonary hypertension, bone marrow transplant toxicity in a subject undergoing bone marrow transplant and combinations thereof.

The subject to be treated can also exposed or about to be exposed to an environmental stimulus associated with sub-optimal urea cycle function. Such environmental stimuli include but are not limited to stimuli that involve impairment or damage to liver and/or gut tissue. Representative environmental stimulus include but are not limited to chemotherapy or other pharmaceutical therapy, cardiac surgery, increased oxidative stress, bone marrow transplant, and combinations thereof.

Thus, a method of treating or preventing a disorder related to sub-optimal urea cycle function in a subject is provided in accordance with the present invention. The method comprises administering to the subject a therapeutically effective amount of a nitric oxide precursor, whereby treatment or prevention of the disorder is accomplished. The nitric oxide precursor can include but is not limited to citrulline, arginine and combinations thereof. The nitric oxide precursor is administered in a dose ranging from about 0.01 mg to about 1,000 mg, preferably in a dose ranging from about 0.5 mg to about 500 mg, and more preferably in a dose ranging from about 1.0 mg to about 250 mg.

Optionally, the supplementation therapy method of the present invention further comprises the step of initially detecting a polymorphism of a carbamyl phosphate synthase I (CPSI) gene in the subject. The polymorphism of the carbamyl phosphate synthetase polypeptide preferably comprises a C to A transversion within CPSI exon 36, more preferably comprises a C to A transversion at nucleotide 4340 of a cDNA that corresponds to the CPSI gene, and ever more preferably, the C to A transversion at nucleotide 4340 of the cDNA that corresponds to the CPSI gene further comprises a change in the triplet code from AAC to ACC, which encodes a CPSI polypeptide having an threonine moiety at amino acid 1405.

A significant decrease in urea cycle intermediates (citrulline, arginine) was observed in subjects undergoing BMT associated with the T1405N CPSI polymorphism disclosed herein. In accordance with the present invention, a method for the treatment or prophylaxis of BMT toxicity, such as HVOD, comprising administering a therapeutically effective amount of a NO precursor, such as citrulline and/or arginine, to a subject in need thereof is also provided in accordance with the present invention. Preferably, the T1405N CPSI polymorphism disclosed herein is present in the subject More preferably, a therapeutically effective amount of citrulline is administered to the subject.

In accordance with the present invention, a method of reducing toxicity and/or the occurrence of HVOD in a subject undergoing BMT is thus provided. This method comprises administering the BMT subject an effective amount of arginine and/or citrulline, with citrulline being preferred, to bolster arginine and NO synthesis in the subject. The bolstering of arginine and NO synthesis in the subject will reduce and/or substantially prevent the occurrence of HVOD associated with BMT. Citrulline is a preferred supplementation agent given that it is more readily converted to NO. Additionally and preferably, subjects having the CPSI polymorphism of the present invention are contemplated to be preferred candidates for supplementation in accordance with this method.

The subject treated in the present invention in its many embodiments is desirably a human subject, although it is to be understood that the principles of the invention indicate that the invention is effective with respect to all vertebrate species, including warm-blooded vertebrates such as mammals and birds, which are intended to be included in the term "subject". In this context, a mammal is understood to include any mammalian species in which treatment of hyperammonemia, BMT toxicity and other diseases associated with impaired urea cycle function is desirable, particularly agricultural and domestic mammalian species.

Thus, contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

The amount of active ingredient that may be combined with the carrier materials to produce a single dosage form will vary depending upon the host treated and the particular mode of administration. For example, a formulation intended for administration to humans may contain from 0.5 mg to 5 g of active agent compounded with an appropriate and convenient amount of carrier material which may vary from about 5 to about 95 percent of the total composition. For example, in a human adult, the doses per person per administration are generally between 1 mg and 500 mg up to several times per day. Thus, dosage unit forms will generally contain between from about 1 mg to about 500 mg of an active ingredient, typically 25 mg, 50 mg, 100 mg, 200 mg, 300 mg, 400 mg. 500 mg. 600 mg, 800 mg, or 1000 mg.

It will be understood, however, that the specific dose level for any particular subject will depend upon a variety of factors including the age, body weight, general health, sex, diet, time of administration, route of administration, rate of excretion, drug combination and the severity of the particular disease undergoing therapy.

F. Pharmaceutical Compositions

In a preferred embodiment, the present invention provides pharmaceutical compositions comprising a polypeptide or polynucleotide of the present invention and a physiologically acceptable carrier. More preferably, a pharmaceutical composition comprises a polynucleotide that encodes a biologically active CPSI polypeptide. Alternatively, provided pharmaceutical compositions comprise citrulline or arginine in dosages as described above.

A composition of the present invention is typically administered orally or parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, in the case of a pharmaceutical composition provided for use in gene therapy, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intra-vascularly).

G. Generation of Antibodies

In still another embodiment, the present invention provides an antibody immunoreactive with a polypeptide or polynucleotide of the present invention. Preferably, an antibody of the invention is a monoclonal antibody. Means for preparing and characterizing antibodies are well known in the art (See, e.g., *Antibodies A Laboratory Manual*, E. Howell and D. Lane, Cold Spring Harbor Laboratory, 1988). More preferred antibodies distinguish between the different forms of CPSI which comprise the CPSI polymorphism.

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunizaton. When a desired level of immunogenicity is obtained, the immunized animal can be bled and the serum isolated and stored.

In another aspect, the present invention provides a method of producing an antibody immunoreactive with a CPSI polypeptide, the method comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the CPSI polypeptide is capable of mediating the first step of the urea cycle, cross-reacting with anti-CPSI antibody, or other biological activity in accordance with the present invention. Even more preferably, the present invention provides antibodies prepared according to the method described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrlmidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

H. Detecting a Polynucleotide or a Polypeptide of the Present Invention

Alternatively, the present invention provides a method of detecting a polypeptide of the present invention, wherein the method comprises immunoreacting the polypeptides with antibodies prepared according to the methods described above to form antibody-polypeptide conjugates, and detecting the conjugates.

In yet another embodiment, the present invention provides a method of detecting messenger RNA transcripts that encode a polypeptide of the present invention, wherein the method comprises hybridizing the messenger RNA transcripts with polynucleotide sequences that encode the polypeptide to form duplexes; and detecting the duplex. Alternatively, the present invention provides a method of detecting DNA molecules that encode a polypeptide of the present invention, wherein the method comprises hybridizing DNA molecules with a polynucleotide that encodes that polypeptide to form duplexes; and detecting the duplexes.

The detection and screening assays disclosed herein can be used as a prognosis tool. Human CPSI-encoding polynucleotides as well as their protein products can be readily used in clinical setting as a prognostic indicator for screening for susceptibility to hyperammonemia and to other heritable CPSI-related diseases in humans.

The detection and screening assays disclosed herein can be also used as a part of a diagnostic method. Human CPSI-encoding polynucleotides as well as their protein products can be readily used in clinical setting to diagnose susceptibility to hyperammonemia and to other heritable CPSI-related diseases in humans.

H.1. Screening Assays for a Polypeptide of the Present Invention

The present invention provides a method of screening a biological sample for the presence of a CPSI polypeptide. Preferably, the CPSI polypeptide possesses activity in the urea cycle, cross-reactivity with an anti-CPSI antibody, or other biological activity in accordance with the present invention. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide. Hepatic tissues comprise particularly contemplated tissues.

Preferably, antibodies which distinguish between the N1405 CPSI polypeptide and the T1405 CPSI polypeptide are provided. Such antibodies may compare polyclonal antibodies but are preferably monoclonal antibodies prepared as described hereinabove.

In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}P$, $^{125}I$, $^{14}C$), a second antibody or an enzyme such as horse radish peroxidase. Means for affixing indicators to antibodies are well known in the art. Commercial kits are available.

H.2. Screening Assay for Anti-polypeptide Antibody

In another aspect, the present invention provides a method of screening a biological sample for the presence of antibodies immunoreactive with a CPSI polypeptide. Preferably the CPSI polypeptide has activity in the urea cycle, cross-reactivity with an anti-CPSI antibody, or other biological activity in accordance with the present invention. In accordance with such a method, a biological sample is exposed to a CPSI polypeptide under biological conditions and for a period of time sufficient for antibody-polypeptide conjugate formation and the formed conjugates are detected.

H.3. Screening Assay for Polynucleotide That Encodes a CPSI Polypeptide of the Present Invention A nucleic acid molecule and, particularly a probe molecule, can be used for hybridizing as an oligonucleotide probe to a nucleic acid source suspected of encoding a CPSI polypeptide of the present invention. Optimally, the CPSI polypeptide has activity in the urea cycle, cross-reactivity with an anti-CPSI antibody, or other biological activity in accordance with the present invention. The probing is usually accomplished by hybridizing the oligonucleotide to a DNA source suspected of possessing a CPSI gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization method of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from subject's cells, such as a CPSI polymorphism described herein; (2) means for detecting and isolating other members of the polypeptide family and related polypeptides from a DNA library potentially containing such sequences; (3) primers for hybridizing to related sequences for the purpose of amplifying those sequences; (4) primers for altering native CPSI DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected CPSI gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as a sequence shown in any of SEQ ID NOs:1, 3, 11 and 13. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid imolecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M salt at temperatures of about 50° C. to about 70° C. including particularly temperatures of about 55° C., about 60° C. and about 65° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M–0.9M salt, at temperatures ranging from about 20° C. to about 55° C., including particularly temperatures of about 25° C., about 37° C., about 45° C., and about 50° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

H.4. Assay Kits

In another aspect, the present invention provides a diagnostic assay kit for detecting the presence of a polypeptide of the present invention in biological samples, where the kit comprises a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also provides a diagnostic kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides diagnostic assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, in any of SEQ ID NOs:1, 3, 11 and 13.

In another embodiment, the present invention provides diagnostic assay kits for detecting the presence, in a biological sample, of antibodies immunoreactve with a polypeptide of the present invention, the kits comprising a first container containing a CPSI polypeptide, that immunoreacts with the antibodies, with the polypeptide present in an amount sufficient to perform at least one assay. Preferably, the CPSI polypeptide has activity in the urea cycle, cross-reactivity on an anti-CPSI antibody, or other biological activity in accordance with the present invention. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

EXAMPLES

The following Examples have been included to illustrate preferred modes of the invention. Certain aspects of the following Examples are described in terms of techniques or procedures found or contemplated by the present inventors to work well in the practice of the invention. These Examples are exemplified through the use of standard laboratory practices of the inventors. In light of the present disclosure and the general level of skill in the art, those of skill will appreciate that the following Examples are intended to be exemplary only in that numerous changes, modification, and alterations can be employed without departing from the spirit and scope of the invention.

Materials and Methods Used in Examples 1–3

The following materials and methods are employed in each of Examples 1–3. Additional materials and methods are also described in each Example.

Clinical/Patient Recruitment: More than 200 patients undergoing BMT at Vanderbilt University Medical Center, Nashville, Tenn. have been enrolled in the BMT-Lung Injury Following Engraftment (LIFE) Study aimed at understanding mechanisms of acute lung injury and multiple organ failure after transplant. Consent was sought from consecutive patients undergoing BMT or PBSCT for treatment of malignancy. Definitions of organ failure (including HVOD) and reversal were prospectively defined and data was collected concurrently during hospitalization. Plasma, cell pellets, and urine were collected at study enrollment (before receiving chemotherapy) and on the day of transplantation (before marrow infusion) after completing ablative chemoradiotherapy.

Amino Acid Analysis—Blood and urine were immediately centrifuged after collection. All samples were kept on ice, then stored at $-70°$ C. until analyzed. Under these storage conditions, glutamine, cysteine and homocysteine are known to decrease, so these were not used in the analysis. Plasma amino acids were measured in the Vanderbilt Diagnostic Laboratories, Vanderbilt University, Nashville, Tenn. Briefly, a protein free extract of plasma was prepared by protein precipitation with sulfosalicylic acid and filtration through a 0.45 $\mu$m ACRODISC™ 4 filter (Gelman Sciences, Ann Arbor, Mich.). Amino acids were separated by cation exchange chromatography using a four-component pH- and ionic strength-graded lithium citrate buffer system on a Beckmann 7300 amino acid analyzer (Beckmann, Palo Alto, Calif.). Post column derivatization of amino acids with ninhydrin allowed detection of primary amine amino acids at 570 nm, and secondary amines at 440 nm. Quantification was achieved by instrument calibration with standard reference materials (Sigma, St. Louis, Mo.).

Statistics. Plasma amino acid values were expressed as mean±SEM. Comparisons between baseline and post-chemotherapy amino acid values were made using Student's t-Test. Allelic frequency was compared between patients with and without HVOD using Chi square analysis.

Patients. Patients were identified from those enrolled in the BMT Lift Study at Vanderbilt University. DNA was isolated from pre-transplant blood or spun urine samples. HVOD status was determined using the Baltimore criteria:

Bilirubin>2.0 mg/dl

Hepatomegaly

2% sudden weight gain

Genotyping. DNA was isolated using a QIAmp™ blood kit (Qiagen). The T1405N polymorphism changes the DNA sequence as follows:
CCT-GCC-A<u>C</u>C-CCA-GTG Normal
CCT-GCC-A<u>A</u>C-CCA-GTG Change The C to A transversion replaces the pyrimidine C with the purine A which destroys a Msl 1 site. The use of a primer from within the 35th intron of CPSI and an exotic primer from exon 36 of the CPSI gene reliably PCR amplifies a 387 bp fragment encompassing the region containing the change. This combination gives a robust amplification. PCR Ready-to-Go™ beads are also used in amplification (Pharmacia).

The polymorphism was detected using a non-denaturing gel to take advantage of the secondary structures created by the C to A transversion. This change creates enough secondary structure to prevent reliable digestion by restriction enzymes (Msl 1) to detect the polymorphism. This change also interferes with direct sequence analysis unless ITP is substituted for GTP in the reaction. Non-denaturing gels take advantage of the secondary structures created by this change. Fifteen (15) individuals were compared by this method and sequence analysis.

To detect the DNA fragments in the gel, a silver staining technique was adapted. This inexpensive rapid method allowed visualization of bands shortly after electrophoresis.

Statistical Analysis. A sufficient sample size was obtained to perform Chi Square analysis on the results. The Hardy-Weinburg equation was used to calculate the expected frequencies for the genotypes ($p^2+2pq+q^2$). P values were obtained from a standard Chi Square table using 2 degrees of freedom.

Example 1

Alleles of CPSI Exonic Polymorphism (T1405N) are not in Hardy-Weinburg Equilibrium With the Presence or Absence of HVOD In accordance with the present invention, a common polymorphism near the 3' end of the CPSI mRNA (about 0.44 heterozygosity) has been identified. Sequence analysis of this change revealed a C to A transversion at base 4340 changing the triplet code from ACC to AAC. This results in a substitution of asparagine for threonine at amino acid 1405 (referred to herein as "T1405N"). The threonine is within the allosteric domain, preceding the signature sequence PV(A/S)WP(T/S)(A/Q)E, a sequence that is important in the binding of the cofactor n-acetyl-glutamate (NAG).

In all known CPSIs activated by NAG, a threonine residue is among the two residues that precede the signature sequence. (Rubio, *Biochemical Society Transactions* 21:198–202 (1998)). On the basis of structure-function studies, hydrogen bond formation with the carbonyl oxygen of the acetamido group of NAG is felt to play a role in the binding of this activator. (Stapleton et al., *Biochemistry* 35:14352–14361 (1996); Javid-Majd et al., *Biochemistry* 35:14362–14369 (1996)). The substitution of the threonine side chain by asparagine is envisioned to alter the hydrogen bond formation with NAG and results in a qualitative change in CPSI enzymatic function and in sensitivity to the available pool of NAG. Although applicants do not wish to be bound by any particular theory of operation, it is speculated that based on the precedent of the effects of other xenobiotics, that limited availability of NAG after escalated dose chemotherapy is one of the mechanisms promoting urea cycle dysfunction.

126 individuals were genotyped from the BMT Life Study group. 30 individuals manifested evidence of HVOD in this group (24%). 70 patients were genotyped from blood samples and 56 from urine cell pellets. Samples from 15 patients were reamplified via PCR and sequenced to confirm the consistency of the results.

Tables 2 and 3 show the results of genotype analysis for the T1405N polymorphism between HVOD+ and HVOD– patients. The C allele, also referred to herein as the CPSIa allele or the threonine encoding allele, has a frequency of 0.62 in the examined population and the A allele, also referred to herein as the CPSIb allele or the asparagine encoding allele, has a frequency of 0.38. The Chi Square value for the table is 4.3 (P=0.1) indicating that the polymorphism is probably not in Hardy-Weinburg equilibrium with the presence of HVOD. Thus, these results provide evidence for disequilibrium in the distribution of the T1405N alleles in BMT patients with HVOD, indicating that the polymorphism can be used to identify subjects who are susceptible to BMT toxicity.

TABLE 2

| Genotype | HVOD+ | HVOD– |
|---|---|---|
| CC | 13 (expected 11.4) | 32 (expected 36.5) |
| AC | 16 (expected 14.1) | 50 (expected 45.1) |
| AA | 1 (expected 4.5) | 14 (expected 14.4) |

TABLE 3

| Total alleles: | Expected Frequencies: |
|---|---|
| A:96 | AA:0.15 |
| C:62 | AC:0.47 |
|  | CC:0.38 |

Additional data gathered from a study of approximately 200 patients provided additional statistical evidence supporting the use of the polymorphism in detection of susceptibility to sub-optimal urea cycle function. This data was subjected to the statistical methods described above.

Bone marrow transplant toxicity results in significant morbidity and mortality. HVOD is associated with a poor prognosis in BMT patients. This study was undertaken to assess an association between the CPSI enzyme and the occurrence of HVOD. The T1465N polymorphism affects CPSI function. Its wide distribution in the population suggests that both forms provide adequate urea cycle function under normal conditions. The addition of metabolic stressors (such as high-dose chemotherapy) serves to lower CPSI efficiency below an effective threshold. Analysis of the data thus suggests that HVOD is more likely to occur in patients with the threonine encoding allele than those with the asparagine. The threonine encoding allele is shared by the rodent form of CPSI.

Example 2

Biochemical and Genetic Alterations in Carbamyl Phosphate Synthetase I in Patients With Post-bone Marrow Transplant Complications Bone marrow transplantation (BMT) and peripheral blood stem cell transplants (PBSCT) are increasingly being used as primary therapy for selected malignancies. Use of stem cell support for hematopoietic reconstitution allows for substantial escalation in the dose of chemotherapy in an attempt to eradicate potentially lethal cancers. With improvements in prophylaxis for infection and prevention of disabling graft-versus-host disease, chemotherapy-induced organ dysfunction remains a significant barrier to more widespread use of this treatment.

Hepatic venocclusive disease (HVOD), a clinical syndrome of hyperbilirubinemia (serum bilirubin >2.0 mg/dL), hepatomegaly, and fluid retention early after BMT, is a major dose-limiting toxicity after BMT, afflicting up to 54% of patients. Many patients developing HVOD after BMT will also meet the criteria for acute lung injury (ALI). Nearly half of patients with severe HVOD require mechanical ventilation, with an attendant mortality in excess of 90%. Such data underscore the large impact on mortality of sequential organ dysfunction, even in a young patient population, and reinforce the clinically important association of poor prognosis after acute lung injury in patients with hepatic dysfunction. The mechanisms responsible for this organ interaction remain incompletely understood.

In this Example, whether conditioning chemotherapy administered prior to BMT might affect early enzymes in the UC and secondarily predispose patients for hepatic dysfunction and multiple organ failure was analyzed. The plasma amino acid analyses supported the notions of both impaired UC function and decreased production of nitric oxide ($NO_x$). In light of these findings, patients were screened for the exonic single nucleotide polymorphism (SNP) in CPS-I disclosed herein. It was found that homozygosity for the SNP was associated with a decreased incidence of HVOD and enhanced early survival after BMT, consistent with a significant pharmacogenetic interaction.

Methods

Clinical/Patient Recruitment: Over the last three years 200 patients undergoing BMT at Vanderbilt University Medical Center have been sequentially enrolled in the Bone Marrow Transplant-Lung Injury Following Engraftment (BMT-LIFE) Study, a coordinated clinical-biochemical exploratory investigation aimed at understanding mechanisms of acute lung injury and multiple organ failure after transplant. Definitions of organ failure and reversal were prospectively defined and data was collected concurrently during hospitalization and until 60 days after BMT. Exclusion criteria included active viral and prior escalated dose therapy with hematopoefic stem cell support (either PBSCT or BMT).

Hepatic venocclusive disease (HVOD) was identified in patients with bilirubin >2 mg/dL before 21 days after transplant with either weight gain >5% of baseline or new onset of tender hepatomegaly. Acute lung injury (ALI) was defined as bilateral infiltrates on chest roentgenogram for three consecutive dates with a ratio of partial pressure of oxygen in arterial blood to the fraction of inspired oxygen concentration($PaO_2/FiO_2$)of less than 300 in the absence of clinical cardiac dysfunction. Patients alive 60 days after transplant were defined as survivors. Plasma, circulating cell pellets, and urine were collected at study enrollment (before receiving chemotherapy) and on the day of BMT, several days after completing high dose chemotherapy but before marrow infusion. Samples were aliquotted, and immediately placed on ice prior to storage at −80° C. before analysis.

Amino Acid Analysis. Amino acid analysis was performed on cryopreserved plasma samples from days −8 and 0 (pre-treatment and day of transplantation) in 60 patients. Patient samples were initially randomly selected for pilot studies; subsequently analyzed samples were specifically enriched to include extra patients with the SNP M genotype of CPS-I (see below) and additional patients with the post-BMT complications of HVOD and ALI. A protein free extract of plasma was prepared by protein precipitation with sulfosalicylic acid and filtration through a 0.45 μm Acrodisc 4 (Gelman Sciences, Ann Arbor, Mich.).

Amino acids were separated by cation exchange chromatography using a four-component pH- and ionic strength-graded lithium citrate buffer system on a Beckmann 7300 amino acid analyzer (Beckmann, Palo Alto, Calif.). Post column derivatization of amino acids with ninhydrin allowed detection of primary amine amino acids at 570 nm, and secondary amines at 440 nm. Quantitation was achieved by instrument calibration with standard reference materials (Sigma, St. Louis, Mo.). Citrulline, arginine, and ornithine were examined as measurable indices of flux of intermediates through the urea cycle.

Measurement of plasma nitric oxide metabolites ($NO_x$). Plasma $NO_x$ was measured in a subgroup of patients using modified Griess reagents after samples were deproteinated and incubated with cadmium beads to convert nitrate to nitrite.

Detection of T1405N polymorphism. Oligonucleotide primers from within the $36^{th}$ exon (CGGAAGCCACATCAGACTGG (SEQ ID NO:15) and intron (GGAGAGTGAAACTTGACAATCATC (SEQ ID NO:16)) of CPS1 and the polymerase chain reaction (PCR) to reliably amplify a 251 bp fragment encompassing the region containing the change from genomic DNA obtained from buffy coat preparations or urinary sediment. This combination of primers gave reproducible amplification using PCR Ready-to-Go beads (Pharmacia) and PCR cycle conditions as follows: 35 cycles of 1 minute anneal at 55° C., 1 minute extension at 72° C., and 1 minute denaturation at 94° C.

After formamide treatment, samples were subjected to electrophoresis for 4 hours at 4° C. in a non-denaturing MDE™ gel (FMC, Rockland, Me.), then stained with silver nitrate to detect DNA fragments. Confirmatory genotyping of 17 individuals using both non-denaturing gel electrophoresis and direct sequence analysis yielded identical results. Patients were classified as having homozygous SNP genotypes of CC or AA, or as being heterozygous (AC). For comparison, using identical methods, a cohort of 100 patients with Alzheimer's disease was analyzed to assess the distribution of CPSI SNP genotypes.

Statistical Analysis. Plasma amino acid levels before and after chemotherapy, and levels between groups of patients, were compared using Student's T-test or Wilcoxon's Rank Sum Test (if the data were not normally distributed). Distribution of genotypes of CPSI was compared across groups by calculating allelic frequency for the entire group and searching for evidence of Hardy-Weinberg disquilibrium in specifically selected subgroups using $P^2$ analysis. Sensitivity, specificity, predictive values, and relative risk assessments were generated from two-by-two contingency tables constructed using specific amino acid values in groups of patients divided by presence and absence of specific clinical outcomes (e.g. HVOD, ALI, and death).

Results

Two hundred patients were enrolled in the BMT-LIFE Study. 52% underwent autologous transplant (mean age 46±1 years); 48% received allogeneic grafts (mean age 40±1 years). Of the patients undergoing allogeneic transplants, 24% received grafts from HLA-matched unrelated donors. Nearly two-thirds of the patients in the autologous group were women, reflecting the increased prevalence of breast cancer in this population. The indications for transplant were diverse, but 79% of the patients were transplanted for breast cancer, leukemia, or non-Hodgkin's lymphoma. The different preparative regimens used prior to BMT included CTC (cyclophosphamide, thiotepa, carboplatin), BuCy (busulfan, cyclophosphamide), CVP16TBI (cyclophosphamide, etoposide, total body irradiation), CBVP16 (cyclophosphamide, bis-chloroethylnitrosourea, etoposide) and TC (thiotepa, cydophosphamide).

Both morbidity and mortality are not uncommon after BMT. While the overall 60 day mortality in the study was 14%, it was 20% in patients receiving allografts. Complications of acute lung injury (ALI) and hepatic venocclusive disease (HVOD) each occurred in 19% of the patients. These complications were more than twice as common in patients receiving allografts. In the group of patients developing HVOD, 62% (24/38) also met criteria for ALI during hospitalization. Only 38% (14/38) of the cases of ALI occurred in patients who never met criteria for HVOD.

A subset (60/200) of the patients, specifically enriched during sample selection with extra patients with CPS-I AA SNP genotype and additional patients with post-transplant complications, had plasma amino acid determinations before administration of chemotherapy and on the day of transplant. Comparison of levels of selected amino acids that participate in the UC (citrulline, ornithine, and arginine) before and after chemotherapy revealed significant differences. Citrulline levels fell in virtually all patients with a mean group decrease from 23.4±1.3 $\mu$M to 9.1±0.7 $\mu$M (P<0.05). Arginine levels rose by approximately 35% (P<0.05), and ornithine levels rose by 21% (P<0.05).

The ratio of ornithine/citrulline (O/C ratio), an index of flux through the early steps of the UC (i.e. lower values indicate better cycle flow), increased from 3.9±0.7 at study enrollment to 11.8±1.8 after induction chemotherapy (P<0.05). Shifts also occurred in amino acids that are not part of the UC. Levels of glycine and alanine, two aliphatic amino acids, fell significantly by 11% and 19%, respectively, in a pattern not consistent with decreased flux of intermediates through the cycle simply due to decreased protein intake (acute or chronic). Phenylalanine and methionine levels rose by 43% and 23%, respectively, suggesting subclinical hepatic dysfunction.

Baseline plasma levels of citrulline and the O/C ratios had prognostic importance. Sixty day survivors of BMT had higher baseline levels of citrulline than did nonsurvivors (24.4±1.3 vs 17.7±2.9 $\mu$M, respectively; P<0.05). The relative risk for death before 60 days after BMT was 2.92 for patients with an enrollment citrulline level less than 20. The negative predictive value for death of a plasma citrulline level greater than 20 $\mu$M was 90%. O/C ratios at enrollment were significantly lower in patients never developing either HVOD (2.8±0.2) or ALI (2.9±0.2) when compared to patients who subsequently developed these complications (5.8±1.9 and 6.5±2.7, respectively; P<0.05). Comparison of O/C ratios between 60 day survivors and nonsurvivors of BMT at study enrollment showed a trend toward lower values in survivors (3.3±0.2 vs. 6.9±3.9; P=0.06). The negative predictive value for death within 60 days after BMT associated with a baseline O/C ratio less than 2.5 was 92%.

Several urea cycle amino acid intermediate levels after preparative therapy, on the day of BMT, also had significance. Plasma arginine levels were higher in survivors (114.5±5.9 $\mu$M) when compared to nonsurvivors (92.3±10.4 $\mu$M) (P<0.05). O/C ratios were significantly higher, suggesting more impaired UCF, in patients who later developed ALI when compared to those never developing severe lung dysfunction (18.4±5.9 vs 9.5±0.7; P<0.05). Although the negative predictive value for development of ALI of a post-chemotherapy O/C ratio less than ten was high (86%), the relative risk for mortality associated with this threshold was only 1.44. There was a trend toward higher O/C ratios in patients on the day of BMT in patients who subsequently developed HVOD (P=0.09).

Levels of nitric oxide metabolites ($NO_x$) in plasma were measured in 62 patients. Plasma $NO_x$ levels fell 20% after induction therapy, from 40±2 $\mu$M at study enrollment to 32±2 $\mu$M on the day of BMT (P<0.05). The median $NO_x$ value on the day of BMT in 20 patients developing either HVOD or ALI was 28 $\mu$M; for patients without such complications the plasma $NO_x$ was 35 $\mu$M. No clear differences between plasma $NO_x$ was observed when patients with different CPSI SNP genotypes were compared.

To assess whether certain patients might have a genetic predisposition to develop morbid complications following induction therapy and BMT, all patients in the study were genotyped for a CPSI SNP. Of 200 patients, data was analyzed from 196 patents (i.e. 2 clinical exclusions; 2 unsuccessful PCR amplifications) to determine if the CPS-I C4340A SNP was in Hardy-Weinberg equilibrium with the development of HVOD. The distribution of CPSI SNP genotypes in patients undergoing BMT was identical to that of the control group (100 patients with Alzheimer's disease): 44% CC (wild type), 45% AC (heterozygous), and 11% AA (homozygous for the transversion). The attack rate of HVOD in those with the CC or AC genotype were 18% and 24%, respectively. There were no cases of HVOD in patients with the AA genotype.

Finding that this allelic distribution was not in Hardy-Weinburg equilibrium with the development of HVOD ($P^2$=5.06, P<0.05) suggests that the SNP AA genotype alters susceptibility to hepatic toxicity following induction chemotherapy. There were also trends toward differences in mortality 60 days after BMT between the SNP genotypes. Nonsurvivors constituted 15% and 20% of the AC and CC genotype groups, respectively. Interestingly, all of the patients with the AA genotype survived 60 days after BMT ($P^2$=3.36; P=0.06). Of note, almost all of the $P^2$ score came from the AA/survivor cell. There were no significant differences between patients with different SNP C4340A genotypes in the attack rate of ALI (16%, 15%, and 25% in the AA, AC, and CC groups, respectively). While ALI was associated with significant mortality in patients with either the AC or CC genotypes (71% and 66%, respectively), all patients with the AA genotype who developed ALI eventually had resolution of both bilateral pulmonary infiltrates on CXR and impaired gas exchange and survived 60 days after BMT.

Discussion

The data presented in this Example reflect a close association between HVOD and ALI in patients after BMT, with nearly two-thirds of patients with HVOD meeting criteria for ALI. In this study, 68% (26/38) of patients developing ALI required mechanical ventilation. Rubenfelt and Crawford have reported a meaningful survival, defined as extubation followed by discharge from the hospital with thirty day survival, of only 6% in patients requiring mechanical ventilation after BMT. See Rubenfeld, G. D. and Crawford, S. W., *Annals of Internal Medicine* (1996)125:625–33.

HVOD remains the major dose limiting toxicity of escalated dose chemotherapy. It is clinically characterized by fluid retention, jaundice, ascites, and painful hepatic enlargement occurring within 3 weeks of BMT. Autopsy studies of those non-surviving patients fulfilling these clinical criteria provide histological confirmation in >80% of cases and are consistent with the idea that enhanced local thrombosis might be an initiating event in the pathogenesis of HVOD.

The significant fall in citrulline levels and rise in plasma ornithine levels from patients undergoing BMT suggests a significant disturbance in flux of carbon intermediates through the hepatic UC in patients after induction chemotherapy. Analysis of the patterns of other amino acids argues that this effect is not simply due to decreased protein intake. In contrast to the patterns seen in patients with starvation, where levels of glycine and branched chain amino acids (BCAA) are usually significantly elevated, we observed a fall in glycine and no significant change in the BCAAs. Furthermore, starvation tends to increase activity of CPSI in liver and should not lead to increases in plasma ornithine.

The pretreatment ability of patients undergoing BMT to maintain flow of intermediates through the UC had particular prognostic importance. Sixty day nonsurvivors after BMT and those patients developing HVOD or ALI had significantly lower levels of citrulline and higher O/C ratios compared to patients who did not develop these complications. Of interest was the observation that nonsurvivors of BMT had lower plasma arginine values after induction therapy when compared to surviving patients. In light of the clustering of cells containing early UC enzymes about the terminal hepatic venules, local concentrations of both arginine and nitric oxide (NO) might be much higher and might play an important role in maintaining patency of these vessels and regulating regional hepatic blood flow. The studies showing a significant reduction in plasma $NO_x$ levels after induction chemotherapy support the idea that NO production is altered during BMT.

The apparent discrepancy between apparently normal plasma levels of arginine on the day of transplant and markedly reduced plasma $NO_x$ underscores the complex in vivo kinetics of arginine and citrulline flux across different organ beds. Stable isotope studies of whole body arginine homeostasis have indicated that only about 15% of plasma arginine turnover is associated with urea formation, and that only 1.2% of plasma arginine turnover is associated with NO formation. Furthermore, in vitro studies have documented substantial channeling of urea cycle intermediates, from citrulline to arginine, that is not influenced by exogenous provision of substrate. The ability of an individual patient to maintain urea cycle function and hepatic NO production during the stresses of induction chemotherapy can, in part, influence their resistance to complications after BMT.

Since there is no gender disparity in the occurrence of HVOD, we concentrated on potential pharmacogenetic issues related to CPSI, an autosomally encoded gene, rather than on the X-linked ornithine transcarbamylase gene. While characterizing the molecular changes underlying the causes of neonatal and late-onset CPSI deficiency, a common SNP near the 3' end of the CPSI mRNA (0.44 heterozygosity) was identifed. This C4340A transversion encodes a predicted substitution of asparagine (AAC) for threonine (ACC) at amino acid 1405 (T1405N). This threonine is within the allosteric domain, preceding the sequence PV(A/S)WP(T/S)(A/Q)E important in the binding of a cofactor, n-acetyl-glutamate (NAG), that increases enzyme activity. Although applicants do not wish to be bound by any particular theory of operation, it is speculated that based on the precedent of the effects of other xenobiotics, that limited availability of NAG after escalated dose chemotherapy is one of the mechanisms promoting urea cycle dysfunction. Nonetheless, it appears that the presence of the CPS-I SNP AA genotype is associated with protection against the development of HVOD, resolution of ALI if it occurs, and improved 60 day survival after BMT. Thus, the data suggest that alteration in UC function plays a role in modifying liver-lung interaction during sepsis and acute lung injury.

In summary, this Example documents significant impairment in hepatic UC function in patients who receive escalated dose chemotherapy prior to BMT. Patients with more severe derangement in cycle function are more likely to develop morbid complications after BMT. Additionally, a significant association between a CPS-I C4340A SNP and both post-BMT complications and short-term survival has been found. Such data are useful in assessment of risk for patients undergoing BMT and provide a rationale for therapeutic attempts to support UC function during high-dose chemotherapy.

Example 3

Arginine/Citrulline Supplementation Therapy

The added decrease in urea cycle products (arginine and citrulline) and increase in precursors (ammonia, glutamine, etc.) resulting from the polymorphism contribute to BMT associated toxicity. As part of the BMT Life Study, citrulline and arginine levels were measured in 10 patients undergoing BMT.

High-dose chemotherapy used in BMT disrupts normal functions of urea cycle enzymes and contributes to either the occurrence of or toxicity associated with HVOD. To further evaluate this information, an analysis of stored plasma from ten patients undergoing BMT before treatment and after completion of induction chemotherapy was performed. Amino acid profiles were determined from all samples. Particular attention was paid to the urea cycle intermediates citrulline, arginine, and ornithine. As shown in Table 4, a marked decrease in citrulline levels of all patients from a pretreatment baseline mean of 24±3 μmol/L to a post-treatment mean of 8±1 μmol./L (P<0.001). Plasma arginine levels fell from a mean of 91±6 μmol./L to 70±6 μmol./L (P<0.05), despite the use of arginine-containing parenteral nutrition in several patients:

TABLE 4

| Amino Acid | Pre Chemo. | Post Chemo. | P Value |
| --- | --- | --- | --- |
| citrulline | 24 ± 3 uM | 8 ± 1 uM | <0.001 |
| arginine | 91 ± 6 uM | 70 ± 6 uM | 0.03 |

The fall in citrulline and arginine was similar in patients who did and did not receive total parenteral nutrition and was the same in males and females. The decreases in citrulline suggest that there is a decrease in flow through the first steps of the urea cycle (FIG. 1).

Thus, in accordance with the present invention, a method of reducing toxicity and/or the occurrence of HVOD in a patient undergoing BMT is provided. This method comprises administering the BMT patient arginine and/or citrulline, with citrulline being preferred, in an amount effective to bolster arginine and NO synthesis in the patient. The bolstering of arginine and NO synthesis in the patient reduces and/or substantially prevents the occurrence of HVOD associated with BMT. Citrulline is a preferred supplementation agent given that it is more readily converted to NO.

Example 4

Construction of a Functional Full-length CPSI Expression Clone

Figure 6:
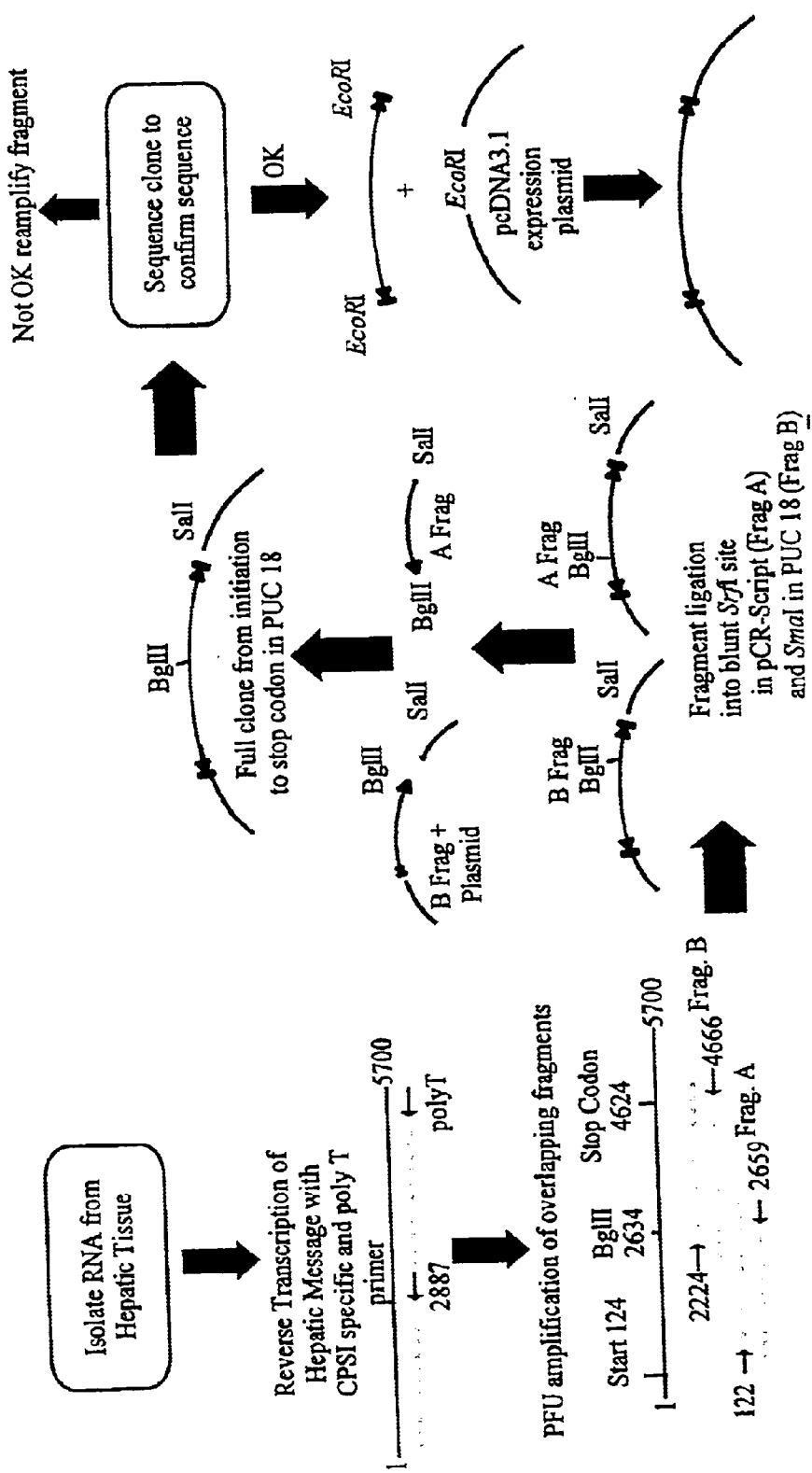
FIG. 6 is a schematic of a cloning strategy for a full length CPSI cDNA.
Figure 7:
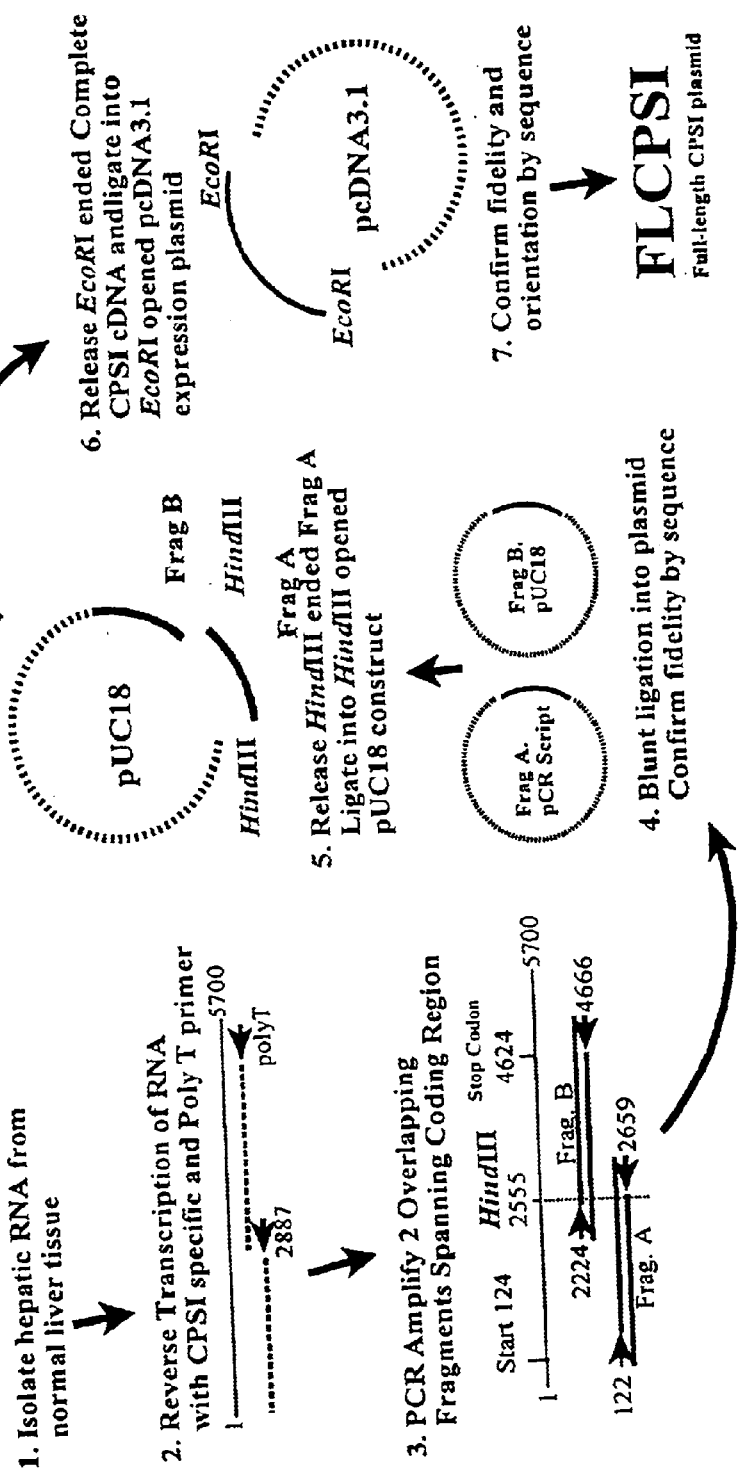
FIG. 7 is a schematic of an alternative cloning strategy for a full length CPSI cDNA.

After attempting a number of strategies, a human CPSI cDNA expression clone containing the entire coding region was constructed. FIGS. 6 and 7 present schematic diagrams illustrating the method used to construct the expression clone. This clone has been completely sequenced and does not contain any changes from the consensus CPSI sequence which has been characterized in the art.

The ability of the clone to make CPSI protein was tested in COS-7 cells. COS-7 cells were chosen for their lack of native CPSI activity or production. A western blot analysis of the COS-7 cells transfected with the flCPSI-PCDNA3.1 construct was prepared. HepG2 cell extracts were used as a control as these liver-derived cells have retained CPSI activity. Untransfected COS7 cells were used as a negative control. Unlike the untransfected COS-7 cells, the HepG2 and COS-7-flCPSI cells demonstrated the expected 160 kDa band using a rabbit anti-rat CPSI antibody. Additionally, a calorimetric assay was performed to detect the production of carbamyl phosphate from ammonia. As shown graphically in FIG. 8, the transected cells demonstrated activity similar to HepG2 cells while untransfected COS7 cells did not.

Site-directed mutagenesis has been performed on the T1405 containing CPSI insert and a copy with the N1405 polymorphic codon has been created. The N1405 polymorphic codon was sequenced for its entire length and no other changes were detected. The QuikChange™ (Stratagene) system, which takes advantage of the methylation introduced into DNA by host bacteria, was used to prepare this construct.

These constructs are used to provide a steady supply of recombinant CPSI protein as encoded by both alleles, (T1405, N1405) using COS cells and the respective CPSI/PC DNA 3.1 constructs as an expression system. Enzymatically active CPSI has been produced using this system, as shown by the graph in FIG. 8.

A component of these experiments is to determine the in vitro effect of the T1405N polymorphism on CPSI function. As discussed in Examples 1 and 2, this change affects the sensitivity of the enzyme to NAG concentrations. Screening of 20 individuals for the C to A change showed a heterozygosity rate of 50% with 25% of the group homozygous AA. This suggests that a significant portion of the general population has a potential qualitative abnormality in CPSI function. This abnormality, while silent under normal conditions, is unmasked by stressful conditions and toxins such as high-dose chemotherapy or valproic acid administration.

Comparison of the protein products is then done in stages. The first stage examines the physical characteristics of the expressed mRNA and protein. Using the flCPSI insert as a probe, Northern blots of message prepared from the expressing COS7 cell lines are probed. Positive controls include HepG2 and human liver message. Negative controls were COS-7 cells transfected with empty cassette pcDNA3.1. The expressed flCPSI derived message is somewhat smaller than the native CPSI (4.9 kb vs. 5.7 kb) since the clone does not contain the 1 kb 3' untranslated region.

Using the same controls, Western blot analysis of cell lysates by SDS-PAGE are performed. Comassie blue staining is used to examine total protein production. For specific CPSI detection, a polyclonal rabbit anti-rat CPSI antibody is used. This antibody detects the expressed CPSI from COS-7 cells as well as the control samples. Finally, changes in the protein's structure are determined by examining the mobility pattern by 2-D electrophoresis, a useful tool to detect conformational changes. Any large changes in confirmation likely explain the alteration in CPSI function for that mutation.

The next stage involves measuring the functional characteristics of the expressed enzymes. A sensitive calorimetric assay has been modified for this purpose (Pierson, D. L., *J. Biochem. Biophys. Methods*, 3:31–37 (1980)). The modified assay allows 4–5 analyses from 20–50 mg of tissue or cells. The tissue is first homogenized in 0.75M KCl. Small molecules, including ATP and NAG, are removed through a SEPHADEX™ G25 column (Boehringer). The reaction mix contains ammonium bicarbonate, ATP, magnesium DTT, n-acetylglutamate (NAG), and triethanolamine. The concentration of any reagent can be varied, and experiments on HepG2 cells show decreased activity with both low and high concentrations of NAG (0.50 mM). Absence of NAG in preliminary COS-7 cell expression experiments yields no measurable enzyme activity.

Figure 8:
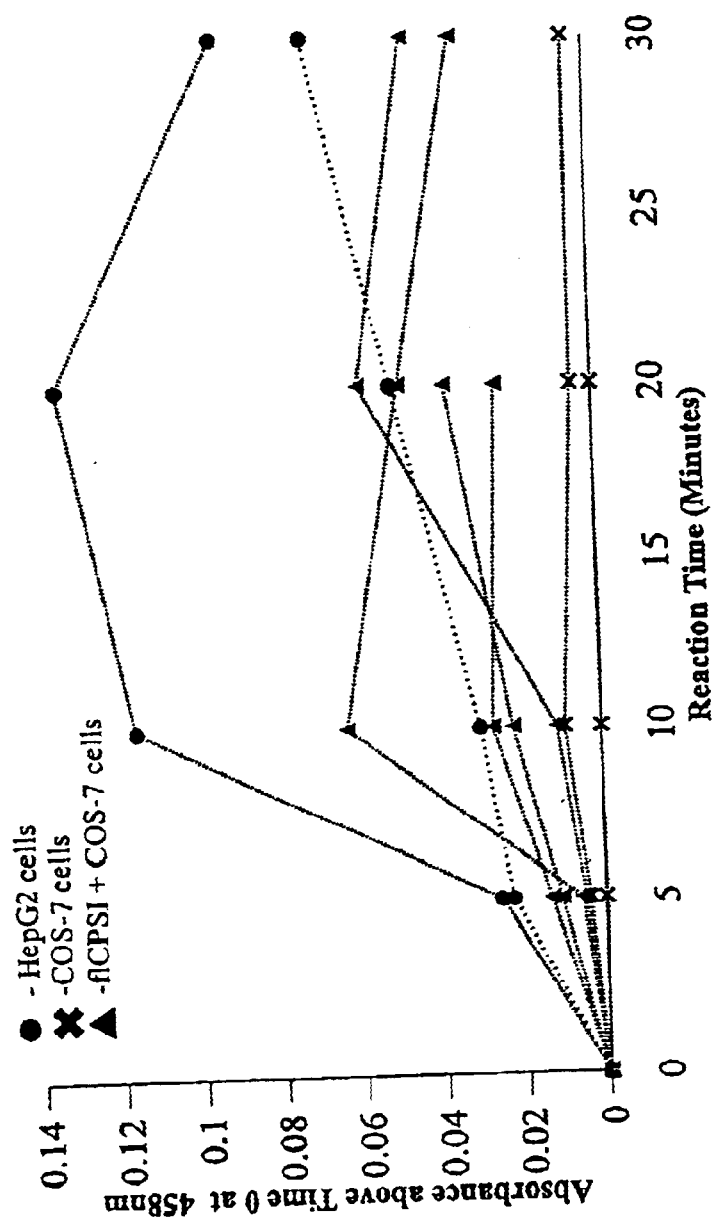
FIG. 8 is a graphical depiction of the metabolic activity of the CPSI protein expressed in COS-7 cells.

Since CPSI is an allosteric enzyme, it does not follow Michaelis-Menton kinetics under varying NAG concentrations; however, when the amount of NAG is fixed, the production of carbamyl phosphate is steady. As shown in FIG. 8, carbamyl phosphate production is measured by the addition of hydroxylamine to the solution after incubation at 37° C. for varying time periods (0, 5, 10, 20, 25, 30 minutes). This step, carried out at 95° C., also serves to inactivate the enzyme and prevent further production of carbamyl phosphate. The hydroxylamine converts the carbamyl phosphate to hydroxyurea which is subsequently treated with a sulfuric/acetic acid solution with butanedione to derive a compound with peak absorption at 458 nm. The reaction is then spun at 12,000×g for 15 minutes to remove precipitated protein. Next, the 458 nm absorbance is measured for each reaction. Activity typically begins to decrease after 20–30 minutes of reaction.

A number of expressing cell pellets are pooled for analysis. To ensure that activity measurements are based on consistent amounts of enzyme, expressed CPSI is quantified by Western blot analysis of the pooled sample using a CPSI antibody such as the rabbit anti-rat CPSI described hereinabove. Basal activity is first determined using fixed amounts of substrate and cofactor and a time course analysis. Varying amounts of ammonia bicarbonate, ATP, and NAG are then used to determine the binding efficiency for these elements. These elements are varied from 0 to 10fold the normal amount. Enzyme activity is also measured after heat treatment of the homogenate. Protein labeling (pulse-chase) experiments are performed to determine the stability of the protein over time.

Stable CPSI protein expression is obtained using the methods described above. The establishment of stable transfected cell lines allows the production of sufficient quantities of both varieties of CPSI to carry out these studies. In activity studies, changes in activity for the N1405 as compared to the T1405 type of CPSI are noted. A change in the enzyme activity under varying concentrations of NAG is also noted. These results support the role of this polymorphism of the present invention in predicting susceptibility to sub-optimal urea cycle function and hyperammonemia and decreased arginine production associated therewith.

Example 5

Relationship of the T1405N Polymorphism and Urea Cycle Intermediates to the Ammonia Elevation Seen in Patients on Valproic Acid Therapy Valproic acid (VPA) is a commonly used seizure medication, particularly for the treatment of absence seizures or as an adjunct therapy of other seizure disorders. Toxicity from VPA treatment is a complex and multi-variant process and probably reflects several metabolic disruptions. Hyperammonemia and hepatic micro-vesicular steatosis and necrosis are the most commonly reported serious medical complications.

Although the development of toxic hyperammonemia involves only a small number of patients, it carries a significant morbidity and mortality, and several deaths have been attributed to this complication. The development of asymptomatic hyperammonemia (plasma ammonia level greater than 60 $\mu$mol/L) occurs within one hour of VPA administration, and is, however, relatively common.

Mechanisms of VPA-induced Hyperammonemia. The mechanisms by which VPA causes hyperammonemia has been the subject of some debate, and a number of different theories currently have support in the art. A renal model proposed that the changed in glutamine metabolism resulted in an increased ammonia load to the liver, while most other theories concentrate on different aspects of urea cycle function. See, for example, Warter et al., *Revue Neurologique*, 139:753–757 (1983). Since the urea cycle is the major mechanism for the removal of ammonia in humans, it is thought that hyperammonemia arises in some way from the inhibitory interactions of VPA and/or its metabolites with urea cycle function and capacity.

Evidence for urea cycle dysfunction in VPA therapy comes from a number of experimental and clinical observations aside from elevations in plasma ammonia described above. For example, Marrini et al. measured a reduction in both baseline and stimulated CPSI activity in nonnephrectomized animals following an amino acid and VPA load (Marrini et al., *Neurology* 38:365–371 (1988)). Marrini et al. also observed that nephrectomized rats injected with an amino acid load and VPA also developed hyperammonemia. Another group, Castro-Gago et al., measured serum amino acids in 22 epileptic children treated with VPA, and found reduction in aspartic acid and ornithine, implicating a decrease in urea cycle efficiency rather than an increase in precursors (Castro-Gago et al., *Childs Neurons System* 6:434–436 (1990)).

Significance of Carbamyl Phosphate Synthase I. Mechanisms of VPA-induced urea cycle deficits typically revolve around mitochondrial carbamyl phosphate synthetase I (CPSI). A patient with severe toxicity following VPA overdose was found to have 50% normal CPSI activity (Bourrier et al., *Prese Medicale* 17:2063–2066 (1988)). Applicants have observed several mild CPSI deficient patients who deteriorated when given valproic acid with ready reversal after discontinuation.

Role of NAG. N-acetylglutamate (NAG) is a required allosteric cofactor for CPSI. NAGA is synthesized from glutamate and acetyl CoA in mitochondria, with a cellular distribution that mirrors that of CPSI (Shigesada et al., *Journal of Biological Chemistry* 246: 5588–5595 (1971)). It is synthesized from glutamate (from amino acid catabolism) and acetyl CoA. There are several ways in which an alteration of NAG availability is envisaged to reduce the activity of CPSI. Genetic deficiencies in NAG synthetase have been observed, and this enzyme is known to be inhibited competitively by alternate substrates such as propionyl CoA or succinate (Bachmann et al., *New England Journal of Medicine* 304:543 (1981); Kamoun et al., *Lancet* 48 (1987); Coude et al., *J. Clin. Invest.* 64:1544–1551 (1979); Rabier et al., *Biochem. And Biophys. Research Comm.* 91:456–460 (1979); Rabier et al., *Biochimie* 68:639–647 (1986)). It has been shown experimentally that CPSI is inhibited in a competitive manner by the presence of increased amounts of propionyl CoA, and that VPA therapy causes an increase in blood propionate concentration (Coulter et al., *Lancet* 1 (8181): 1310–1311 (1980); Gruskay et al., *Ped. Res.* 15:475 (1981); Schmidt, R. D., *Clin. Chim. Acta*, 74:39–42 (1977)). VPA exposure has also been shown to decrease NAG concentrations in intact hepatocytes, by decreasing concentrations of both acetyl CoA and glutamine (Coude et al., *Biochem. J.* 216:233–236 (1983)). The decrease in glutamine concentration is attributed to inhibition of both pyruvate dehydrogenase and pyruvate carboxylase.

Alternatively, it has been suggested that depletion of mitochondrial acetyl CoA occurs because CoA is diverted on VPA therapy for the manufacture of valproyl CoA (Becker et al., *Archives of Biochemistry & Biophysics* 223:381–392 (1983)). It is well known that VPA also disrupts fatty acid β-oxidation, with resultant diminution of acetyl CoA (Eadie et al., *Med. Toxicol.* 3:85–106 (1998)). All these mechanisms could lead to a shortage in NAG since it is synthesized from acetyl CoA. Given the effects of VPA on NAG availability it follows that any change in the binding properties of CPSI for NAG would affect its activity.

Thus, this Example sets forth experimentation for determining correlation between the presence or absence of the polymorphism of the present invention in the CPSI gene with susceptibility to hyperammonemia using VPA as a model agent for the production of hyperammonemia. Initially, genomic DNA is isolated from patients who are beginning valproic acid therapy for genotyping for the T1405N polymorphism in accordance with the methods described herein, such as PCR amplification and use of non-denaturing gels. After genotyping these patients, pre- and post-treatment amino acid and ammonia determination is performed for these patients. Particularly, DNA is isolated from whole blood using the QIAmp™ (Qiagen) kit described in Example I.

Next, plasma total VPA concentration is determined by an enzyme-mediated immunoassay technique (EMIT™ Syva-Behring, San Jose, Calif. on a Syva 30R™ analyzer). This technique utilizes competitive binding for VPA antibody binding sites between VPA in the patient plasma and that complexed with the enzyme G6PDH. Release of the VPA enzyme complex from the antibody reactivates the enzyme, and its activity is assessed by the rate of formation of NADH upon addition of the substrate. NADH production is monitored via spectroscopy at 340 nanometers (nm). Free (non-protein bound) VPA is isolated from plasma using a centrifugal micro partition filter device with a 3000 Dalton cut-off (CENTRIFREE™, Aimcon, Beverley, Mass.). The VPA concentration in the plasma ultra filtrate is measured as described for total VPA.

Data collected from VPA patients is analyzed for correlations between genotype and phenotype. Additionally, free and conjugated VPA fractionation are compared to evaluate effects on NAG production and availability. The latter comparison is prepared given that there are known effects of VPA on NAG availability. For example, VPA exposure has been shown to decrease NAG concentrations in intact hepatocytes by decreasing concentrations of both acetyl CoA and glutamine. See Coude et al., *Biochem. J.*, 216:233–236 (1983). Thus, this comparison reflects that changes in the binding properties of CPSI for NAG affect the activity of CPSI.

Example 6

Detection of Additional Polymorphisms in CPSI

Using the techniques developed for mutation analysis of CPSI message, 10 non-CPSI deficient, unrelated patients are screened for additional polymorphisms in the coding region. This is done using "illegitimate" transcripts from lymphoblastoid and fibroblast cell lines. Polymorphisms with a widespread effect on the population should be evident in this size sample. As used herein and in the claims, the term "polymorphism" refers to the occurrence of two or more genetically determined alternative sequences or alleles in a population. A polymorphic marker is the locus at which divergence occurs. Preferred markers have at least two alleles, each occurring at frequency of greater than 1%. A polymorphic locus may be as small as one base pair. Provided polymorphic markers thus include restriction fragment length polymorphisms, variable number of tandem repeats (VNTR's), hypervariable regions, minisatellites, dinucleotide repeats and tetranucleotide repeats.

Figure 3:
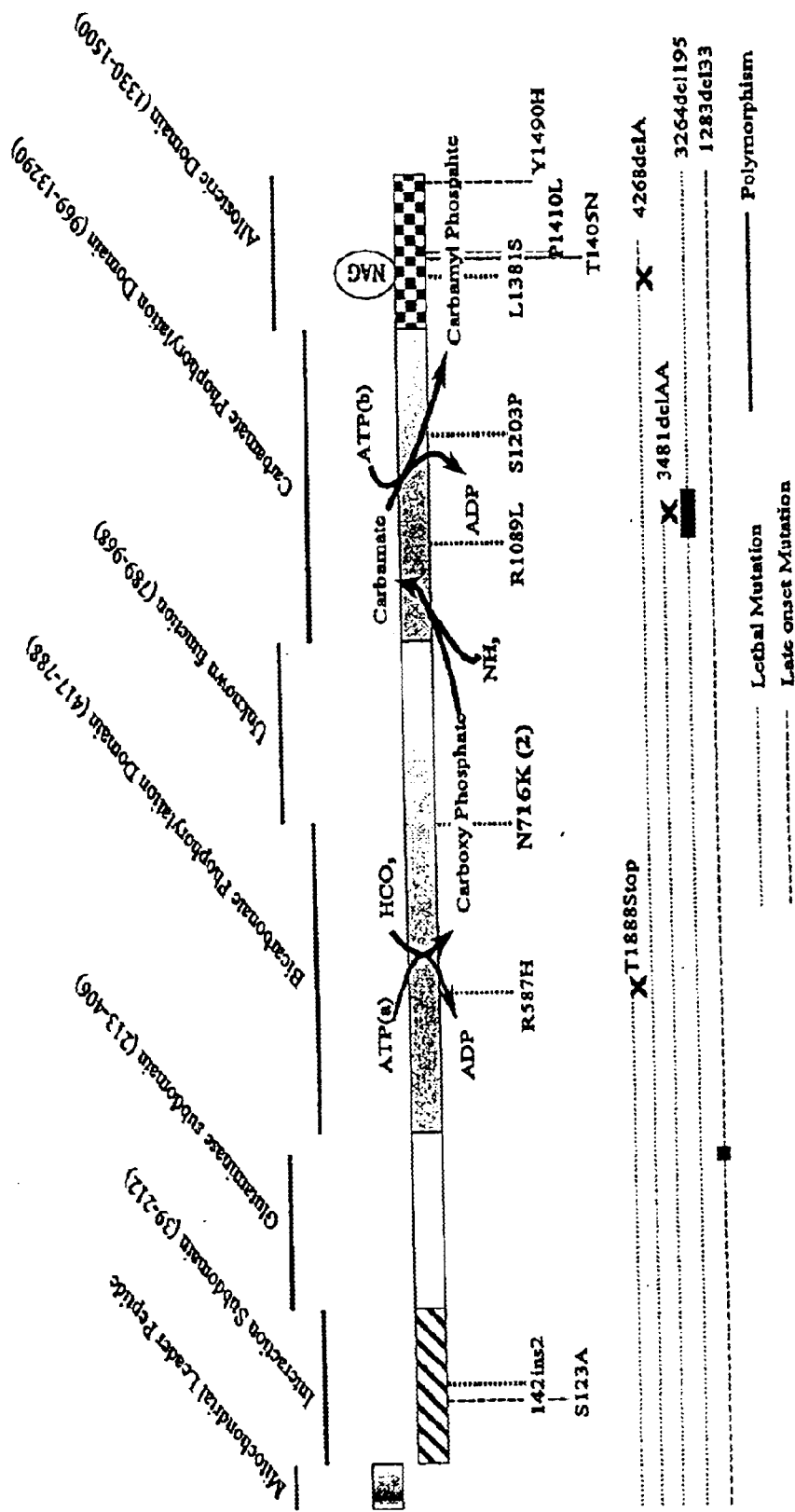
FIG. 3 is a schematic of the consensus CPSI protein depicting several known mutations in the protein and depicting the T1405N polymorphism of the present invention.

A number of "mutation" detection techniques have been carried out, all of which are based on detectable changes in the mobility of non-denatured single-stranded DNA, as described by Summar, M., *J. Inherited Metabolic Disease* 21:30–39 (1998). Examples of CPSI mutations identified by these techniques are disclosed in FIG. 3. Due to the large size of the CPSI message (about 5,700 bases) a method to screen a large amount of DNA in a few reactions is preferred. Restriction endonuclease fingerprinting (REF) provides for the screening large DNA fragments, up to about 2,000 bp, with excellent sensitivity.

Reverse transcriptase reactions (RT) are carried out using 1 µg of total RNA and either an oligo-dT primer or an antisense primer from the midpoint of the CPSI message. Using the RT product as template, PCR reactions are performed with 4 different primer sets creating 4 overlapping fragments spanning the 4,600 base coding region. Control PCR reactions are run with each set of experiments, to ensure that contaminating template is not amplified. Genomic DNA is not preferred for this study due to the size of the gene (80,000+ bp), the number of introns (36), and that sequencing of the intron exon boundaries for CPSI has not been completed. However, intronic locations are characterized graphically in FIG. 9.

The 4 overlapping RT/PCR products described above are used for mutation screening. Careful analysis of the restriction maps leads to the selection of three restriction enzymes for each fragment which cleave them into pieces ranging from 100–250 bp. Fragments of this size are ideal for single strand conformation polymorphism (SSCP) analysis. The enzymes are selected such that each fragment can be evenly evaluated across its length.

Prior to digestion, the PCR products are purified by gel electrophoresis and isolation from the agarose slices. After 3 hours, the digested fragments are ethanol precipitated. These fragments are separated in a 6% non-denaturing polyacrylamide gel at 4° C. running at a constant 35 watts. These conditions maximize the detection of conformational changes in the single stranded fragments, as described by Liu, Q. and Sommer, S. S., *Biotechniques* 18(3):470–477 (1995). DNA detection is done by silver staining and the gels are scored for mobility shifts. Based on the location of any shifted fragment, direct sequence analysis of the RT/PCR product is performed using a cycle-sequencing protocol. To eliminate the possibility of a mutation resulting from Taq polymerase errors, a fresh RT product is amplified and sequenced in each case. The entire 4,600 bases of coding message is rapidly screened in this fashion Any regions containing unclear areas are sequenced, looking for changes in the expected sequence.

The restriction digestion products of each RT/PCR fragment are isolated. These individual fragments are then run against the combined digestion in a non-denaturing gel as described above. By characterizing the fragment pattern in this way, the portions of the CPSI message involved in any observed mobility shifts are readily identified.

Polymorphisms detected in these experiments are genotyped against the Centre d'Etude Polymorphsim Humanise (CEPH) parents panel to establish frequency. All changes are examined for their effect on codon use and those resulting in mis-sense mutations are examined using the CPSI characterization data disclosed herein.

The techniques described in Example 3 are used to express site-directed mutants containing these changes. Using this system the in vitro effects of the changes on CPSI production and activity are observed.

A T344A polymorphism was detected in CPSI. Oligonucleotide primers were used from the 10th exon (U1119:tactgctcagaatcatggc—SEQ ID NO:17) and intron (LI10+37: tcatcaccaactgaacagg—SEQ ID NO:18) to amplify a 91 bp fragment containing the change. PCR cycle conditions were: 35 cycles of 1 minute anneal at 59° C., 1 minute extension at 72° C., and 1 minute denaturation at 94° C. Patients were classified as having either homozygous SNP genotypes of AA or TT, or as being heterozygous (AT). The adult population distribution of this polymorphism is 35% AA, 44% AT, and 21% TT.

A 118-CTT polymorphism was also detected in CPSI. Oligonucleotide primers were used from the 5' untranslated region (U5'-74: ggttaagagaaggaggagctg—SEQ ID NO:19) and intron (L175: aaccagtcttcagtgtcctca—SEQ ID NO:20) to amplify a 249 bp fragment containing the change. PCR cycle conditions were: 35 cycles of 1 minute anneal at 59° C., 1 minute extension at 72° C., and 1 minute denaturation at 94° C. Patients were classified as having either a homozygous genotype with the 118 trinucleotide insertion or deletion, or as being hetermzygous. The adult population distribution of this polymorphism is 34% CTT−, 43% hetermzygous, and 23% CTT+.

Example 7

Biochemical and Genetic Alterations in Carbamyl

Phosphate Synthetase I in Neonatal Patients With With Persistent Pulmonary Hypertension This Example investigates the role of the limitation of endogenous NO production in the pathogenesis of persistent pulmonary hypertension (PPHN) in the sick term neonate. Endogenous NO is the product of the urea cycle intermediate arginine. Production of arginine depends on the rate-determining enzyme of the urea cycle, carbamyl phosphate synthetase (CPSI). Newborns possess less than half the normal urea cycle function making them particularly susceptible to minor changes in enzyme form and function. A common exonic polymorphism (T1405N) in CPSI has been observed which affects flow through the first step of the urea cycle.

In this Example, it was tested whether newborns who developed PPHN would have lower NO precursors (arginine and citrulline) than matched controls. Whether PPHN patients have predominantly the CC (threonine/threonine) or AC (asparagine/threonine) CPSI genotypes which are associated with lower function than AA (asparagine/asparagine) CPSI genotype was also analyzed.

Methods. Forty-seven neonates >2 kg, >35 weeks, and <72 hours old who were admitted to the Vanderbilt Neonatal Intensive Care Unit with (n=22) and without (n=25) echocardiographically-documented pulmonary hypertension were enrolled. Clinically important measures of the severity of respiratory distress were recorded. Ammonia levels and plasma amino acid profiles were obtained. Genotypes were determined by running PCR-amplified DNA on nondenaturing MDE™ gels.

Results. Patients who developed PPHN had an average arginine of 21.5 µmol/l while those who did not averaged 38.3 µmol/l (p=0.0004). The citrulline averages were 6.1 µmol/l and 10.3 µmol/l respectively (p=0.02). The levels of arginine and citrulline were inversely correlated with the severity of hypoxemia as measured by oxygenation index, days of mechanical ventilation, and days requiring supplemental $O_2$. Genotype analysis of PPHN patients for T1405N showed 5CCs. 17ACs, and 0AAs, whereas the controls had 7CCs, 16ACs, and 2AAs (Chi-square p=0.005 using the expected population allele frequency). Infants with the CC genotype had lower arginine and citrulline means (21.5 umol/l and 5.8 umol/l) than infants with the AA genotype (31.5 umol/l and 13.5 umol/l) consistent with a functional difference between the two forms of the enzyme.

Conclusions. This Example shows that the development of PPHN in sick newborns is associated with inadequate availability of the urea cycle intermediates arginine and citrulline. The T1405N polymorphism in the CPSI DNA leads to diminished enzyme function and subsequent lower levels of NO precursors.

Discussion. Carbamyl phosphate synthetase (CPSI) catalyzes the rate-determining step in the urea cycle thereby determining tissue levels of the urea cycle intermediates including arginine and citrulline. As disclosed herein, a widely distributed C to A exonic polymorphism in the CPSI gene changes a conserved threonine to an asparagine at position 1405 near the critical N-acetyl glutamate binding domain. Data has shown that the asparagine containing version of CPSI displays more efficient kinetics in enzyme function studies.

The T1405N allele exhibits 50% heterozygosity and appears to be a silent variant in normal healthy adults. However, consequences of the qualitative change can be unmasked by stressful conditions. As disclosed in Examples 1–3, adults exposed to high-dose chemotherapy in preparation for bone marrow transplantation that the threonine-containing enzyme produces inadequate levels of arginine and citrulline and is associated with an increased incidence of hepatic veno-occlusive disease, acute lung injury, and death. As nitric oxide (NO) is generated in endothelial cells from L-arginine by nitric oxide synthetase (NOS), decreased levels of urea cycle intermediates could predispose to disturbances in vascular tone by limiting endogenous NO production.

In the prospective cohort study of this Example, the possibility that a similar process could be involved in the pathogenesis of persistent pulmonary hypertension of the newborn (PPHN) was investigated. Endogenously produced NO functions in regulation of pulmonary vascular resistance and in the transition from fetal to neonatal circulation. Lipsitz, E. C., et al. *J Pediatr Surg* (1996)31:137–140; Abman, S. H., et al. *Am J Physiol* (1990)259:H1921–H1927. Between 20 weeks gestation and term birth, CPSI production and function are less than 50% of adult levels. This physiologic deficiency could unmask the effect of the T1405N gene mutation particularly if coupled with other neonatal stresses affecting hepatic function; for instance, asphyxia or sepsis.

Patients eligible for this study included appropriately grown neonates ≧35 weeks gestation and ≧2 kg birthweight who were admitted to the Vanderbilt University Medical Center neo-natal intensive care unit (NICU) between Jul. 1, 1999 and Feb. 29, 2000 for symptoms of respiratory distress. Infants with multiple congenital anomalies, known genetic syndromes, and anatomic causes of pulmonary hypertension (congenital diaphragmatic hernia, Potter's syndrome, asphyxiating thoracic dystrophy, etc.) were excluded. Parental consent was obtained for all enrollees. Fifty-one neonates had 3 cc of blood drawn in the first 72 hours of life for plasma amino acid profiles, ammonia and BUN levels, nitric oxide metabolite determination, and CPS1 genotyping. Blood was drawn prior to blood transfusion, enteral or parenteral protein intake, inhaled nitric oxide administration, or ECMO cannulation.

Data collected on the enrollees included (1) baseline characteristics (birthweight, gestational age, sex, race, Apgar scores, primary diagnosis, any pulmonary complications, and the postnatal age at the time blood was drawn) and (2) measures of respiratory support ($FiO_2$, MAP, iNO, ECMO) and clinical response (ABGs, duration of mechanical ventilation and supplemental $O_2$, survival.) Maximum oxygenation index [$OI=FiO_2 \times MAP/PaO_2$] was used as a measure of the severity of respiratory distress. Predominant primary diagnoses included (1) birth asphyxia: 5-minute Apgar score <5 with a mixed acidosis on first ABG or cord blood gas plus evidence or neurologic dysfunction and other end-organ injury, (2) respiratory distress syndrome (RDS): clinical symptoms of respiratory distress with ground-glass lung fields and air bronchograms on chest X-ray plus combined hypercarbia/hypoxia on ABG (Note: given the gestational age of these neonates, infants with this picture could have had either surfactant-deficiency or congenital pneumonia; however, in no case was a positive tracheal aspirate culture obtained), and (3) meconium aspiration syndrome (MAS): history of meconium-staining at delivery plus clinical symptoms of respiratory distress, hypoxemia, and coarse infiltrates chest X-ray.

Infants were defined as having pulmonary hypertension (PPHN) if they developed significant hypoxemia ($PaO_2$<100 on 100% $O_2$>6 hours) with normal intracardiac anatomy and echocardiographic evidence of elevated pulmonary artery pressure. The latter was defines as (1) right-to-left or bidirectional ductal of foramen ovale flow or (2) elevated (>35 mmHg) pulmonary artery pressure based on Doppler estimate of the tricuspid regurgitation jet as read by a blinded third party.

Amino acid analysis was performed on fresh plasma samples in 47 patients. A protein free extract of plasma was prepared by protein precipitation with sulfosalicylic acid and filtration through a 0.45 um Acrodisc 4 (Gelman Sciences, Ann Arbor, Mich.). Amino acids were separated by cation exchange chromatography using a four-component pH- and ionic strength-graded lithium citrate buffer system on a Beckmann 7300 amino acid analyzer (Beckmann, Palo Alto, Calif.). Post column derivatization of amino acids with ninhydrin allowed detection of primary amine amino acids at 570 nm, and secondary amines at 440 nm. Quantitation was achieved by instrument calibration with standard reference materials (Sigma, St. Louis, Mo.). Citrulline and arginine were detected as measurable indices of flux of intermediates through the urea cycle.

Measurement of plasma nitric oxide metabolites ($NO_x$). Plasma $NO_x$ was measured in a subgroup of patients using modified Griess reagents after samples were deproteinated and incubated with cadmium beads to convert nitrate to nitrite.

SNP Detection. Oligonucleotide primers from within the $36^{th}$ exon (U4295—SEQ ID NO:15) and intron (LI36—SEQ ID NO:16) of CPS1 and the polymerase chain reaction (PCR) to reliably amplify a 251 bp fragment encompassing the region containing the change from genomic DNA obtained from whole blood preparations. This combination of primers gave reproducible amplification using Taq polymerase (Promega) and PCR cycle conditions as follows: 35 cycles of 1 minute anneal at 67° C., 1 minute extension at 72° C., and 1 minute denaturation at 94° C. After formamide treatment, samples were subjected to electrophoresis for 5 hours at 4° C. in a non-denaturing MDE™ gel (FMC, Rockland, Me.), then stained with silver nitrate to detect DNA fragments. Patients were classified as having homozygous SNP genotypes of CC or AA, or as being heterozygous (AC). Genotyping using nondenaturing gel electrophoresis and direct sequence analysis yielded identical results as those disclosed above. Thus, the adult population distribution of the T1405N polymorphism was determined to be: 45% CC, 44% AC, and 11% AA.

An identical technique to that described above was used to detect the T344A polymorphism. Oligonucleotide primers were used from the 10th exon (U1119:tactgctcagaatcatggc—SEQ ID NO:17) and intron (LI10±37:
tcatcaccaactgaacagg—SEQ ID NO:18) to amplify a 91 bp fragment containing the change. PCR cycle conditions were: 35 cycles of 1 minute anneal at 59° C., 1 minute extension at 72° C., and 1 minute denaturation at 94° C. Patients were classified as having either homozygous SNP genotypes of AA or TT, or as being heterozygous (AT). The adult population distribution of this polymorphism is 35% AA, 44% AT, and 21% TT.

An identical technique to that described above was used to detect the 118-CTT polymorphism. Oligonucleotide primers were used from the 5' untranslated region (U5'-74: ggttaagagaaggaggagctg—SEQ ID NO:19) and intron (L175: aaccagtcttcagtgtcctca—SEQ ID NO:20) to amplify a 249 bp fragment containing the change. PCR cycle conditions were: 35 cycles of 1 minute anneal at 59° C. 1 minute extension at 72° C., and 1 minute denaturation at 94° C. Patients were classified as having either a homozygous genotype with the 118 trinucleotide insertion or deletion, or as being heterozygous. The adult population distribution of this polymorphism is 34% CTT–, 43% heterozygous, and 23% CTT+.

Ammonia and plasma amino acid levels were compared between groups of patients using Students T-test. Distributions of genotypes of CPSI were compared across groups by calculating allelic frequency for the entire group and searching for evidence of Hardy-Weinberg disequilibrium in specifically selected subgroups using Chi-square analysis. Of the 51 neonates originally enrolled, 25 developed PPHN while 26 did not. There were no statistically significant differences in the baseline characteristics of the two groups including birthweight, gestational age, race, or the postnatal age in hours of the infants at enrollment. There was, however, a slight predominance of males in the control group.

The distribution of primary diagnoses was evenly distributed. In the PPHN group, 5 infants had birth asphyxia, 9 infants had RDS, 5 infants had meconium aspiration syndrome, and 6 infants had other diagnoses, including 4 infants with primary PPHN. In the control group, 4 infants had birth asphyxia, 8 infants had RDS, 3 infants had MAS, and 11 infants had other diagnoses. The other diagnoses included supraventricular tachycardia, anemia, birth trauma, and viral sepsis. No infant in the study had a positive bacterial blood culture.

As expected, infants who had PPHN complicate their primary pathology did develop more severe illness than the controls by some clinical criteria. Eight of the infants with PPHN required treatment with inhaled NO (iNO), 2 required ECMO, and 2 died (one infant with asphyxia and multiorgan-system failure on iNO; another infant with alveolar capillary dysplasia was withdrawn from ECMO.) Obviously, none of the controls were treated with iNO or ECMO; and there was no mortality in the control group.

Three infants in the PPHN group were excluded from analysis. The infant found to have alveolar capillary dysplasia on lung biopsy was considered to have an anatomical etiology for pulmonary hypertension. Another infant was mistakenly enrolled with a congenital diaphragmatic hernia, and the third was enrolled at 119 hours of age after TPN had been initiated. One infant in the control group was excluded from analysis after karyotype analysis revealed the etiology of his hypotonia to be Prader-Willi syndrome.

The infants who developed PPHN had significantly lower serum arginine and citrulline levels on amino acid analysis. The mean arginine level in PPHN cases was 21.5±9.2 umol/l whereas the mean arginine of the control group was 38.3±18.4 umol/l (p=0.0004). The mean citrulline in PPHN cases was 6.1±3.6 umol/l compared to 10.3±7 umol/l in the control group (p=0.02). There were no significant differences in the levels of other amino acids between the two groups, including glutamine, glycine, alanine, lysine, valine, ornithine, and leucine. The level of total essential amino acids (TEAA) was slightly lower in the PPHN cases, about 537 umol/l versus about 654 umol/l, but this difference was not statistically significant (p=0.08), by birthweight, gestational age, or number of hours of postnatal life. The level of TEAA was found to be significantly higher in the four infants whose blood was drawn prior to six hours of age (about 1021.5 umol/l vs. about 542 umol/l, p=0.0026). This difference is presumed to reflect the recent cessation of parenteral protein influx in these infants from the placental circulation.

No differences in arginine and citrulline levels were found when the primary diagnosis categories of asphyxia, RDS, MAS, and "other" were separately analyzed. In each group, infants with pulmonary hypertension tended to have lower values, but the results were not statistically significant given the small numbers of infants in each group. For example, asphyxiated infants with PPHN had a mean arginine of about 18.5 umol/l compared to about 52.7 umol/l in asphyxiated controls (p=0.06) and a mean citrulline of about 6.8 umol/l compared to about 14.3 umol/l (p=0.04).

There was an inverse relationship between the levels of serum arginine and citrulline and the severity of hypoxemia. Arginine and citulline values fell progressively as oxygenation index increased, days of mechanical ventilation increased, and days requiring supplemental oxygen increased birthweight, gestational age, or number of hours of postnatal life. The $NH_3$ levels in infants with PPHN tended to be slightly higher than in controls (54±18.1 $\mu$mol/l vs. 45.6±12 $\mu$mol/l) but these values were not statistically significant (p=0.08). On CPS1 T1405N genotype analysis, of the 22 infants who developed PPHN, 5 were CC and 17 were AC. There were no AAs in the PPHN cases. In the 25 controls, there were 7 CCs, 16 ACs, and 2 AAs. These distributions of genotypes were then compared by calculating the expected allelic frequency for the entire group revealing evidence of Hardy-Weinberg disequilibrium in the PPHN group. On Chi-square analysis these two groups are significantly different from each other with a p-value=0.005. Of the two infants with the AA genotype, one infant had RDS while the other suffered from birth asphyxia. Neither infant ever achieved an OI ±15; both spent <1 week on the ventilator and <10 days on oxygen.

Infants with the CC genotype had mean arginine levels of 21.9±7 umol/l and citrulline levels of 5.8±1.8 umol/l while infants with the AA genotype had a mean arginine level of 31.5±3.5 umol/l and a mean citrulline level of 13.5±6.4 umol/l. Again, given the small number of AAs, this data has difficulty reaching statistical significance with p-values of 0.1 and 0.006, respectively.

REFERENCES

The references listed below as well as all references cited in the specification are incorporated herein by reference to the extent that they supplement, explain, provide a background for or teach methodology, techniques and/or compositions employed herein.

Abman, S. H., et al., *Am J Physiol* (1990) 259 H1921–H1927.
Adelman et al., *DNA* 2:183 (1983).
Alonso, E. and Rubio, V., *European Journal of Biochemistry* 229:377–384 (1995).
Artymiuk, P. J. et al., *Nature Struct. Biol.* 3:128–132 (1996).
Bachmann et al., *New England Journal of Medicine* 304:543 (1981).
Batshaw M L, Brusilow S W. *Annals of Neurology* 1982; 11:319–21.
Bearman S I, *Journal of Clinical Oncology* 1993; 11:1729–36.
Beaucage et al., *Tetrahedron Letters* 22:1859–1862 (1981).
Beaumier L, *Biomedical & Environmental Sciences* 1996; 9:296–315.
Becker et al., *Archives of Biochemistry & Biophysics* 223:381–392 (1983).
Bernard G R, Artigas A, Brigham K L, et al. *Intensive Care Medicine* 1994; 20:225–32.
Blau N. Duran, M., and Blaskovics, M. E. *Physician's Guide to the Laboratory Diagnosis of Metabolic Diseases* London: Chapman&Hall Medical, 1996.
Bourrier et al., *Prese Medicale* 17:2063–2066 (1988).
Castillo, L., et al., *Pediatr Res* (1995) 38:17–24.
Castillo L, et al., *Journal of Biological Chemistry* 1989; 264:4038–44.
Castro-Gago et al., *Child Neuro Systems* 6:434–436 (1990).
Cervera. J. et al., *Biochemistry* 35:7247–7255 (1996).
Cohen P P. *Current Topics in Cellular Regulation* 1981; 18:1–19.
Coude et al., *Biochem. J.* 216:233–236 (1983).
Coude et al. *J. Clin. Invest.* 64: 1544–1551 (1979).
Coulter et al., *Lancet* 1 (8181): 1310–1311 (1980).
Crea et al., *Proc. Natl. Acad. Sci. USA* 75:5765 (1978).
Davies et al., *Bone Marrow Transplantation* 17:1119–1125 (1996).
de Groot, C. J., et at., *Biochemical & Biophysical Research Communications* 124:882–888 (1984).
Eadie et al., *Med. Toxicol.* 3:85–106(1998).
Eichenlaub et al., *J. Bacteriol.* 138:559–566 (1979).
Faber-Langendoen K, et al. *Bone Marrow Transplantation* (1993) 12:12501–7.
Gribskov et al., *Nucl. Acids. Res.* 14:6745 (1986).
Gruskay et al., *Ped. Res.* 15:475 (1981).
Guillou, F., et al. *Proc Natl Acad Sci* 86:8304–8308 (1989).
Guy, H. I. et al., *Journal of Biological Chemistry* 270:2190–2197 (1995).
Hauser E R, et al., *New England Journal of Medicine* 1990; 322:1641–5.
Hebert P C, *Chest* 1993; 104:230–5.
Howell et al., *Antibodies A Laboratory Manual* Cold Spring Harbor Laboratory, (1988).
Jackson, M. J. et al., *Annual Review of Genetics* 20:431–464 (1986).
Jackson M J, *Annual Review of Genetics* 1986; 20:431–64.
Javid-Majd et al., *Biochemistry* 35:14362–14369 (1996).
Jones R J, et al. *Transplantation* 1987; 44:778–83.
Kamoun et al., *Lancet* 48 (1987).
Kinsella, J. P., et al., *Lancet (*1992) 340:819–820.
Kyte & Doolittle, *J. Mol. Biol.* 157:105–132 (1982).
Lagace, M. et al., *Journal of Biological Chemistry* 262:10415–10418 (1987).
Lipsitz, E. C., et al. *J Pediatr Surg* (1996) 31:137–140.
Liu, Q. and Sommer, S. S., *Biotechniques* 18(3):470–477 (1995).
Maniatis et. al. in *Molecular Cloning: A Laboratory Manual*, Cold Spring Harbor, N.Y., p 280–281 (1982).
Marrini et al., *Neurology* 38:365–371(1988).
Marshall J C, et al., *Critical Care Medicine* (1995) 23:1638–52.
Matuschak, G. M., *Clinics in Chest Medicine* (1996) 17:83–98.
Matuschak, G. M. and Rinaldo, J. E., *Chest* (1988) 94:400–6.
Matuschak et al., *American Review of Respiratory Disease* 1990; 141:1296–306.
McCaffrey, M. J., et al., *Biol Neonate* (1995) 67:240–243.
McDonald, G. B., et al., *Annals of Internal Medicine* 1993; 118:255–67.
Meister, A., *Adv. Enzymol. Relat. Areas Mol. Biol.* 62:315–374 (1989).
Messing et al., *Third Cleveland Symposium on Macro Molecular and Recombinant DNA* Ed. Walton, A., (Elsevier, Amsterdam) (1981).
Mitchell R B, Wagner J E, Karp J E, et al. *American Journal of Medicine* 1988; 85:662–7.
Mitchell et al., *Amer. J. Med.*85:662–667 (1988).
Moncada S. Higgs A. *New England Journal of Medicine* 1993; 329:2002–12.
Moorman, A. F. et al. *Histochemical Journal* 22:457–468 (1990).
Needleman et al., *J. Mol. Bio.* 48:443 (1970).
Nuzum, C. T. and Snodgrass, P. J., *Science* 1971; 172:1042–3.
Nyunoya, H., et al., *Journal of Biological Chemistry* 260:9346–9356 (1985).
Palmer R M J, et al., *Biochem Biophys Res Commun* (1988) 153:1251–1256. *PCR. A Practical Approach*, ILR Press, Eds. McPherson, et al. (1992).
Pierson, D. L., *J. Biochem. Biophys. Methods* 3:31–37 (1980).
Price, K. J., et al., *American Journal of Respiratory & Critical Care Medicine* 1998; 158:876–84.
Rabier et al., *Biochem. & Biophys. Research Comm.* 91:456–460 (1979).
Rabier et al., *Biochimie* 68:639–647 (1986).
Raiha, N. C. R. and Suihkonen, J. *Acta Paediatrica Scand* 57:121–127 (1968).
Richardson, P. and Bearman, S. I., *Leukemia & Lymphoma* (1998) 31:267–77.
Rinaldo J E, et al., *American Journal of Respiratory Cell & Molecular Biology* 1994; 11:625–30.
Roberts, J. D., et al., *Lancet* (1992) 340:818–819.
Rodriguez-Aparicio, L. B. et al., *Biochemistry* 28:3070–3074 (1989).
Rubenfeld G D, Crawford S W. *Annals of Internal Medicine* 1996; 125:625–33.
Rubio, V., (Review) Biochemical Society *Transactions* 21:198–202 (1993).
Rubio, V. and Grisolia, S., *Enzyme* 26:233–239 (1981).
Saiki et al., *Bio/Technology* 3:1008–1012 (1985).
Sambrook et al., *Molecular Cloning: A Laboratory Manual* (Cold Spring Harbor Press, Cold Spring Harbor, N.Y.) (1989).
Schmidt, R. D., *Clin. Chim. Acta.* 74:39–42 (1977).
Schwartz et al., eds., *Atlas of Protein Sequence and Structure*, National Biomedical Research Foundation, pp. 357–358 (1979).
Shulman H M, et al., *Hepatology* 1994; 19:1171–81.
Smith et al., *Adv. Appl. Math.* 2:482 (1981).

Stapleton et al., *Biochemistry* 35:14352–14361 (1996).
Summar M L. *Journal of Inherited Metabolic Disease* 1998; 21 Suppl 1:30–9.
Summar, M., J. *Inherited Metabolic Disease* 21:30–39 (1998).
Summar M L, et al., *Cytogenetics & Cell Genetics* 1995; 71:266–7.
Takiguchi MaM, M., *Biochem J.* (1995) 312:649–659.
Toh, H. et al., *European Journal of Biochemistry* 215:687–696 (1993).
Tse et al., *American Journal of Hematology* 38:140–141 (1991).
U.S. Pat. No. 5,399,346
U.S. Pat. No. 5,162,215
U.S. Pat. No. 5,279,833
U.S. Pat. No. 5,643,567
U.S. Pat. No. 4,683,202
U.S. Pat. No. 4,683,195
U.S. Pat. No. 5,286,634
U.S. Pat. No. 5,646,008
U.S. Pat. No. 4,196,265
U.S. Pat. No. 5,489,742
U.S. Pat. No. 5,550,316
U.S. Pat. No. 5,573,933
U.S. Pat. No. 5,614,396
U.S. Pat. No. 5,625,125
U.S. Pat. No. 5,641,484
U.S. Pat. No. 5,648,061
U.S. Pat. No. 5,651,964
U.S. Pat. No. 4,965,188
U.S. Pat. No. 4,769,331
U.S. Pat. No. 5,741,957
U.S. Pat. No. 4,458,066
U.S. Pat. No. 4,554,101
U.S. Pat. No. 4,736,866
van den Hoff, M. J. et al, *Journal of Molecular Evolution* 41:813–832 (1995).
Vosatka R J, et al., *Biol Neonate* (1994) 66:65–70.
Warter et al., *Revue Neurologique* 139:753–757 (1983).
Wingard J R, et al. *Bone Marrow Transplantation* 1989; 4:685–9.
Zamora, S. A., et al., *Crit Care Med* (1998) 26: 1271–1276.

What is claimed is:

1. A method of treating or preventing sub-optimal urea cycle function in a subject, the method comprising administering to a subject in need thereof a therapeutically effective amount of a nitric oxide precursor, whereby treatment or prevention of sub-optimal urea cycle function is accomplished.

2. The method of claim 1, wherein the sub-optimal urea cycle function further comprises hyperammonemia or decreased arginine production.

3. The method of claim 1, wherein the subject is suffering from a disorder associated with impaired liver function or wherein the subject is exposed or about to be exposed to an environmental stimulus associated with impaired liver function.

4. The method of claim 3, wherein the disorder is selected from the group consisting of hepatitis, sclerosis, pulmonary hypertension, bone marrow transplant toxicity in a subject undergoing bone marrow transplant and combinations thereof.

5. The method of claim 3, wherein the environmental stimulus is selected from the group consisting of chemotherapy, cardiac surgery, increased oxidative stress, bone marrow transplant, and combinations thereof.

6. The method of claim 1, wherein the nitric oxide precursor is selected from the group consisting of citrulline, arginine and combinations thereof.

7. The method of claim 1, wherein the nitric oxide precursor is administered in a dose ranging from about 0.01 mg to about 1,000 mg.

8. The method of claim 7, wherein the nitric oxide precursor is administered in a dose ranging from about 0.5 mg to about 500 mg.

9. The method of claim 8, wherein the nitric oxide precursor is administered in a dose ranging from about 1.0 mg to about 250 mg.

10. A method of treating or preventing bone marrow transplant toxicity in a subject undergoing bone marrow transplant, the method comprising administering to the subject a therapeutically effective amount of a nitric oxide precursor, whereby bone marrow transplant toxicity is treated or prevented in the subject.

11. The method of claim 10, wherein the nitric oxide precursor is selected from the group consisting of citrulline, arginine and combinations thereof.

12. The method of claim 10, wherein the nitric oxide precursor is administered in a dose ranging from about 0.01 mg to about 1,000 mg.

13. The method of claim 12, wherein the nitric oxide precursor is administered in a dose ranging from about 0.5 mg to about 500 mg.

14. The method of claim 13, wherein the nitric oxide precursor is administered in a dose ranging from about 1.0 mg to about 250 mg.

15. The method of claim 10, wherein the bone marrow transplant toxicity comprises hepatic veno-occlusive disease.

* * * * *

UNITED STATES PATENT AND TRADEMARK OFFICE
CERTIFICATE OF CORRECTION

PATENT NO. : 6,743,823 B1
DATED : June 1, 2004
INVENTOR(S) : Marshall Summar et al.

It is certified that error appears in the above-identified patent and that said Letters Patent is hereby corrected as shown below:

Column 137,
Replace claims 1-15 with the following:

1. A method of treating or preventing sub-optimal urea cycle function in a human subject having a polymorphism that results in a N→T substitution at amino acid 1405 of a carbamyl phosphate synthetase I (CPSI) polypeptide, the method comprising determining whether a human subject has said polymorphism, and, if said human subject has said polymorphism, administering to the human subject a therapeutically effective amount of a nitric oxide precursor, whereby treatment or prevention of sub-optimal urea cycle function is accomplished.
2. The method of claim 1, wherein the sub-optimal urea cycle function further comprises hyperammonemia or decreased arginine production.
3. The method of claim 1, wherein the subject is suffering from a disorder associated with impaired liver function or wherein the subject is exposed or about to be exposed to an environmental stimulus associated with impaired liver function.
4. The method of claim 3, wherein the disorder is selected from the group consisting of hepatitis, sclerosis, pulmonary hypertension, bone marrow transplant toxicity in a subject undergoing bone marrow transplant and combinations thereof.
5. The method of claim 3, wherein the environmental stimulus is selected from the group consisting of chemotherapy, cardiac surgery, increased oxidative stress, bone marrow transplant, and combinations thereof.
6. The method of claim 1, wherein the nitric oxide precursor is selected from the group consisting of citrulline, arginine and combinations thereof.
7. The method of claim 1, wherein the nitric oxide precursor is administered in a dose ranging from about 0.01 mg to about 1,000 mg.
8. The method of claim 7, wherein the nitric oxide precursor is administered in a dose ranging from about 0.5 mg to about 500 mg.
9. The method of claim 8, wherein the nitric oxide precursor is administered in a dose ranging from about 1.0 mg to about 250 mg.
10. A method of treating or preventing bone marrow transplant toxicity in a human subject undergoing bone marrow transplant, the human subject having at least one copy of a carbamyl phosphate synthetase I (CPSI) gene that encodes a threonine residue at amino acid 1405 of a CPSI polypeptide, the method comprising determining whether a human subject has at least one copy of a CPSI gene encoding a threonine residue at amino acid 1405 of a CPSI polypeptide, and, if said human subject has at least one copy of a CPSI gene encoding a threonine residue at amino acid 1405 of a CPSI polypeptide, administering to the human subject a therapeutically effective amount of a nitric oxide precursor, whereby bone marrow transplant toxicity is treated or prevented in the human subject.
11. The method of claim 10, wherein the nitric oxide precursor is selected from the group consisting of citrulline, arginine and combinations thereof.
12. The method of claim 10, wherein the nitric oxide precursor is administered in a dose ranging from about 0.01 mg to about 1,000 mg.
13. The method of claim 12, wherein the nitric oxide precursor is administered in a dose ranging from about 0.5 mg to about 500 mg.
14. The method of claim 13, wherein the nitric oxide precursor is administered in a dose ranging from about 1.0 mg to about 250 mg.
15. The method of claim 10, wherein the bone marrow transplant toxicity comprises hepatic veno-occlusive disease.

Signed and Sealed this

Thirtieth Day of November, 2004

JON W. DUDAS
*Director of the United States Patent and Trademark Office*

SEQUENCE LISTING

<160> NUMBER OF SEQ ID NOS: 23

<210> SEQ ID NO 1
<211> LENGTH: 5761
<212> TYPE: DNA
<213> ORGANISM: Homo sapiens
<220> FEATURE:
<221> NAME/KEY: CDS
<222> LOCATION: (124)..(4626)

<400> SEQUENCE: 1

```
gtcagcctta aacactgact gcacccctcc cagatttctt ttacattaac taaaaagtct      60
tatcacacaa tctcataaaa tttatgtaat ttcatttaat tttagccaca aatcatcttc     120 aaa atg acg agg att ttg aca gct ttc aaa gtg gtg agg aca ctg aag       168
    Met Thr Arg Ile Leu Thr Ala Phe Lys Val Val Arg Thr Leu Lys
    1               5                   10                  15 act ggt ttt ggc ttt acc aat gtg act gca cac caa aaa tgg aaa ttt       216
Thr Gly Phe Gly Phe Thr Asn Val Thr Ala His Gln Lys Trp Lys Phe
                20                  25                  30 tca aga cct ggc atc agg ctc ctt tct gtc aag gca cag aca gca cac       264
Ser Arg Pro Gly Ile Arg Leu Leu Ser Val Lys Ala Gln Thr Ala His
            35                  40                  45 att gtc ctg gaa gat gga act aag atg aaa ggt tac tcc ttt ggc cat       312
Ile Val Leu Glu Asp Gly Thr Lys Met Lys Gly Tyr Ser Phe Gly His
        50                  55                  60 cca tcc tct gtt gct ggt gaa gtg gtt ttt aat act ggc ctg gga ggg       360
Pro Ser Ser Val Ala Gly Glu Val Val Phe Asn Thr Gly Leu Gly Gly
65                  70                  75 tac cca gaa gct att act gac cct gcc tac aaa gga cag att ctc aca       408
Tyr Pro Glu Ala Ile Thr Asp Pro Ala Tyr Lys Gly Gln Ile Leu Thr
80                  85                  90                  95 atg gcc aac cct att att ggg aat ggt gga gct cct gat act act gct       456
Met Ala Asn Pro Ile Ile Gly Asn Gly Gly Ala Pro Asp Thr Thr Ala
                100                 105                 110 ctg gat gaa ctg gga ctt agc aaa tat ttg gag tct aat gga atc aag       504
Leu Asp Glu Leu Gly Leu Ser Lys Tyr Leu Glu Ser Asn Gly Ile Lys
            115                 120                 125 gtt tca ggt ttg ctg gtg ctg gat tat agt aaa gac tac aac cac tgg       552
```

```
                                                                          -continued Val Ser Gly Leu Leu Val Leu Asp Tyr Ser Lys Asp Tyr Asn His Trp
                130                 135                 140 ctg gct acc aag agt tta ggg caa tgg cta cag gaa gaa aag gtt cct       600
Leu Ala Thr Lys Ser Leu Gly Gln Trp Leu Gln Glu Glu Lys Val Pro
145                 150                 155 gca att tat gga gtg gac aca aga atg ctg act aaa ata att cgg gat       648
Ala Ile Tyr Gly Val Asp Thr Arg Met Leu Thr Lys Ile Ile Arg Asp
160                 165                 170                 175 aag ggt acc atg ctt ggg aag att gaa ttt gaa ggt cag cct gtg gat       696
Lys Gly Thr Met Leu Gly Lys Ile Glu Phe Glu Gly Gln Pro Val Asp
                180                 185                 190 ttt gtg gat cca aat aaa cag aat ttg att gct gag gtt tca acc aag       744
Phe Val Asp Pro Asn Lys Gln Asn Leu Ile Ala Glu Val Ser Thr Lys
                195                 200                 205 gat gtc aaa gtg tac ggc aaa gga aac ccc aca aaa gtg gta gct gta       792
Asp Val Lys Val Tyr Gly Lys Gly Asn Pro Thr Lys Val Val Ala Val
                210                 215                 220 gac tgt ggg att aaa aac aat gta atc cgc ctg cta gta aag cga gga       840
Asp Cys Gly Ile Lys Asn Asn Val Ile Arg Leu Leu Val Lys Arg Gly
225                 230                 235 gct gaa gtg cac tta gtt ccc tgg aac cat gat ttc acc aag atg gag       888
Ala Glu Val His Leu Val Pro Trp Asn His Asp Phe Thr Lys Met Glu
240                 245                 250                 255 tat gat ggg att ttg atc gcg gga gga ccg ggg aac cca gct ctt gca       936
Tyr Asp Gly Ile Leu Ile Ala Gly Gly Pro Gly Asn Pro Ala Leu Ala
                260                 265                 270 gaa cca cta att cag aat gtc aga aag att ttg gag agt gat cgc aag       984
Glu Pro Leu Ile Gln Asn Val Arg Lys Ile Leu Glu Ser Asp Arg Lys
                275                 280                 285 gag cca ttg ttt gga atc agt aca gga aac tta ata aca gga ttg gct      1032
Glu Pro Leu Phe Gly Ile Ser Thr Gly Asn Leu Ile Thr Gly Leu Ala
                290                 295                 300 gct ggt gcc aaa acc tac aag atg tcc atg gcc aac aga ggg cag aat      1080
Ala Gly Ala Lys Thr Tyr Lys Met Ser Met Ala Asn Arg Gly Gln Asn
305                 310                 315 cag cct gtt ttg aat atc aca aac aaa cag gct ttc att act gct cag      1128
Gln Pro Val Leu Asn Ile Thr Asn Lys Gln Ala Phe Ile Thr Ala Gln
320                 325                 330                 335 aat cat ggc tat gcc ttg gac aac acc ctc cct gct ggc tgg aaa cca      1176
Asn His Gly Tyr Ala Leu Asp Asn Thr Leu Pro Ala Gly Trp Lys Pro
                340                 345                 350 ctt ttt gtg aat gtc aac gat caa aca aat gag ggg att atg cat gag      1224
Leu Phe Val Asn Val Asn Asp Gln Thr Asn Glu Gly Ile Met His Glu
                355                 360                 365 agc aaa ccc ttc ttc gct gtg cag ttc cac cca gag gtc acc ccg ggg      1272
Ser Lys Pro Phe Phe Ala Val Gln Phe His Pro Glu Val Thr Pro Gly
                370                 375                 380 cca ata gac act gag tac ctg ttt gat tcc ttt tca ctg ata aag           1320
Pro Ile Asp Thr Glu Tyr Leu Phe Asp Ser Phe Ser Leu Ile Lys
385                 390                 395 aaa gga aaa gct acc acc att aca tca gtc tta ccg aag cca gca cta      1368
Lys Gly Lys Ala Thr Thr Ile Thr Ser Val Leu Pro Lys Pro Ala Leu
400                 405                 410                 415 gtt gca tct cgg gtt gag gtt tcc aaa gtc ctt att cta gga tca gga      1416
Val Ala Ser Arg Val Glu Val Ser Lys Val Leu Ile Leu Gly Ser Gly
                420                 425                 430 ggt ctg tcc att ggt cag gct gga gaa ttt gat tac tca gga tct caa      1464
Gly Leu Ser Ile Gly Gln Ala Gly Glu Phe Asp Tyr Ser Gly Ser Gln
                435                 440                 445
```

```
gct gta aaa gcc atg aag gaa gaa aat gtc aaa act gtt ctg atg aac    1512
Ala Val Lys Ala Met Lys Glu Glu Asn Val Lys Thr Val Leu Met Asn
        450                 455                 460 cca aac att gca tca gtc cag acc aat gag gtg ggc tta aag caa gcg    1560
Pro Asn Ile Ala Ser Val Gln Thr Asn Glu Val Gly Leu Lys Gln Ala
465                 470                 475 gat act gtc tac ttt ctt ccc atc acc cct cag ttt gtc aca gag gtc    1608
Asp Thr Val Tyr Phe Leu Pro Ile Thr Pro Gln Phe Val Thr Glu Val
480                 485                 490                 495 atc aag gca gaa cag cca gat ggg tta att ctg ggc atg ggt ggc cag    1656
Ile Lys Ala Glu Gln Pro Asp Gly Leu Ile Leu Gly Met Gly Gly Gln
                500                 505                 510 aca gct ctg aac tgt gga gtg gaa cta ttc aag aga ggt gtg ctc aag    1704
Thr Ala Leu Asn Cys Gly Val Glu Leu Phe Lys Arg Gly Val Leu Lys
        515                 520                 525 gaa tat ggt gtg aaa gtc ctg gga act tca gtt gag tcc att atg gct    1752
Glu Tyr Gly Val Lys Val Leu Gly Thr Ser Val Glu Ser Ile Met Ala
        530                 535                 540 acg gaa gac agg cag ctg ttt tca gat aaa cta aat gag atc aat gaa    1800
Thr Glu Asp Arg Gln Leu Phe Ser Asp Lys Leu Asn Glu Ile Asn Glu
545                 550                 555 aag att gct cca agt ttt gca gtg gaa tcg att gag gat gca ctg aag    1848
Lys Ile Ala Pro Ser Phe Ala Val Glu Ser Ile Glu Asp Ala Leu Lys
560                 565                 570                 575 gca gca gac acc att ggc tac cca gtg atg atc cgt tcc gcc tat gca    1896
Ala Ala Asp Thr Ile Gly Tyr Pro Val Met Ile Arg Ser Ala Tyr Ala
                580                 585                 590 ctg ggt ggg tta ggc tca ggc atc tgt ccc aac aga gag act ttg atg    1944
Leu Gly Gly Leu Gly Ser Gly Ile Cys Pro Asn Arg Glu Thr Leu Met
        595                 600                 605 gac ctc agc aca aag gcc ttt gct atg acc aac caa att ctg gtg gag    1992
Asp Leu Ser Thr Lys Ala Phe Ala Met Thr Asn Gln Ile Leu Val Glu
        610                 615                 620 aag tca gtg aca ggt tgg aaa gaa ata gaa tat gaa gtg gtt cga gat    2040
Lys Ser Val Thr Gly Trp Lys Glu Ile Glu Tyr Glu Val Val Arg Asp
625                 630                 635 gct gat gac aat tgt gtc act gtc tgt aac atg gaa aat gtt gat gcc    2088
Ala Asp Asp Asn Cys Val Thr Val Cys Asn Met Glu Asn Val Asp Ala
640                 645                 650                 655 atg ggt gtt cac aca ggt gac tca gtt gtt gtg gct cct gcc cag aca    2136
Met Gly Val His Thr Gly Asp Ser Val Val Val Ala Pro Ala Gln Thr
                660                 665                 670 ctc tcc aat gcc gag ttt cag atg ttg aga cgt act tca atc aat gtt    2184
Leu Ser Asn Ala Glu Phe Gln Met Leu Arg Arg Thr Ser Ile Asn Val
        675                 680                 685 gtt cgc cac ttg ggc att gtg ggt gaa tgc aac att cag ttt gcc ctt    2232
Val Arg His Leu Gly Ile Val Gly Glu Cys Asn Ile Gln Phe Ala Leu
        690                 695                 700 cat cct acc tca atg gaa tac tgc atc att gaa gtg aat gcc aga ctg    2280
His Pro Thr Ser Met Glu Tyr Cys Ile Ile Glu Val Asn Ala Arg Leu
705                 710                 715 tcc cga agc tct gct ctg gcc tca aaa gcc act ggc tac cca ttg gca    2328
Ser Arg Ser Ser Ala Leu Ala Ser Lys Ala Thr Gly Tyr Pro Leu Ala
720                 725                 730                 735 ttc att gct gca aag att gcc cta gga atc cca ctt cca gaa att aag    2376
Phe Ile Ala Ala Lys Ile Ala Leu Gly Ile Pro Leu Pro Glu Ile Lys
                740                 745                 750 aac gtc gta tcc ggg aag aca tca gcc tgt ttt gaa cct agc ctg gat    2424
Asn Val Val Ser Gly Lys Thr Ser Ala Cys Phe Glu Pro Ser Leu Asp
        755                 760                 765
```

```
tac atg gtc acc aag att ccc cgc tgg gat ctt gac cgt ttt cat gga    2472
Tyr Met Val Thr Lys Ile Pro Arg Trp Asp Leu Asp Arg Phe His Gly
            770                 775                 780 aca tct agc cga att ggt agc tct atg aaa agt gta gga gag gtc atg    2520
Thr Ser Ser Arg Ile Gly Ser Ser Met Lys Ser Val Gly Glu Val Met
785                 790                 795 gct att ggt cgt acc ttt gag gag agt ttc cag aaa gct tta cgg atg    2568
Ala Ile Gly Arg Thr Phe Glu Glu Ser Phe Gln Lys Ala Leu Arg Met
800                 805                 810                 815 tgc cac cca tct ata gaa ggt ttc act ccc cgt ctc cca atg aac aaa    2616
Cys His Pro Ser Ile Glu Gly Phe Thr Pro Arg Leu Pro Met Asn Lys
                820                 825                 830 gaa tgg cca tct aat tta gat ctt aga aaa gag ttg tct gaa cca agc    2664
Glu Trp Pro Ser Asn Leu Asp Leu Arg Lys Glu Leu Ser Glu Pro Ser
            835                 840                 845 agc acg cgt atc tat gcc att gcc aag gcc att gat gac aac atg tcc    2712
Ser Thr Arg Ile Tyr Ala Ile Ala Lys Ala Ile Asp Asp Asn Met Ser
        850                 855                 860 ctt gat gag att gag aag ctc aca tac att gac aag tgg ttt ttg tat    2760
Leu Asp Glu Ile Glu Lys Leu Thr Tyr Ile Asp Lys Trp Phe Leu Tyr
    865                 870                 875 aag atg cgt gat att tta aac atg gaa aag aca ctg aaa ggg ctc aac    2808
Lys Met Arg Asp Ile Leu Asn Met Glu Lys Thr Leu Lys Gly Leu Asn
880                 885                 890                 895 agt gag tcc atg aca gaa gaa acc ctg aaa agg gca aag gag att ggg    2856
Ser Glu Ser Met Thr Glu Glu Thr Leu Lys Arg Ala Lys Glu Ile Gly
                900                 905                 910 ttc tca gat aag cag att tca aaa tgc ctt ggg ctc act gag gcc cag    2904
Phe Ser Asp Lys Gln Ile Ser Lys Cys Leu Gly Leu Thr Glu Ala Gln
            915                 920                 925 aca agg gag ctg agg tta aag aaa aac atc cac cct tgg gtt aaa cag    2952
Thr Arg Glu Leu Arg Leu Lys Lys Asn Ile His Pro Trp Val Lys Gln
        930                 935                 940 att gat aca ctg gct gca gaa tac cca tca gta aca aac tat ctc tat    3000
Ile Asp Thr Leu Ala Ala Glu Tyr Pro Ser Val Thr Asn Tyr Leu Tyr
    945                 950                 955 gtt acc tac aat ggt cag gag cat gat gtc aat ttt gat gac cat gga    3048
Val Thr Tyr Asn Gly Gln Glu His Asp Val Asn Phe Asp Asp His Gly
960                 965                 970                 975 atg atg gtg cta ggc tgt ggt cca tat cac att ggc agc agt gtg gaa    3096
Met Met Val Leu Gly Cys Gly Pro Tyr His Ile Gly Ser Ser Val Glu
                980                 985                 990 ttt gat tgg tgt gct gtc tct agt atc cgc aca ctg cgt caa ctt ggc    3144
Phe Asp Trp Cys Ala Val Ser Ser Ile Arg Thr Leu Arg Gln Leu Gly
            995                 1000                1005 aag aag acg gtg gtg gtg aat tgc aat cct gag act gtg agc aca       3189
Lys Lys Thr Val Val Val Asn Cys Asn Pro Glu Thr Val Ser Thr
        1010                1015                1020 gac ttt gat gag tgt gac aaa ctg tac ttt gaa gag ttg tcc ttg       3234
Asp Phe Asp Glu Cys Asp Lys Leu Tyr Phe Glu Glu Leu Ser Leu
    1025                1030                1035 gag aga atc cta gac atc tac cat cag gag gca tgt ggt ggc tgc       3279
Glu Arg Ile Leu Asp Ile Tyr His Gln Glu Ala Cys Gly Gly Cys
    1040                1045                1050 atc ata tca gtt gga ggc cag att cca aac aac ctg gca gtt cct       3324
Ile Ile Ser Val Gly Gly Gln Ile Pro Asn Asn Leu Ala Val Pro
    1055                1060                1065 cta tac aag aat ggt gtc aag atc atg ggc aca agc ccc ctg cag       3369
Leu Tyr Lys Asn Gly Val Lys Ile Met Gly Thr Ser Pro Leu Gln
```

|  |  |  |  |  |  |  |  |  |  |  |  |  |
|---|---|---|---|---|---|---|---|---|---|---|---|---|
| | 1070 | | | | 1075 | | | | 1080 | | | |
| atc | gac | agg | gct | gag | gat | cgc | tcc | atc | ttc | tca | gct | gtc | ttg | gat | 3414 |
| Ile | Asp | Arg | Ala | Glu | Asp | Arg | Ser | Ile | Phe | Ser | Ala | Val | Leu | Asp |  |
| | | 1085 | | | | 1090 | | | | 1095 | | | |
| gag | ctg | aag | gtg | gct | cag | gca | cct | tgg | aaa | gct | gtt | aat | act | ttg | 3459 |
| Glu | Leu | Lys | Val | Ala | Gln | Ala | Pro | Trp | Lys | Ala | Val | Asn | Thr | Leu |  |
| | | 1100 | | | | 1105 | | | | 1110 | | | |
| aat | gaa | gca | ctg | gaa | ttt | gca | aag | tct | gtg | gac | tac | ccc | tgc | ttg | 3504 |
| Asn | Glu | Ala | Leu | Glu | Phe | Ala | Lys | Ser | Val | Asp | Tyr | Pro | Cys | Leu |  |
| | | 1115 | | | | 1120 | | | | 1125 | | | |
| ttg | agg | cct | tcc | tat | gtt | ttg | agt | ggg | tct | gct | atg | aat | gtg | gta | 3549 |
| Leu | Arg | Pro | Ser | Tyr | Val | Leu | Ser | Gly | Ser | Ala | Met | Asn | Val | Val |  |
| | | 1130 | | | | 1135 | | | | 1140 | | | |
| ttc | tct | gag | gat | gag | atg | aaa | aaa | ttc | cta | gaa | gag | gcg | act | aga | 3594 |
| Phe | Ser | Glu | Asp | Glu | Met | Lys | Lys | Phe | Leu | Glu | Glu | Ala | Thr | Arg |  |
| | | 1145 | | | | 1150 | | | | 1155 | | | |
| gtt | tct | cag | gag | cac | cca | gtg | gtc | ctg | aca | aaa | ttt | gtt | gaa | ggg | 3639 |
| Val | Ser | Gln | Glu | His | Pro | Val | Val | Leu | Thr | Lys | Phe | Val | Glu | Gly |  |
| | | 1160 | | | | 1165 | | | | 1170 | | | |
| gcc | cga | gaa | gta | gaa | atg | gac | gct | gtt | ggc | aaa | gat | gga | agg | gtt | 3684 |
| Ala | Arg | Glu | Val | Glu | Met | Asp | Ala | Val | Gly | Lys | Asp | Gly | Arg | Val |  |
| | | 1175 | | | | 1180 | | | | 1185 | | | |
| atc | tct | cat | gcc | atc | tct | gaa | cat | gtt | gaa | gat | gca | ggt | gtc | cac | 3729 |
| Ile | Ser | His | Ala | Ile | Ser | Glu | His | Val | Glu | Asp | Ala | Gly | Val | His |  |
| | | 1190 | | | | 1195 | | | | 1200 | | | |
| tcg | gga | gat | gcc | act | ctg | atg | ctg | ccc | aca | caa | acc | atc | agc | caa | 3774 |
| Ser | Gly | Asp | Ala | Thr | Leu | Met | Leu | Pro | Thr | Gln | Thr | Ile | Ser | Gln |  |
| | | 1205 | | | | 1210 | | | | 1215 | | | |
| ggg | gcc | att | gaa | aag | gtg | aag | gat | gct | acc | cgg | aag | att | gca | aag | 3819 |
| Gly | Ala | Ile | Glu | Lys | Val | Lys | Asp | Ala | Thr | Arg | Lys | Ile | Ala | Lys |  |
| | | 1220 | | | | 1225 | | | | 1230 | | | |
| gct | ttt | gcc | atc | tct | ggt | cca | ttc | aac | gtc | caa | ttt | ctt | gtc | aaa | 3864 |
| Ala | Phe | Ala | Ile | Ser | Gly | Pro | Phe | Asn | Val | Gln | Phe | Leu | Val | Lys |  |
| | | 1235 | | | | 1240 | | | | 1245 | | | |
| gga | aat | gat | gtc | ttg | gtg | att | gag | tgt | aac | ttg | aga | gct | tct | cga | 3909 |
| Gly | Asn | Asp | Val | Leu | Val | Ile | Glu | Cys | Asn | Leu | Arg | Ala | Ser | Arg |  |
| | | 1250 | | | | 1255 | | | | 1260 | | | |
| tcc | ttc | ccc | ttt | gtt | tcc | aag | act | ctt | ggg | gtt | gac | ttc | att | gat | 3954 |
| Ser | Phe | Pro | Phe | Val | Ser | Lys | Thr | Leu | Gly | Val | Asp | Phe | Ile | Asp |  |
| | | 1265 | | | | 1270 | | | | 1275 | | | |
| gtg | gcc | acc | aag | gtg | atg | att | gga | gag | aat | gtt | gat | gag | aaa | cat | 3999 |
| Val | Ala | Thr | Lys | Val | Met | Ile | Gly | Glu | Asn | Val | Asp | Glu | Lys | His |  |
| | | 1280 | | | | 1285 | | | | 1290 | | | |
| ctt | cca | aca | ttg | gac | cat | ccc | ata | att | cct | gct | gac | tat | gtt | gca | 4044 |
| Leu | Pro | Thr | Leu | Asp | His | Pro | Ile | Ile | Pro | Ala | Asp | Tyr | Val | Ala |  |
| | | 1295 | | | | 1300 | | | | 1305 | | | |
| att | aag | gct | ccc | atg | ttt | tcc | tgg | ccc | cgg | ttg | agg | gat | gct | gac | 4089 |
| Ile | Lys | Ala | Pro | Met | Phe | Ser | Trp | Pro | Arg | Leu | Arg | Asp | Ala | Asp |  |
| | | 1310 | | | | 1315 | | | | 1320 | | | |
| ccc | att | ctg | aga | tgt | gag | atg | gct | tcc | act | gga | gag | gtg | gct | tgc | 4134 |
| Pro | Ile | Leu | Arg | Cys | Glu | Met | Ala | Ser | Thr | Gly | Glu | Val | Ala | Cys |  |
| | | 1325 | | | | 1330 | | | | 1335 | | | |
| ttt | ggt | gaa | ggt | att | cat | aca | gcc | ttc | cta | aag | gca | atg | ctt | tcc | 4179 |
| Phe | Gly | Glu | Gly | Ile | His | Thr | Ala | Phe | Leu | Lys | Ala | Met | Leu | Ser |  |
| | | 1340 | | | | 1345 | | | | 1350 | | | |
| aca | gga | ttt | aag | ata | ccc | cag | aaa | ggc | atc | ctg | ata | ggc | atc | cag | 4224 |
| Thr | Gly | Phe | Lys | Ile | Pro | Gln | Lys | Gly | Ile | Leu | Ile | Gly | Ile | Gln |  |
| | | 1355 | | | | 1360 | | | | 1365 | | | |
| caa | tca | ttc | cgg | cca | aga | ttc | ctt | ggt | gtg | gct | gaa | caa | tta | cac | 4269 |

```
                                                     -continued

Gln Ser Phe Arg Pro Arg Phe Leu Gly Val Ala Glu Gln Leu His
        1370                1375                1380 aat gaa ggt ttc aag ctg ttt gcc acg gaa gcc aca tca gac tgg        4314
Asn Glu Gly Phe Lys Leu Phe Ala Thr Glu Ala Thr Ser Asp Trp
    1385                1390                1395 ctc aac gcc aac aat gtc cct gcc aac cca gtg gca tgg ccg tct        4359
Leu Asn Ala Asn Asn Val Pro Ala Asn Pro Val Ala Trp Pro Ser
1400                1405                1410 caa gaa gga cag aat ccc agc ctc tct tcc atc aga aaa ttg att        4404
Gln Glu Gly Gln Asn Pro Ser Leu Ser Ser Ile Arg Lys Leu Ile
    1415                1420                1425 aga gat ggc agc att gac cta gtg att aac ctt ccc aac aac aac        4449
Arg Asp Gly Ser Ile Asp Leu Val Ile Asn Leu Pro Asn Asn Asn
1430                1435                1440 act aaa ttt gtc cat gat aat tat gtg att cgg agg aca gct gtt        4494
Thr Lys Phe Val His Asp Asn Tyr Val Ile Arg Arg Thr Ala Val
    1445                1450                1455 gat agt gga atc cct ctc ctc act aat ttt cag gtg acc aaa ctt        4539
Asp Ser Gly Ile Pro Leu Leu Thr Asn Phe Gln Val Thr Lys Leu
1460                1465                1470 ttt gct gaa gct gtg cag aaa tct cgc aag gtg gac tcc aag agt        4584
Phe Ala Glu Ala Val Gln Lys Ser Arg Lys Val Asp Ser Lys Ser
    1475                1480                1485 ctt ttc cac tac agg cag tac agt gct gga aaa gca gca tag            4626
Leu Phe His Tyr Arg Gln Tyr Ser Ala Gly Lys Ala Ala
1490                1495                1500 agatgcagac accccagccc cattattaaa tcaacctgag ccacatgtta tctaaaggaa  4686
ctgattcaca actttctcag agatgaatat tgataactaa acttcatttc agtttacttt  4746
gttatgcctt aatattctgt gtcttttgca attaaattgt cagtcacttc ttcaaaacct  4806
tacagtcctt cctaagttac tcttcatgag atttcatcca tttactaata ctgtattttt  4866
ggtggactag gcttgcctat gtgcttatgt gtagcttttt acttttatg gtgctgatta   4926 atggtgatca aggtaggaaa agttgctgtt ctattttctg aactctttct atactttaag  4986
atactctatt tttaaaacac tatctgcaaa ctcaggacac tttaacaggg cagaatactc  5046
taaaaacttg ataaaatgaa atatagattt aatttatgaa ccttccatca tgatgtttgt  5106
gtattgcttc ttttttggatc ctcattctca cccatttggc taatccagga atattgttat 5166 cccttcccat tatattgaag ttgagaaatg tgacagaggc atttagagta tggacttttc  5226
ttttcttttt ctttttcttt ttttcttttt gagatggagt cacactctcc aggctggagt  5286
gcagtggcac aatctcggct cactgcaatt tgcgtctccc aagttcaagc gattctcctg  5346
ctttagacta tggatttctt taaggaatac tggtttgcag ttttgttttc tggactatat  5406
cagcagatgg tagacagtgt ttatgtagat gtgttgttgt ttttatcatt ggattttaac  5466
ttggcccgag tgaaataatc agattttttgt cattcacact ctcccccagt tttgaataa   5526 cttggaagta aggttcattc ccttaagacg atggattctg ttgaactatg ggtcccaca   5586 ctgcactatt aattccaccc actgtaaggg caaggacacc attccttcta catataagaa  5646
aaaagtctct ccccaagggc agcctttgtt acttttaaat attttctgtt attacaagtg  5706
ctctaattgt gaacttttaa ataaaatact attaagaggt aaaaaaaaaa aaaaa        5761

<210> SEQ ID NO 2
<211> LENGTH: 1500
<212> TYPE: PRT
<213> ORGANISM: Homo sapiens
```

-continued

```
<400> SEQUENCE: 2

Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
130                 135                 140

Ala Thr Lys Ser Leu Gly Gln Trp Leu Gln Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
        275                 280                 285

Pro Leu Phe Gly Ile Ser Thr Gly Asn Leu Ile Thr Gly Leu Ala Ala
290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
            340                 345                 350

Phe Val Asn Val Asn Asp Gln Thr Asn Glu Gly Ile Met His Glu Ser
        355                 360                 365

Lys Pro Phe Phe Ala Val Gln Phe His Pro Glu Val Thr Pro Gly Pro
370                 375                 380

Ile Asp Thr Glu Tyr Leu Phe Asp Ser Phe Phe Ser Leu Ile Lys Lys
385                 390                 395                 400

Gly Lys Ala Thr Thr Ile Thr Ser Val Leu Pro Lys Pro Ala Leu Val
                405                 410                 415
```

-continued

```
Ala Ser Arg Val Glu Val Ser Lys Val Leu Ile Leu Gly Ser Gly Gly
                420                 425                 430
Leu Ser Ile Gly Gln Ala Gly Glu Phe Asp Tyr Ser Gly Ser Gln Ala
            435                 440                 445
Val Lys Ala Met Lys Glu Glu Asn Val Lys Thr Val Leu Met Asn Pro
    450                 455                 460
Asn Ile Ala Ser Val Gln Thr Asn Glu Val Gly Leu Lys Gln Ala Asp
465                 470                 475                 480
Thr Val Tyr Phe Leu Pro Ile Thr Pro Gln Phe Val Thr Glu Val Ile
                485                 490                 495
Lys Ala Glu Gln Pro Asp Gly Leu Ile Leu Gly Met Gly Gly Gln Thr
            500                 505                 510
Ala Leu Asn Cys Gly Val Glu Leu Phe Lys Arg Gly Val Leu Lys Glu
    515                 520                 525
Tyr Gly Val Lys Val Leu Gly Thr Ser Val Glu Ser Ile Met Ala Thr
    530                 535                 540
Glu Asp Arg Gln Leu Phe Ser Asp Lys Leu Asn Glu Ile Asn Glu Lys
545                 550                 555                 560
Ile Ala Pro Ser Phe Ala Val Glu Ser Ile Glu Asp Ala Leu Lys Ala
                565                 570                 575
Ala Asp Thr Ile Gly Tyr Pro Val Met Ile Arg Ser Ala Tyr Ala Leu
            580                 585                 590
Gly Gly Leu Gly Ser Gly Ile Cys Pro Asn Arg Glu Thr Leu Met Asp
    595                 600                 605
Leu Ser Thr Lys Ala Phe Ala Met Thr Asn Gln Ile Leu Val Glu Lys
    610                 615                 620
Ser Val Thr Gly Trp Lys Glu Ile Glu Tyr Glu Val Val Arg Asp Ala
625                 630                 635                 640
Asp Asp Asn Cys Val Thr Val Cys Asn Met Glu Asn Val Asp Ala Met
                645                 650                 655
Gly Val His Thr Gly Asp Ser Val Val Val Ala Pro Ala Gln Thr Leu
            660                 665                 670
Ser Asn Ala Glu Phe Gln Met Leu Arg Arg Thr Ser Ile Asn Val Val
    675                 680                 685
Arg His Leu Gly Ile Val Gly Glu Cys Asn Ile Gln Phe Ala Leu His
    690                 695                 700
Pro Thr Ser Met Glu Tyr Cys Ile Ile Glu Val Asn Ala Arg Leu Ser
705                 710                 715                 720
Arg Ser Ser Ala Leu Ala Ser Lys Ala Thr Gly Tyr Pro Leu Ala Phe
                725                 730                 735
Ile Ala Ala Lys Ile Ala Leu Gly Ile Pro Leu Pro Glu Ile Lys Asn
            740                 745                 750
Val Val Ser Gly Lys Thr Ser Ala Cys Phe Glu Pro Ser Leu Asp Tyr
    755                 760                 765
Met Val Thr Lys Ile Pro Arg Trp Asp Leu Asp Arg Phe His Gly Thr
    770                 775                 780
Ser Ser Arg Ile Gly Ser Ser Met Lys Ser Val Gly Glu Val Met Ala
785                 790                 795                 800
Ile Gly Arg Thr Phe Glu Glu Ser Phe Gln Lys Ala Leu Arg Met Cys
                805                 810                 815
His Pro Ser Ile Glu Gly Phe Thr Pro Arg Leu Pro Met Asn Lys Glu
            820                 825                 830
```

-continued

```
Trp Pro Ser Asn Leu Asp Leu Arg Lys Glu Leu Ser Glu Pro Ser Ser
        835                 840                 845

Thr Arg Ile Tyr Ala Ile Ala Lys Ala Ile Asp Asp Asn Met Ser Leu
    850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
                885                 890                 895

Glu Ser Met Thr Glu Glu Thr Leu Lys Arg Ala Lys Glu Ile Gly Phe
            900                 905                 910

Ser Asp Lys Gln Ile Ser Lys Cys Leu Gly Leu Thr Glu Ala Gln Thr
        915                 920                 925

Arg Glu Leu Arg Leu Lys Lys Asn Ile His Pro Trp Val Lys Gln Ile
    930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
        995                 1000                1005

Lys Thr Val Val Val Asn Cys Asn Pro Glu Thr Val Ser Thr Asp
    1010                1015                1020

Phe Asp Glu Cys Asp Lys Leu Tyr Phe Glu Glu Leu Ser Leu Glu
    1025                1030                1035

Arg Ile Leu Asp Ile Tyr His Gln Glu Ala Cys Gly Gly Cys Ile
    1040                1045                1050

Ile Ser Val Gly Gly Gln Ile Pro Asn Asn Leu Ala Val Pro Leu
    1055                1060                1065

Tyr Lys Asn Gly Val Lys Ile Met Gly Thr Ser Pro Leu Gln Ile
    1070                1075                1080

Asp Arg Ala Glu Asp Arg Ser Ile Phe Ser Ala Val Leu Asp Glu
    1085                1090                1095

Leu Lys Val Ala Gln Ala Pro Trp Lys Ala Val Asn Thr Leu Asn
    1100                1105                1110

Glu Ala Leu Glu Phe Ala Lys Ser Val Asp Tyr Pro Cys Leu Leu
    1115                1120                1125

Arg Pro Ser Tyr Val Leu Ser Gly Ser Ala Met Asn Val Val Phe
    1130                1135                1140

Ser Glu Asp Glu Met Lys Lys Phe Leu Glu Glu Ala Thr Arg Val
    1145                1150                1155

Ser Gln Glu His Pro Val Val Leu Thr Lys Phe Val Glu Gly Ala
    1160                1165                1170

Arg Glu Val Glu Met Asp Ala Val Gly Lys Asp Gly Arg Val Ile
    1175                1180                1185

Ser His Ala Ile Ser Glu His Val Glu Asp Ala Gly Val His Ser
    1190                1195                1200

Gly Asp Ala Thr Leu Met Leu Pro Thr Gln Thr Ile Ser Gln Gly
    1205                1210                1215

Ala Ile Glu Lys Val Lys Asp Ala Thr Arg Lys Ile Ala Lys Ala
    1220                1225                1230

Phe Ala Ile Ser Gly Pro Phe Asn Val Gln Phe Leu Val Lys Gly
```

-continued

```
                1235                1240                1245

Asn Asp Val Leu Val Ile Glu Cys Asn Leu Arg Ala Ser Arg Ser
    1250                1255                1260

Phe Pro Phe Val Ser Lys Thr Leu Gly Val Asp Phe Ile Asp Val
    1265                1270                1275

Ala Thr Lys Val Met Ile Gly Glu Asn Val Asp Glu Lys His Leu
    1280                1285                1290

Pro Thr Leu Asp His Pro Ile Ile Pro Ala Asp Tyr Val Ala Ile
    1295                1300                1305

Lys Ala Pro Met Phe Ser Trp Pro Arg Leu Arg Asp Ala Asp Pro
    1310                1315                1320

Ile Leu Arg Cys Glu Met Ala Ser Thr Gly Glu Val Ala Cys Phe
    1325                1330                1335

Gly Glu Gly Ile His Thr Ala Phe Leu Lys Ala Met Leu Ser Thr
    1340                1345                1350

Gly Phe Lys Ile Pro Gln Lys Gly Ile Leu Ile Gly Ile Gln Gln
    1355                1360                1365

Ser Phe Arg Pro Arg Phe Leu Gly Val Ala Glu Gln Leu His Asn
    1370                1375                1380

Glu Gly Phe Lys Leu Phe Ala Thr Glu Ala Thr Ser Asp Trp Leu
    1385                1390                1395

Asn Ala Asn Asn Val Pro Ala Asn Pro Val Ala Trp Pro Ser Gln
    1400                1405                1410

Glu Gly Gln Asn Pro Ser Leu Ser Ser Ile Arg Lys Leu Ile Arg
    1415                1420                1425

Asp Gly Ser Ile Asp Leu Val Ile Asn Leu Pro Asn Asn Asn Thr
    1430                1435                1440

Lys Phe Val His Asp Asn Tyr Val Ile Arg Arg Thr Ala Val Asp
    1445                1450                1455

Ser Gly Ile Pro Leu Leu Thr Asn Phe Gln Val Thr Lys Leu Phe
    1460                1465                1470

Ala Glu Ala Val Gln Lys Ser Arg Lys Val Asp Ser Lys Ser Leu
    1475                1480                1485

Phe His Tyr Arg Gln Tyr Ser Ala Gly Lys Ala Ala
    1490                1495                1500

<210> SEQ ID NO 3
<211> LENGTH: 5761
<212> TYPE: DNA
<213> ORGANISM: Homo sapiens
<220> FEATURE:
<221> NAME/KEY: CDS
<222> LOCATION: (124)..(4626)

<400> SEQUENCE: 3
gtcagcctta aaacactgact gcacccctcc cagatttctt ttacattaac taaaaagtct    60
tatcacacaa tctcataaaa tttatgtaat ttcatttaat tttagccaca aatcatcttc    120 aaa atg acg agg att ttg aca gct ttc aaa gtg gtg agg aca ctg aag   168
    Met Thr Arg Ile Leu Thr Ala Phe Lys Val Val Arg Thr Leu Lys
    1               5                   10                  15 act ggt ttt ggc ttt acc aat gtg act gca cac caa aaa tgg aaa ttt   216
Thr Gly Phe Gly Phe Thr Asn Val Thr Ala His Gln Lys Trp Lys Phe
                20                  25                  30 tca aga cct ggc atc agg ctc ctt tct gtc aag gca cag aca gca cac   264
Ser Arg Pro Gly Ile Arg Leu Leu Ser Val Lys Ala Gln Thr Ala His
            35                  40                  45
```

```
att gtc ctg gaa gat gga act aag atg aaa ggt tac tcc ttt ggc cat      312
Ile Val Leu Glu Asp Gly Thr Lys Met Lys Gly Tyr Ser Phe Gly His
         50                  55                  60 cca tcc tct gtt gct ggt gaa gtg gtt ttt aat act ggc ctg gga ggg      360
Pro Ser Ser Val Ala Gly Glu Val Val Phe Asn Thr Gly Leu Gly Gly
 65                  70                  75 tac cca gaa gct att act gac cct gcc tac aaa gga cag att ctc aca      408
Tyr Pro Glu Ala Ile Thr Asp Pro Ala Tyr Lys Gly Gln Ile Leu Thr
 80                  85                  90                  95 atg gcc aac cct att att ggg aat ggt gga gct cct gat act act gct      456
Met Ala Asn Pro Ile Ile Gly Asn Gly Gly Ala Pro Asp Thr Thr Ala
                100                 105                 110 ctg gat gaa ctg gga ctt agc aaa tat ttg gag tct aat gga atc aag      504
Leu Asp Glu Leu Gly Leu Ser Lys Tyr Leu Glu Ser Asn Gly Ile Lys
        115                 120                 125 gtt tca ggt ttg ctg gtg ctg gat tat agt aaa gac tac aac cac tgg      552
Val Ser Gly Leu Leu Val Leu Asp Tyr Ser Lys Asp Tyr Asn His Trp
        130                 135                 140 ctg gct acc aag agt tta ggg caa tgg cta cag gaa gaa aag gtt cct      600
Leu Ala Thr Lys Ser Leu Gly Gln Trp Leu Gln Glu Glu Lys Val Pro
        145                 150                 155 gca att tat gga gtg gac aca aga atg ctg act aaa ata att cgg gat      648
Ala Ile Tyr Gly Val Asp Thr Arg Met Leu Thr Lys Ile Ile Arg Asp
160                 165                 170                 175 aag ggt acc atg ctt ggg aag att gaa ttt gaa ggt cag cct gtg gat      696
Lys Gly Thr Met Leu Gly Lys Ile Glu Phe Glu Gly Gln Pro Val Asp
                180                 185                 190 ttt gtg gat cca aat aaa cag aat ttg att gct gag gtt tca acc aag      744
Phe Val Asp Pro Asn Lys Gln Asn Leu Ile Ala Glu Val Ser Thr Lys
                195                 200                 205 gat gtc aaa gtg tac ggc aaa gga aac ccc aca aaa gtg gta gct gta      792
Asp Val Lys Val Tyr Gly Lys Gly Asn Pro Thr Lys Val Val Ala Val
        210                 215                 220 gac tgt ggg att aaa aac aat gta atc cgc ctg cta gta aag cga gga      840
Asp Cys Gly Ile Lys Asn Asn Val Ile Arg Leu Leu Val Lys Arg Gly
        225                 230                 235 gct gaa gtg cac tta gtt ccc tgg aac cat gat ttc acc aag atg gag      888
Ala Glu Val His Leu Val Pro Trp Asn His Asp Phe Thr Lys Met Glu
240                 245                 250                 255 tat gat ggg att ttg atc gcg gga gga ccg ggg aac cca gct ctt gca      936
Tyr Asp Gly Ile Leu Ile Ala Gly Gly Pro Gly Asn Pro Ala Leu Ala
                260                 265                 270 gaa cca cta att cag aat gtc aga aag att ttg gag agt gat cgc aag      984
Glu Pro Leu Ile Gln Asn Val Arg Lys Ile Leu Glu Ser Asp Arg Lys
                275                 280                 285 gag cca ttg ttt gga atc agt aca gga aac tta ata aca gga ttg gct     1032
Glu Pro Leu Phe Gly Ile Ser Thr Gly Asn Leu Ile Thr Gly Leu Ala
        290                 295                 300 gct ggt gcc aaa acc tac aag atg tcc atg gcc aac aga ggg cag aat     1080
Ala Gly Ala Lys Thr Tyr Lys Met Ser Met Ala Asn Arg Gly Gln Asn
305                 310                 315 cag cct gtt ttg aat atc aca aac aaa cag gct ttc att act gct cag     1128
Gln Pro Val Leu Asn Ile Thr Asn Lys Gln Ala Phe Ile Thr Ala Gln
320                 325                 330                 335 aat cat ggc tat gcc ttg gac aac acc ctc cct gct ggc tgg aaa cca     1176
Asn His Gly Tyr Ala Leu Asp Asn Thr Leu Pro Ala Gly Trp Lys Pro
                340                 345                 350 ctt ttt gtg aat gtc aac gat caa aca aat gag ggg att atg cat gag     1224
Leu Phe Val Asn Val Asn Asp Gln Thr Asn Glu Gly Ile Met His Glu
```

| | | | | | | | | | | | | | | | | |
|---|---|---|---|---|---|---|---|---|---|---|---|---|---|---|---|---|
| | | | 355 | | | | | 360 | | | | | 365 | | | |
| agc | aaa | ccc | ttc | ttc | gct | gtg | cag | ttc | cac | cca | gag | gtc | acc | ccg | ggg | 1272 |
| Ser | Lys | Pro | Phe | Phe | Ala | Val | Gln | Phe | His | Pro | Glu | Val | Thr | Pro | Gly | |
| | | 370 | | | | | 375 | | | | | 380 | | | | |
| cca | ata | gac | act | gag | tac | ctg | ttt | gat | tcc | ttt | ttc | tca | ctg | ata | aag | 1320 |
| Pro | Ile | Asp | Thr | Glu | Tyr | Leu | Phe | Asp | Ser | Phe | Phe | Ser | Leu | Ile | Lys | |
| | | 385 | | | | | 390 | | | | | 395 | | | | |
| aaa | gga | aaa | gct | acc | acc | att | aca | tca | gtc | tta | ccg | aag | cca | gca | cta | 1368 |
| Lys | Gly | Lys | Ala | Thr | Thr | Ile | Thr | Ser | Val | Leu | Pro | Lys | Pro | Ala | Leu | |
| 400 | | | | | 405 | | | | | 410 | | | | | 415 | |
| gtt | gca | tct | cgg | gtt | gag | gtt | tcc | aaa | gtc | ctt | att | cta | gga | tca | gga | 1416 |
| Val | Ala | Ser | Arg | Val | Glu | Val | Ser | Lys | Val | Leu | Ile | Leu | Gly | Ser | Gly | |
| | | | | 420 | | | | | 425 | | | | | 430 | | |
| ggt | ctg | tcc | att | ggt | cag | gct | gga | gaa | ttt | gat | tac | tca | gga | tct | caa | 1464 |
| Gly | Leu | Ser | Ile | Gly | Gln | Ala | Gly | Glu | Phe | Asp | Tyr | Ser | Gly | Ser | Gln | |
| | | | | | 435 | | | | | 440 | | | | | 445 | |
| gct | gta | aaa | gcc | atg | aag | gaa | gaa | aat | gtc | aaa | act | gtt | ctg | atg | aac | 1512 |
| Ala | Val | Lys | Ala | Met | Lys | Glu | Glu | Asn | Val | Lys | Thr | Val | Leu | Met | Asn | |
| | | 450 | | | | | 455 | | | | | 460 | | | | |
| cca | aac | att | gca | tca | gtc | cag | acc | aat | gag | gtg | ggc | tta | aag | caa | gcg | 1560 |
| Pro | Asn | Ile | Ala | Ser | Val | Gln | Thr | Asn | Glu | Val | Gly | Leu | Lys | Gln | Ala | |
| | | 465 | | | | | 470 | | | | | 475 | | | | |
| gat | act | gtc | tac | ttt | ctt | ccc | atc | acc | cct | cag | ttt | gtc | aca | gag | gtc | 1608 |
| Asp | Thr | Val | Tyr | Phe | Leu | Pro | Ile | Thr | Pro | Gln | Phe | Val | Thr | Glu | Val | |
| 480 | | | | | 485 | | | | | 490 | | | | | 495 | |
| atc | aag | gca | gaa | cag | cca | gat | ggg | tta | att | ctg | ggc | atg | ggt | ggc | cag | 1656 |
| Ile | Lys | Ala | Glu | Gln | Pro | Asp | Gly | Leu | Ile | Leu | Gly | Met | Gly | Gly | Gln | |
| | | | | 500 | | | | | 505 | | | | | 510 | | |
| aca | gct | ctg | aac | tgt | gga | gtg | gaa | cta | ttc | aag | aga | ggt | gtg | ctc | aag | 1704 |
| Thr | Ala | Leu | Asn | Cys | Gly | Val | Glu | Leu | Phe | Lys | Arg | Gly | Val | Leu | Lys | |
| | | | 515 | | | | | 520 | | | | | 525 | | | |
| gaa | tat | ggt | gtg | aaa | gtc | ctg | gga | act | tca | gtt | gag | tcc | att | atg | gct | 1752 |
| Glu | Tyr | Gly | Val | Lys | Val | Leu | Gly | Thr | Ser | Val | Glu | Ser | Ile | Met | Ala | |
| | | 530 | | | | | 535 | | | | | 540 | | | | |
| acg | gaa | gac | agg | cag | ctg | ttt | tca | gat | aaa | cta | aat | gag | atc | aat | gaa | 1800 |
| Thr | Glu | Asp | Arg | Gln | Leu | Phe | Ser | Asp | Lys | Leu | Asn | Glu | Ile | Asn | Glu | |
| | | 545 | | | | | 550 | | | | | 555 | | | | |
| aag | att | gct | cca | agt | ttt | gca | gtg | gaa | tcg | att | gag | gat | gca | ctg | aag | 1848 |
| Lys | Ile | Ala | Pro | Ser | Phe | Ala | Val | Glu | Ser | Ile | Glu | Asp | Ala | Leu | Lys | |
| 560 | | | | | 565 | | | | | 570 | | | | | 575 | |
| gca | gca | gac | acc | att | ggc | tac | cca | gtg | atg | atc | cgt | tcc | gcc | tat | gca | 1896 |
| Ala | Ala | Asp | Thr | Ile | Gly | Tyr | Pro | Val | Met | Ile | Arg | Ser | Ala | Tyr | Ala | |
| | | | | 580 | | | | | 585 | | | | | 590 | | |
| ctg | ggt | ggg | tta | ggc | tca | ggc | atc | tgt | ccc | aac | aga | gag | act | ttg | atg | 1944 |
| Leu | Gly | Gly | Leu | Gly | Ser | Gly | Ile | Cys | Pro | Asn | Arg | Glu | Thr | Leu | Met | |
| | | | 595 | | | | | 600 | | | | | 605 | | | |
| gac | ctc | agc | aca | aag | gcc | ttt | gct | atg | acc | aac | caa | att | ctg | gtg | gag | 1992 |
| Asp | Leu | Ser | Thr | Lys | Ala | Phe | Ala | Met | Thr | Asn | Gln | Ile | Leu | Val | Glu | |
| | | 610 | | | | | 615 | | | | | 620 | | | | |
| aag | tca | gtg | aca | ggt | tgg | aaa | gaa | ata | gaa | tat | gaa | gtg | gtt | cga | gat | 2040 |
| Lys | Ser | Val | Thr | Gly | Trp | Lys | Glu | Ile | Glu | Tyr | Glu | Val | Val | Arg | Asp | |
| | | 625 | | | | | 630 | | | | | 635 | | | | |
| gct | gat | gac | aat | tgt | gtc | act | gtc | tgt | aac | atg | gaa | aat | gtt | gat | gcc | 2088 |
| Ala | Asp | Asp | Asn | Cys | Val | Thr | Val | Cys | Asn | Met | Glu | Asn | Val | Asp | Ala | |
| 640 | | | | | 645 | | | | | 650 | | | | | 655 | |
| atg | ggt | gtt | cac | aca | ggt | gac | tca | gtt | gtt | gtg | gct | cct | gcc | cag | aca | 2136 |
| Met | Gly | Val | His | Thr | Gly | Asp | Ser | Val | Val | Val | Ala | Pro | Ala | Gln | Thr | |
| | | | | 660 | | | | | 665 | | | | | 670 | | |
| ctc | tcc | aat | gcc | gag | ttt | cag | atg | ttg | aga | cgt | act | tca | atc | aat | gtt | 2184 |

```
                                                                              -continued Leu Ser Asn Ala Glu Phe Gln Met Leu Arg Arg Thr Ser Ile Asn Val
                                    675                 680                 685 gtt cgc cac ttg ggc att gtg ggt gaa tgc aac att cag ttt gcc ctt                2232
Val Arg His Leu Gly Ile Val Gly Glu Cys Asn Ile Gln Phe Ala Leu
            690                 695                 700 cat cct acc tca atg gaa tac tgc atc att gaa gtg aat gcc aga ctg                2280
His Pro Thr Ser Met Glu Tyr Cys Ile Ile Glu Val Asn Ala Arg Leu
    705                 710                 715 tcc cga agc tct gct ctg gcc tca aaa gcc act ggc tac cca ttg gca                2328
Ser Arg Ser Ser Ala Leu Ala Ser Lys Ala Thr Gly Tyr Pro Leu Ala
720                 725                 730                 735 ttc att gct gca aag att gcc cta gga atc cca ctt cca gaa att aag                2376
Phe Ile Ala Ala Lys Ile Ala Leu Gly Ile Pro Leu Pro Glu Ile Lys
                740                 745                 750 aac gtc gta tcc ggg aag aca tca gcc tgt ttt gaa cct agc ctg gat                2424
Asn Val Val Ser Gly Lys Thr Ser Ala Cys Phe Glu Pro Ser Leu Asp
            755                 760                 765 tac atg gtc acc aag att ccc cgc tgg gat ctt gac cgt ttt cat gga                2472
Tyr Met Val Thr Lys Ile Pro Arg Trp Asp Leu Asp Arg Phe His Gly
        770                 775                 780 aca tct agc cga att ggt agc tct atg aaa agt gta gga gag gtc atg                2520
Thr Ser Ser Arg Ile Gly Ser Ser Met Lys Ser Val Gly Glu Val Met
    785                 790                 795 gct att ggt cgt acc ttt gag gag agt ttc cag aaa gct tta cgg atg                2568
Ala Ile Gly Arg Thr Phe Glu Glu Ser Phe Gln Lys Ala Leu Arg Met
800                 805                 810                 815 tgc cac cca tct ata gaa ggt ttc act ccc cgt ctc cca atg aac aaa                2616
Cys His Pro Ser Ile Glu Gly Phe Thr Pro Arg Leu Pro Met Asn Lys
                820                 825                 830 gaa tgg cca tct aat tta gat ctt aga aaa gag ttg tct gaa cca agc                2664
Glu Trp Pro Ser Asn Leu Asp Leu Arg Lys Glu Leu Ser Glu Pro Ser
            835                 840                 845 agc acg cgt atc tat gcc att gcc aag gcc att gat gac aac atg tcc                2712
Ser Thr Arg Ile Tyr Ala Ile Ala Lys Ala Ile Asp Asp Asn Met Ser
        850                 855                 860 ctt gat gag att gag aag ctc aca tac att gac aag tgg ttt ttg tat                2760
Leu Asp Glu Ile Glu Lys Leu Thr Tyr Ile Asp Lys Trp Phe Leu Tyr
    865                 870                 875 aag atg cgt gat att tta aac atg gaa aag aca ctg aaa ggg ctc aac                2808
Lys Met Arg Asp Ile Leu Asn Met Glu Lys Thr Leu Lys Gly Leu Asn
880                 885                 890                 895 agt gag tcc atg aca gaa gaa acc ctg aaa agg gca aag gag att ggg                2856
Ser Glu Ser Met Thr Glu Glu Thr Leu Lys Arg Ala Lys Glu Ile Gly
                900                 905                 910 ttc tca gat aag cag att tca aaa tgc ctt ggg ctc act gag gcc cag                2904
Phe Ser Asp Lys Gln Ile Ser Lys Cys Leu Gly Leu Thr Glu Ala Gln
            915                 920                 925 aca agg gag ctg agg tta aag aaa aac atc cac cct tgg gtt aaa cag                2952
Thr Arg Glu Leu Arg Leu Lys Lys Asn Ile His Pro Trp Val Lys Gln
        930                 935                 940 att gat aca ctg gct gca gaa tac cca tca gta aca aac tat ctc tat                3000
Ile Asp Thr Leu Ala Ala Glu Tyr Pro Ser Val Thr Asn Tyr Leu Tyr
    945                 950                 955 gtt acc tac aat ggt cag gag cat gat gtc aat ttt gat gac cat gga                3048
Val Thr Tyr Asn Gly Gln Glu His Asp Val Asn Phe Asp Asp His Gly
960                 965                 970                 975 atg atg gtg cta ggc tgt ggt cca tat cac att ggc agc agt gtg gaa                3096
Met Met Val Leu Gly Cys Gly Pro Tyr His Ile Gly Ser Ser Val Glu
                980                 985                 990
```

-continued

| | | |
|---|---|---|
| ttt gat tgg tgt gct gtc tct agt atc cgc aca ctg cgt caa ctt ggc<br>Phe Asp Trp Cys Ala Val Ser Ser Ile Arg Thr Leu Arg Gln Leu Gly<br>           995                       1000                        1005 | 3144 |

```
ttt gat tgg tgt gct gtc tct agt atc cgc aca ctg cgt caa ctt ggc      3144
Phe Asp Trp Cys Ala Val Ser Ser Ile Arg Thr Leu Arg Gln Leu Gly
        995                 1000                1005 aag aag acg gtg gtg gtg aat tgc aat cct gag act gtg agc aca          3189
Lys Lys Thr Val Val Val Asn Cys Asn Pro Glu Thr Val Ser Thr
            1010                1015                1020 gac ttt gat gag tgt gac aaa ctg tac ttt gaa gag ttg tcc ttg          3234
Asp Phe Asp Glu Cys Asp Lys Leu Tyr Phe Glu Glu Leu Ser Leu
            1025                1030                1035 gag aga atc cta gac atc tac cat cag gag gca tgt ggt ggc tgc          3279
Glu Arg Ile Leu Asp Ile Tyr His Gln Glu Ala Cys Gly Gly Cys
            1040                1045                1050 atc ata tca gtt gga ggc cag att cca aac aac ctg gca gtt cct          3324
Ile Ile Ser Val Gly Gly Gln Ile Pro Asn Asn Leu Ala Val Pro
            1055                1060                1065 cta tac aag aat ggt gtc aag atc atg ggc aca agc ccc ctg cag          3369
Leu Tyr Lys Asn Gly Val Lys Ile Met Gly Thr Ser Pro Leu Gln
            1070                1075                1080 atc gac agg gct gag gat cgc tcc atc ttc tca gct gtc ttg gat          3414
Ile Asp Arg Ala Glu Asp Arg Ser Ile Phe Ser Ala Val Leu Asp
            1085                1090                1095 gag ctg aag gtg gct cag gca cct tgg aaa gct gtt aat act ttg          3459
Glu Leu Lys Val Ala Gln Ala Pro Trp Lys Ala Val Asn Thr Leu
            1100                1105                1110 aat gaa gca ctg gaa ttt gca aag tct gtg gac tac ccc tgc ttg          3504
Asn Glu Ala Leu Glu Phe Ala Lys Ser Val Asp Tyr Pro Cys Leu
            1115                1120                1125 ttg agg cct tcc tat gtt ttg agt ggg tct gct atg aat gtg gta          3549
Leu Arg Pro Ser Tyr Val Leu Ser Gly Ser Ala Met Asn Val Val
            1130                1135                1140 ttc tct gag gat gag atg aaa aaa ttc cta gaa gag gcg act aga          3594
Phe Ser Glu Asp Glu Met Lys Lys Phe Leu Glu Glu Ala Thr Arg
            1145                1150                1155 gtt tct cag gag cac cca gtg gtc ctg aca aaa ttt gtt gaa ggg          3639
Val Ser Gln Glu His Pro Val Val Leu Thr Lys Phe Val Glu Gly
            1160                1165                1170 gcc cga gaa gta gaa atg gac gct gtt ggc aaa gat gga agg gtt          3684
Ala Arg Glu Val Glu Met Asp Ala Val Gly Lys Asp Gly Arg Val
            1175                1180                1185 atc tct cat gcc atc tct gaa cat gtt gaa gat gca ggt gtc cac          3729
Ile Ser His Ala Ile Ser Glu His Val Glu Asp Ala Gly Val His
            1190                1195                1200 tcg gga gat gcc act ctg atg ctg ccc aca caa acc atc agc caa          3774
Ser Gly Asp Ala Thr Leu Met Leu Pro Thr Gln Thr Ile Ser Gln
            1205                1210                1215 ggg gcc att gaa aag gtg aag gat gct acc cgg aag att gca aag          3819
Gly Ala Ile Glu Lys Val Lys Asp Ala Thr Arg Lys Ile Ala Lys
            1220                1225                1230 gct ttt gcc atc tct ggt cca ttc aac gtc caa ttt ctt gtc aaa          3864
Ala Phe Ala Ile Ser Gly Pro Phe Asn Val Gln Phe Leu Val Lys
            1235                1240                1245 gga aat gat gtc ttg gtg att gag tgt aac ttg aga gct tct cga          3909
Gly Asn Asp Val Leu Val Ile Glu Cys Asn Leu Arg Ala Ser Arg
            1250                1255                1260 tcc ttc ccc ttt gtt tcc aag act ctt ggg gtt gac ttc att gat          3954
Ser Phe Pro Phe Val Ser Lys Thr Leu Gly Val Asp Phe Ile Asp
            1265                1270                1275 gtg gcc acc aag gtg atg att gga gag aat gtt gat gag aaa cat          3999
Val Ala Thr Lys Val Met Ile Gly Glu Asn Val Asp Glu Lys His
            1280                1285                1290
```

```
ctt cca aca ttg gac cat ccc ata att cct gct gac tat gtt gca      4044
Leu Pro Thr Leu Asp His Pro Ile Ile Pro Ala Asp Tyr Val Ala
        1295            1300            1305 att aag gct ccc atg ttt tcc tgg ccc cgg ttg agg gat gct gac      4089
Ile Lys Ala Pro Met Phe Ser Trp Pro Arg Leu Arg Asp Ala Asp
        1310            1315            1320 ccc att ctg aga tgt gag atg gct tcc act gga gag gtg gct tgc      4134
Pro Ile Leu Arg Cys Glu Met Ala Ser Thr Gly Glu Val Ala Cys
        1325            1330            1335 ttt ggt gaa ggt att cat aca gcc ttc cta aag gca atg ctt tcc      4179
Phe Gly Glu Gly Ile His Thr Ala Phe Leu Lys Ala Met Leu Ser
        1340            1345            1350 aca gga ttt aag ata ccc cag aaa ggc atc ctg ata ggc atc cag      4224
Thr Gly Phe Lys Ile Pro Gln Lys Gly Ile Leu Ile Gly Ile Gln
        1355            1360            1365 caa tca ttc cgg cca aga ttc ctt ggt gtg gct gaa caa tta cac      4269
Gln Ser Phe Arg Pro Arg Phe Leu Gly Val Ala Glu Gln Leu His
        1370            1375            1380 aat gaa ggt ttc aag ctg ttt gcc acg gaa gcc aca tca gac tgg      4314
Asn Glu Gly Phe Lys Leu Phe Ala Thr Glu Ala Thr Ser Asp Trp
        1385            1390            1395 ctc aac gcc aac aat gtc cct gcc acc cca gtg gca tgg ccg tct      4359
Leu Asn Ala Asn Asn Val Pro Ala Thr Pro Val Ala Trp Pro Ser
        1400            1405            1410 caa gaa gga cag aat ccc agc ctc tct tcc atc aga aaa ttg att      4404
Gln Glu Gly Gln Asn Pro Ser Leu Ser Ser Ile Arg Lys Leu Ile
        1415            1420            1425 aga gat ggc agc att gac cta gtg att aac ctt ccc aac aac aac      4449
Arg Asp Gly Ser Ile Asp Leu Val Ile Asn Leu Pro Asn Asn Asn
        1430            1435            1440 act aaa ttt gtc cat gat aat tat gtg att cgg agg aca gct gtt      4494
Thr Lys Phe Val His Asp Asn Tyr Val Ile Arg Arg Thr Ala Val
        1445            1450            1455 gat agt gga atc cct ctc ctc act aat ttt cag gtg acc aaa ctt      4539
Asp Ser Gly Ile Pro Leu Leu Thr Asn Phe Gln Val Thr Lys Leu
        1460            1465            1470 ttt gct gaa gct gtg cag aaa tct cgc aag gtg gac tcc aag agt      4584
Phe Ala Glu Ala Val Gln Lys Ser Arg Lys Val Asp Ser Lys Ser
        1475            1480            1485 ctt ttc cac tac agg cag tac agt gct gga aaa gca gca tag          4626
Leu Phe His Tyr Arg Gln Tyr Ser Ala Gly Lys Ala Ala
        1490            1495            1500 agatgcagac accccagccc cattattaaa tcaacctgag ccacatgtta tctaaaggaa   4686
ctgattcaca actttctcag agatgaatat tgataactaa acttcattttc agtttacttt   4746
gttatgcctt aatattctgt gtcttttgca attaaattgt cagtcacttc ttcaaaacct   4806
tacagtcctt cctaagttac tcttcatgag atttcatcca tttactaata ctgtattttt   4866
ggtggactag gcttgcctat gtgcttatgt gtagcttttt acttttttatg gtgctgatta   4926
atggtgatca aggtaggaaa agttgctgtt ctatttttctg aactctttct atactttaag   4986
atactctatt tttaaaacac tatctgcaaa ctcaggacac tttaacaggg cagaatactc   5046
taaaacttg ataaaatgaa atatagattt aatttatgaa ccttccatca tgatgtttgt   5106
gtattgcttc tttttggatc ctcattctca cccatttggc taatccagga atattgttat   5166
cccttcccat tatattgaag ttgagaaatg tgacagaggc atttagagta tggacttttc   5226
ttttctttttt cttttttcttt ttttcttttt gagatggagt cacactctcc aggctggagt   5286
```

-continued

```
gcagtggcac aatctcggct cactgcaatt tgcgtctccc aagttcaagc gattctcctg    5346
ctttagacta tggatttctt taaggaatac tggtttgcag ttttgttttc tggactatat    5406
cagcagatgg tagacagtgt ttatgtagat gtgttgttgt ttttatcatt ggattttaac    5466
ttggcccgag tgaaataatc agatttttgt cattcacact ctcccccagt tttggaataa    5526
cttggaagta aggttcattc ccttaagacg atggattctg ttgaactatg gggtcccaca    5586
ctgcactatt aattccaccc actgtaaggg caaggacacc attccttcta catataagaa    5646
aaaagtctct ccccaagggc agcctttgtt acttttaaat attttctgtt attacaagtg    5706
ctctaattgt gaacttttaa ataaaatact attaagaggt aaaaaaaaaa aaaaa         5761
```

<210> SEQ ID NO 4
<211> LENGTH: 1500
<212> TYPE: PRT
<213> ORGANISM: Homo sapiens

<400> SEQUENCE: 4

```
Met Thr Arg Ile Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
            180                 185                 190

Val Asp Pro Asn Lys Gln Asn Leu Ile Ala Glu Val Ser Thr Lys Asp
        195                 200                 205

Val Lys Val Tyr Gly Lys Gly Asn Pro Thr Lys Val Val Ala Val Asp
    210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
            260                 265                 270

Pro Leu Ile Gln Asn Val Arg Lys Ile Leu Glu Ser Asp Arg Lys Glu
        275                 280                 285

Pro Leu Phe Gly Ile Ser Thr Gly Asn Leu Ile Thr Gly Leu Ala Ala
```

-continued

```
            290                 295                 300
Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
                340                 345                 350

Phe Val Asn Val Asn Asp Gln Thr Asn Glu Gly Ile Met His Glu Ser
                355                 360                 365

Lys Pro Phe Phe Ala Val Gln Phe His Pro Glu Val Thr Pro Gly Pro
        370                 375                 380

Ile Asp Thr Glu Tyr Leu Phe Asp Ser Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
                420                 425                 430

Leu Ser Ile Gly Gln Ala Gly Glu Phe Asp Tyr Ser Gly Ser Gln Ala
                435                 440                 445

Val Lys Ala Met Lys Glu Glu Asn Val Lys Thr Val Leu Met Asn Pro
        450                 455                 460

Asn Ile Ala Ser Val Gln Thr Asn Glu Val Gly Leu Lys Gln Ala Asp
465                 470                 475                 480

Thr Val Tyr Phe Leu Pro Ile Thr Pro Gln Phe Val Thr Glu Val Ile
                485                 490                 495

Lys Ala Glu Gln Pro Asp Gly Leu Ile Leu Gly Met Gly Gly Gln Thr
                500                 505                 510

Ala Leu Asn Cys Gly Val Glu Leu Phe Lys Arg Gly Val Leu Lys Glu
                515                 520                 525

Tyr Gly Val Lys Val Leu Gly Thr Ser Val Glu Ser Ile Met Ala Thr
                530                 535                 540

Glu Asp Arg Gln Leu Phe Ser Asp Lys Leu Asn Glu Ile Asn Glu Lys
545                 550                 555                 560

Ile Ala Pro Ser Phe Ala Val Glu Ser Ile Glu Asp Ala Leu Lys Ala
                565                 570                 575

Ala Asp Thr Ile Gly Tyr Pro Val Met Ile Arg Ser Ala Tyr Ala Leu
                580                 585                 590

Gly Gly Leu Gly Ser Gly Ile Cys Pro Asn Arg Glu Thr Leu Met Asp
                595                 600                 605

Leu Ser Thr Lys Ala Phe Ala Met Thr Asn Gln Ile Leu Val Glu Lys
        610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Val Ala Pro Ala Gln Thr Leu
                660                 665                 670

Ser Asn Ala Glu Phe Gln Met Leu Arg Arg Thr Ser Ile Asn Val Val
                675                 680                 685

Arg His Leu Gly Ile Val Gly Glu Cys Asn Ile Gln Phe Ala Leu His
        690                 695                 700

Pro Thr Ser Met Glu Tyr Cys Ile Ile Glu Val Asn Ala Arg Leu Ser
705                 710                 715                 720
```

-continued

```
Arg Ser Ser Ala Leu Ala Ser Lys Ala Thr Gly Tyr Pro Leu Ala Phe
            725                 730                 735

Ile Ala Ala Lys Ile Ala Leu Gly Ile Pro Leu Pro Glu Ile Lys Asn
            740                 745                 750

Val Val Ser Gly Lys Thr Ser Ala Cys Phe Glu Pro Ser Leu Asp Tyr
            755                 760             765

Met Val Thr Lys Ile Pro Arg Trp Asp Leu Asp Arg Phe His Gly Thr
    770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
                805                 810                 815

His Pro Ser Ile Glu Gly Phe Thr Pro Arg Leu Pro Met Asn Lys Glu
                820                 825                 830

Trp Pro Ser Asn Leu Asp Leu Arg Lys Glu Leu Ser Glu Pro Ser Ser
                835                 840                 845

Thr Arg Ile Tyr Ala Ile Ala Lys Ala Ile Asp Asp Asn Met Ser Leu
    850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
                885                 890                 895

Glu Ser Met Thr Glu Glu Thr Leu Lys Arg Ala Lys Glu Ile Gly Phe
                900                 905                 910

Ser Asp Lys Gln Ile Ser Lys Cys Leu Gly Leu Thr Glu Ala Gln Thr
            915                 920                 925

Arg Glu Leu Arg Leu Lys Lys Asn Ile His Pro Trp Val Lys Gln Ile
    930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
                980                 985                 990

Asp Trp Cys Ala Val Ser Ser Ile Arg Thr Leu Arg Gln Leu Gly Lys
            995                 1000                1005

Lys Thr Val Val Val Asn Cys Asn Pro Glu Thr Val Ser Thr Asp
    1010                1015                1020

Phe Asp Glu Cys Asp Lys Leu Tyr Phe Glu Glu Leu Ser Leu Glu
    1025                1030                1035

Arg Ile Leu Asp Ile Tyr His Gln Glu Ala Cys Gly Gly Cys Ile
    1040                1045                1050

Ile Ser Val Gly Gly Gln Ile Pro Asn Asn Leu Ala Val Pro Leu
    1055                1060                1065

Tyr Lys Asn Gly Val Lys Ile Met Gly Thr Ser Pro Leu Gln Ile
    1070                1075                1080

Asp Arg Ala Glu Asp Arg Ser Ile Phe Ser Ala Val Leu Asp Glu
    1085                1090                1095

Leu Lys Val Ala Gln Ala Pro Trp Lys Ala Val Asn Thr Leu Asn
    1100                1105                1110

Glu Ala Leu Glu Phe Ala Lys Ser Val Asp Tyr Pro Cys Leu Leu
    1115                1120                1125
```

```
-continued

Arg Pro Ser Tyr Val Leu Ser Gly Ser Ala Met Asn Val Val Phe
    1130                1135                1140

Ser Glu Asp Glu Met Lys Lys Phe Leu Glu Ala Thr Arg Val
    1145                1150                1155

Ser Gln Glu His Pro Val Val Leu Thr Lys Phe Val Glu Gly Ala
    1160                1165                1170

Arg Glu Val Glu Met Asp Ala Val Gly Lys Asp Gly Arg Val Ile
    1175                1180                1185

Ser His Ala Ile Ser Glu His Val Glu Asp Ala Gly Val His Ser
    1190                1195                1200

Gly Asp Ala Thr Leu Met Leu Pro Thr Gln Thr Ile Ser Gln Gly
    1205                1210                1215

Ala Ile Glu Lys Val Lys Asp Ala Thr Arg Lys Ile Ala Lys Ala
    1220                1225                1230

Phe Ala Ile Ser Gly Pro Phe Asn Val Gln Phe Leu Val Lys Gly
    1235                1240                1245

Asn Asp Val Leu Val Ile Glu Cys Asn Leu Arg Ala Ser Arg Ser
    1250                1255                1260

Phe Pro Phe Val Ser Lys Thr Leu Gly Val Asp Phe Ile Asp Val
    1265                1270                1275

Ala Thr Lys Val Met Ile Gly Glu Asn Val Asp Glu Lys His Leu
    1280                1285                1290

Pro Thr Leu Asp His Pro Ile Ile Pro Ala Asp Tyr Val Ala Ile
    1295                1300                1305

Lys Ala Pro Met Phe Ser Trp Pro Arg Leu Arg Asp Ala Asp Pro
    1310                1315                1320

Ile Leu Arg Cys Glu Met Ala Ser Thr Gly Glu Val Ala Cys Phe
    1325                1330                1335

Gly Glu Gly Ile His Thr Ala Phe Leu Lys Ala Met Leu Ser Thr
    1340                1345                1350

Gly Phe Lys Ile Pro Gln Lys Gly Ile Leu Ile Gly Ile Gln Gln
    1355                1360                1365

Ser Phe Arg Pro Arg Phe Leu Gly Val Ala Glu Gln Leu His Asn
    1370                1375                1380

Glu Gly Phe Lys Leu Phe Ala Thr Glu Ala Thr Ser Asp Trp Leu
    1385                1390                1395

Asn Ala Asn Asn Val Pro Ala Thr Pro Val Ala Trp Pro Ser Gln
    1400                1405                1410

Glu Gly Gln Asn Pro Ser Leu Ser Ser Ile Arg Lys Leu Ile Arg
    1415                1420                1425

Asp Gly Ser Ile Asp Leu Val Ile Asn Leu Pro Asn Asn Asn Thr
    1430                1435                1440

Lys Phe Val His Asp Asn Tyr Val Ile Arg Arg Thr Ala Val Asp
    1445                1450                1455

Ser Gly Ile Pro Leu Leu Thr Asn Phe Gln Val Thr Lys Leu Phe
    1460                1465                1470

Ala Glu Ala Val Gln Lys Ser Arg Lys Val Asp Ser Lys Ser Leu
    1475                1480                1485

Phe His Tyr Arg Gln Tyr Ser Ala Gly Lys Ala Ala
    1490                1495                1500

<210> SEQ ID NO 5
<211> LENGTH: 495
<212> TYPE: DNA
```

```
<213> ORGANISM: Homo sapiens
<220> FEATURE:
<221> NAME/KEY: misc_feature
<222> LOCATION: (1)..(495)
<223> OTHER INFORMATION: n is a, c, g, or t

<400> SEQUENCE: 5
ctacttctca tgttcagcaa tttcttcttc tttatgtttt aaattacatg ttccataaaa      60
ataagaaatn cactgtgata cggtaattga ttttttcatt ttaaatgcag ctgtttgcca     120
cggaagccac atcagactgg ctcaacgcca acaatgtccc tgccacccca gtggcatggc     180
cgtctcaaga aggacagaat cccagcctct cttccatcag aaagtaagaa ctaggcatac     240
tgttttctga ataatttag aggattaact ttgagaacca gtatatgaat attcaccttg      300
cttgattgca agtcttttaa aacaaattta aaatgaata catttgtgga tgattgtcaa      360
gtttcactct ccatcactat ggaatacata acgtcatgtg tacatggtga tatgaaacgt     420
gtttcaaaat acttcttagt aaggatactt tccttgacgg aaacaagtga gagtatgaag     480
aatgtaatgc agcac                                                     495

<210> SEQ ID NO 6
<211> LENGTH: 20
<212> TYPE: DNA
<213> ORGANISM: Homo sapiens

<400> SEQUENCE: 6
agctgtttgc cacggaagcc                                                 20

<210> SEQ ID NO 7
<211> LENGTH: 28
<212> TYPE: DNA
<213> ORGANISM: Homo sapiens

<400> SEQUENCE: 7
cccagcctct cttccatcag aaagtaag                                        28

<210> SEQ ID NO 8
<211> LENGTH: 20
<212> TYPE: DNA
<213> ORGANISM: Homo sapiens

<400> SEQUENCE: 8
cacggaagcc acatcagact                                                 20

<210> SEQ ID NO 9
<211> LENGTH: 21
<212> TYPE: DNA
<213> ORGANISM: Homo sapiens

<400> SEQUENCE: 9
ttctgatgga agagaggctt g                                               21

<210> SEQ ID NO 10
<211> LENGTH: 24
<212> TYPE: DNA
<213> ORGANISM: Homo sapiens

<400> SEQUENCE: 10
agagtgaaac ttgacaatca tcca                                            24

<210> SEQ ID NO 11
<211> LENGTH: 5761
```

```
<212> TYPE: DNA
<213> ORGANISM: Homo sapiens
<220> FEATURE:
<221> NAME/KEY: CDS
<222> LOCATION: (124)..(4626)

<400> SEQUENCE: 11
gtcagcctta aacactgact gcacccctcc cagatttctt ttacattaac taaaaagtct      60
tatcacacaa tctcataaaa tttatgtaat ttcatttaat tttagccaca aatcatcttc     120
```

| | | | | | | | | | | | | | | | | |
|---|---|---|---|---|---|---|---|---|---|---|---|---|---|---|---|---|
| aaa | atg | acg | agg | tta | ttg | aca | gct | ttc | aaa | gtg | gtg | agg | aca | ctg | aag | 168 |
| | Met | Thr | Arg | Leu | Leu | Thr | Ala | Phe | Lys | Val | Val | Arg | Thr | Leu | Lys | |
| | 1 | | | 5 | | | | | 10 | | | | | 15 | | |
| act | ggt | ttt | ggc | ttt | acc | aat | gtg | act | gca | cac | caa | aaa | tgg | aaa | ttt | 216 |
| Thr | Gly | Phe | Gly | Phe | Thr | Asn | Val | Thr | Ala | His | Gln | Lys | Trp | Lys | Phe | |
| | | | 20 | | | | | 25 | | | | | 30 | | | |
| tca | aga | cct | ggc | atc | agg | ctc | ctt | tct | gtc | aag | gca | cag | aca | gca | cac | 264 |
| Ser | Arg | Pro | Gly | Ile | Arg | Leu | Leu | Ser | Val | Lys | Ala | Gln | Thr | Ala | His | |
| | | | 35 | | | | | 40 | | | | | 45 | | | |
| att | gtc | ctg | gaa | gat | gga | act | aag | atg | aaa | ggt | tac | tcc | ttt | ggc | cat | 312 |
| Ile | Val | Leu | Glu | Asp | Gly | Thr | Lys | Met | Lys | Gly | Tyr | Ser | Phe | Gly | His | |
| | | 50 | | | | | 55 | | | | | 60 | | | | |
| cca | tcc | tct | gtt | gct | ggt | gaa | gtg | gtt | ttt | aat | act | ggc | ctg | gga | ggg | 360 |
| Pro | Ser | Ser | Val | Ala | Gly | Glu | Val | Val | Phe | Asn | Thr | Gly | Leu | Gly | Gly | |
| | 65 | | | | | 70 | | | | | 75 | | | | | |
| tac | cca | gaa | gct | att | act | gac | cct | gcc | tac | aaa | gga | cag | att | ctc | aca | 408 |
| Tyr | Pro | Glu | Ala | Ile | Thr | Asp | Pro | Ala | Tyr | Lys | Gly | Gln | Ile | Leu | Thr | |
| 80 | | | | | 85 | | | | | 90 | | | | | 95 | |
| atg | gcc | aac | cct | att | att | ggg | aat | ggt | gga | gct | cct | gat | act | act | gct | 456 |
| Met | Ala | Asn | Pro | Ile | Ile | Gly | Asn | Gly | Gly | Ala | Pro | Asp | Thr | Thr | Ala | |
| | | | 100 | | | | | 105 | | | | | 110 | | | |
| ctg | gat | gaa | ctg | gga | ctt | agc | aaa | tat | ttg | gag | tct | aat | gga | atc | aag | 504 |
| Leu | Asp | Glu | Leu | Gly | Leu | Ser | Lys | Tyr | Leu | Glu | Ser | Asn | Gly | Ile | Lys | |
| | | | 115 | | | | | 120 | | | | | 125 | | | |
| gtt | tca | ggt | ttg | ctg | gtg | ctg | gat | tat | agt | aaa | gac | tac | aac | cac | tgg | 552 |
| Val | Ser | Gly | Leu | Leu | Val | Leu | Asp | Tyr | Ser | Lys | Asp | Tyr | Asn | His | Trp | |
| | | 130 | | | | | 135 | | | | | 140 | | | | |
| ctg | gct | acc | aag | agt | tta | ggg | caa | tgg | cta | cag | gaa | gaa | aag | gtt | cct | 600 |
| Leu | Ala | Thr | Lys | Ser | Leu | Gly | Gln | Trp | Leu | Gln | Glu | Glu | Lys | Val | Pro | |
| | 145 | | | | | 150 | | | | | 155 | | | | | |
| gca | att | tat | gga | gtg | gac | aca | aga | atg | ctg | act | aaa | ata | att | cgg | gat | 648 |
| Ala | Ile | Tyr | Gly | Val | Asp | Thr | Arg | Met | Leu | Thr | Lys | Ile | Ile | Arg | Asp | |
| 160 | | | | | 165 | | | | | 170 | | | | | 175 | |
| aag | ggt | acc | atg | ctt | ggg | aag | att | gaa | ttt | gaa | ggt | cag | cct | gtg | gat | 696 |
| Lys | Gly | Thr | Met | Leu | Gly | Lys | Ile | Glu | Phe | Glu | Gly | Gln | Pro | Val | Asp | |
| | | | 180 | | | | | 185 | | | | | 190 | | | |
| ttt | gtg | gat | cca | aat | aaa | cag | aat | ttg | att | gct | gag | gtt | tca | acc | aag | 744 |
| Phe | Val | Asp | Pro | Asn | Lys | Gln | Asn | Leu | Ile | Ala | Glu | Val | Ser | Thr | Lys | |
| | | | 195 | | | | | 200 | | | | | 205 | | | |
| gat | gtc | aaa | gtg | tac | ggc | aaa | gga | aac | ccc | aca | aaa | gtg | gta | gct | gta | 792 |
| Asp | Val | Lys | Val | Tyr | Gly | Lys | Gly | Asn | Pro | Thr | Lys | Val | Val | Ala | Val | |
| | | 210 | | | | | 215 | | | | | 220 | | | | |
| gac | tgt | ggg | att | aaa | aac | aat | gta | atc | cgc | ctg | cta | gta | aag | cga | gga | 840 |
| Asp | Cys | Gly | Ile | Lys | Asn | Asn | Val | Ile | Arg | Leu | Leu | Val | Lys | Arg | Gly | |
| | 225 | | | | | 230 | | | | | 235 | | | | | |
| gct | gaa | gtg | cac | tta | gtt | ccc | tgg | aac | cat | gat | ttc | acc | aag | atg | gag | 888 |
| Ala | Glu | Val | His | Leu | Val | Pro | Trp | Asn | His | Asp | Phe | Thr | Lys | Met | Glu | |
| 240 | | | | | 245 | | | | | 250 | | | | | 255 | |
| tat | gat | ggg | att | ttg | atc | gcg | gga | gga | ccg | ggg | aac | cca | gct | ctt | gca | 936 |
| Tyr | Asp | Gly | Ile | Leu | Ile | Ala | Gly | Gly | Pro | Gly | Asn | Pro | Ala | Leu | Ala | |
| | | | 260 | | | | | 265 | | | | | 270 | | | |

```
gaa cca cta att cag aat gtc aga aag att ttg gag agt gat cgc aag        984
Glu Pro Leu Ile Gln Asn Val Arg Lys Ile Leu Glu Ser Asp Arg Lys
            275                 280                 285 gag cca ttg ttt gga atc agt aca gga aac tta ata aca gga ttg gct       1032
Glu Pro Leu Phe Gly Ile Ser Thr Gly Asn Leu Ile Thr Gly Leu Ala
            290                 295                 300 gct ggt gcc aaa acc tac aag atg tcc atg gcc aac aga ggg cag aat       1080
Ala Gly Ala Lys Thr Tyr Lys Met Ser Met Ala Asn Arg Gly Gln Asn
        305                 310                 315 cag cct gtt ttg aat atc aca aac aaa cag gct ttc att act gct cag       1128
Gln Pro Val Leu Asn Ile Thr Asn Lys Gln Ala Phe Ile Thr Ala Gln
320                 325                 330                 335 aat cat ggc tat gcc ttg gac aac acc ctc cct gct ggc tgg aaa cca       1176
Asn His Gly Tyr Ala Leu Asp Asn Thr Leu Pro Ala Gly Trp Lys Pro
                340                 345                 350 ctt ttt gtg aat gtc aac gat caa aca aat gag ggg att atg cat gag       1224
Leu Phe Val Asn Val Asn Asp Gln Thr Asn Glu Gly Ile Met His Glu
                355                 360                 365 agc aaa ccc ttc ttc gct gtg cag ttc cac cca gag gtc acc ccg ggg       1272
Ser Lys Pro Phe Phe Ala Val Gln Phe His Pro Glu Val Thr Pro Gly
            370                 375                 380 cca ata gac act gag tac ctg ttt gat tcc ttt tca ctg ata aag           1320
Pro Ile Asp Thr Glu Tyr Leu Phe Asp Ser Phe Phe Ser Leu Ile Lys
        385                 390                 395 aaa gga aaa gct acc acc att aca tca gtc tta ccg aag cca gca cta       1368
Lys Gly Lys Ala Thr Thr Ile Thr Ser Val Leu Pro Lys Pro Ala Leu
400                 405                 410                 415 gtt gca tct cgg gtt gag gtt tcc aaa gtc ctt att cta gga tca gga       1416
Val Ala Ser Arg Val Glu Val Ser Lys Val Leu Ile Leu Gly Ser Gly
                420                 425                 430 ggt ctg tcc att ggt cag gct gga gaa ttt gat tac tca gga tct caa       1464
Gly Leu Ser Ile Gly Gln Ala Gly Glu Phe Asp Tyr Ser Gly Ser Gln
                435                 440                 445 gct gta aaa gcc atg aag gaa gaa aat gtc aaa act gtt ctg atg aac       1512
Ala Val Lys Ala Met Lys Glu Glu Asn Val Lys Thr Val Leu Met Asn
            450                 455                 460 cca aac att gca tca gtc cag acc aat gag gtg ggc tta aag caa gcg       1560
Pro Asn Ile Ala Ser Val Gln Thr Asn Glu Val Gly Leu Lys Gln Ala
465                 470                 475 gat act gtc tac ttt ctt ccc atc acc cct cag ttt gtc aca gag gtc       1608
Asp Thr Val Tyr Phe Leu Pro Ile Thr Pro Gln Phe Val Thr Glu Val
480                 485                 490                 495 atc aag gca gaa cag cca gat ggg tta att ctg ggc atg ggt ggc cag       1656
Ile Lys Ala Glu Gln Pro Asp Gly Leu Ile Leu Gly Met Gly Gly Gln
                500                 505                 510 aca gct ctg aac tgt gga gtg gaa cta ttc aag aga ggt gtg ctc aag       1704
Thr Ala Leu Asn Cys Gly Val Glu Leu Phe Lys Arg Gly Val Leu Lys
            515                 520                 525 gaa tat ggt gtg aaa gtc ctg gga act tca gtt gag tcc att atg gct       1752
Glu Tyr Gly Val Lys Val Leu Gly Thr Ser Val Glu Ser Ile Met Ala
        530                 535                 540 acg gaa gac agg cag ctg ttt tca gat aaa cta aat gag atc aat gaa       1800
Thr Glu Asp Arg Gln Leu Phe Ser Asp Lys Leu Asn Glu Ile Asn Glu
545                 550                 555 aag att gct cca agt ttt gca gtg gaa tcg att gag gat gca ctg aag       1848
Lys Ile Ala Pro Ser Phe Ala Val Glu Ser Ile Glu Asp Ala Leu Lys
560                 565                 570                 575 gca gca gac acc att ggc tac cca gtg atg atc cgt tcc gcc tat gca       1896
Ala Ala Asp Thr Ile Gly Tyr Pro Val Met Ile Arg Ser Ala Tyr Ala
```

```
                        580                 585                 590
ctg ggt ggg tta ggc tca ggc atc tgt ccc aac aga gag act ttg atg    1944
Leu Gly Gly Leu Gly Ser Gly Ile Cys Pro Asn Arg Glu Thr Leu Met
            595                 600                 605 gac ctc agc aca aag gcc ttt gct atg acc aac caa att ctg gtg gag    1992
Asp Leu Ser Thr Lys Ala Phe Ala Met Thr Asn Gln Ile Leu Val Glu
            610                 615                 620 aag tca gtg aca ggt tgg aaa gaa ata gaa tat gaa gtg gtt cga gat    2040
Lys Ser Val Thr Gly Trp Lys Glu Ile Glu Tyr Glu Val Val Arg Asp
            625                 630                 635 gct gat gac aat tgt gtc act gtc tgt aac atg gaa aat gtt gat gcc    2088
Ala Asp Asp Asn Cys Val Thr Val Cys Asn Met Glu Asn Val Asp Ala
640                 645                 650                 655 atg ggt gtt cac aca ggt gac tca gtt gtt gtg gct cct gcc cag aca    2136
Met Gly Val His Thr Gly Asp Ser Val Val Val Ala Pro Ala Gln Thr
            660                 665                 670 ctc tcc aat gcc gag ttt cag atg ttg aga cgt act tca atc aat gtt    2184
Leu Ser Asn Ala Glu Phe Gln Met Leu Arg Arg Thr Ser Ile Asn Val
            675                 680                 685 gtt cgc cac ttg ggc att gtg ggt gaa tgc aac att cag ttt gcc ctt    2232
Val Arg His Leu Gly Ile Val Gly Glu Cys Asn Ile Gln Phe Ala Leu
            690                 695                 700 cat cct acc tca atg gaa tac tgc atc att gaa gtg aat gcc aga ctg    2280
His Pro Thr Ser Met Glu Tyr Cys Ile Ile Glu Val Asn Ala Arg Leu
705                 710                 715 tcc cga agc tct gct ctg gcc tca aaa gcc act ggc tac cca ttg gca    2328
Ser Arg Ser Ser Ala Leu Ala Ser Lys Ala Thr Gly Tyr Pro Leu Ala
720                 725                 730                 735 ttc att gct gca aag att gcc cta gga atc cca ctt cca gaa att aag    2376
Phe Ile Ala Ala Lys Ile Ala Leu Gly Ile Pro Leu Pro Glu Ile Lys
            740                 745                 750 aac gtc gta tcc ggg aag aca tca gcc tgt ttt gaa cct agc ctg gat    2424
Asn Val Val Ser Gly Lys Thr Ser Ala Cys Phe Glu Pro Ser Leu Asp
            755                 760                 765 tac atg gtc acc aag att ccc cgc tgg gat ctt gac cgt ttt cat gga    2472
Tyr Met Val Thr Lys Ile Pro Arg Trp Asp Leu Asp Arg Phe His Gly
            770                 775                 780 aca tct agc cga att ggt agc tct atg aaa agt gta gga gag gtc atg    2520
Thr Ser Ser Arg Ile Gly Ser Ser Met Lys Ser Val Gly Glu Val Met
785                 790                 795 gct att ggt cgt acc ttt gag gag agt ttc cag aaa gct tta cgg atg    2568
Ala Ile Gly Arg Thr Phe Glu Glu Ser Phe Gln Lys Ala Leu Arg Met
800                 805                 810                 815 tgc cac cca tct ata gaa ggt ttc act ccc cgt ctc cca atg aac aaa    2616
Cys His Pro Ser Ile Glu Gly Phe Thr Pro Arg Leu Pro Met Asn Lys
            820                 825                 830 gaa tgg cca tct aat tta gat ctt aga aaa gag ttg tct gaa cca agc    2664
Glu Trp Pro Ser Asn Leu Asp Leu Arg Lys Glu Leu Ser Glu Pro Ser
            835                 840                 845 agc acg cgt atc tat gcc att gcc aag gcc att gat gac aac atg tcc    2712
Ser Thr Arg Ile Tyr Ala Ile Ala Lys Ala Ile Asp Asp Asn Met Ser
            850                 855                 860 ctt gat gag att gag aag ctc aca tac att gac aag tgg ttt ttg tat    2760
Leu Asp Glu Ile Glu Lys Leu Thr Tyr Ile Asp Lys Trp Phe Leu Tyr
865                 870                 875 aag atg cgt gat att tta aac atg gaa aag aca ctg aaa ggg ctc aac    2808
Lys Met Arg Asp Ile Leu Asn Met Glu Lys Thr Leu Lys Gly Leu Asn
880                 885                 890                 895 agt gag tcc atg aca gaa gaa acc ctg aaa agg gca aag gag att ggg    2856
```

```
                                                              -continued

Ser Glu Ser Met Thr Glu Thr Leu Lys Arg Ala Lys Glu Ile Gly
            900             905             910 ttc tca gat aag cag att tca aaa tgc ctt ggg ctc act gag gcc cag        2904
Phe Ser Asp Lys Gln Ile Ser Lys Cys Leu Gly Leu Thr Glu Ala Gln
            915             920             925 aca agg gag ctg agg tta aag aaa aac atc cac cct tgg gtt aaa cag        2952
Thr Arg Glu Leu Arg Leu Lys Lys Asn Ile His Pro Trp Val Lys Gln
            930             935             940 att gat aca ctg gct gca gaa tac cca tca gta aca aac tat ctc tat        3000
Ile Asp Thr Leu Ala Ala Glu Tyr Pro Ser Val Thr Asn Tyr Leu Tyr
    945             950             955 gtt acc tac aat ggt cag gag cat gat gtc aat ttt gat gac cat gga        3048
Val Thr Tyr Asn Gly Gln Glu His Asp Val Asn Phe Asp Asp His Gly
960             965             970             975 atg atg gtg cta ggc tgt ggt cca tat cac att ggc agc agt gtg gaa        3096
Met Met Val Leu Gly Cys Gly Pro Tyr His Ile Gly Ser Ser Val Glu
            980             985             990 ttt gat tgg tgt gct gtc tct agt atc cgc aca ctg cgt caa ctt ggc        3144
Phe Asp Trp Cys Ala Val Ser Ser Ile Arg Thr Leu Arg Gln Leu Gly
            995             1000            1005 aag aag acg gtg gtg gtg aat tgc aat cct gag act gtg agc aca            3189
Lys Lys Thr Val Val Val Asn Cys Asn Pro Glu Thr Val Ser Thr
            1010            1015            1020 gac ttt gat gag tgt gac aaa ctg tac ttt gaa gag ttg tcc ttg            3234
Asp Phe Asp Glu Cys Asp Lys Leu Tyr Phe Glu Glu Leu Ser Leu
            1025            1030            1035 gag aga atc cta gac atc tac cat cag gag gca tgt ggt ggc tgc            3279
Glu Arg Ile Leu Asp Ile Tyr His Gln Glu Ala Cys Gly Gly Cys
            1040            1045            1050 atc ata tca gtt gga ggc cag att cca aac aac ctg gca gtt cct            3324
Ile Ile Ser Val Gly Gly Gln Ile Pro Asn Asn Leu Ala Val Pro
            1055            1060            1065 cta tac aag aat ggt gtc aag atc atg ggc aca agc ccc ctg cag            3369
Leu Tyr Lys Asn Gly Val Lys Ile Met Gly Thr Ser Pro Leu Gln
            1070            1075            1080 atc gac agg gct gag gat cgc tcc atc ttc tca gct gtc ttg gat            3414
Ile Asp Arg Ala Glu Asp Arg Ser Ile Phe Ser Ala Val Leu Asp
            1085            1090            1095 gag ctg aag gtg gct cag gca cct tgg aaa gct gtt aat act ttg            3459
Glu Leu Lys Val Ala Gln Ala Pro Trp Lys Ala Val Asn Thr Leu
            1100            1105            1110 aat gaa gca ctg gaa ttt gca aag tct gtg gac tac ccc tgc ttg            3504
Asn Glu Ala Leu Glu Phe Ala Lys Ser Val Asp Tyr Pro Cys Leu
            1115            1120            1125 ttg agg cct tcc tat gtt ttg agt ggg tct gct atg aat gtg gta            3549
Leu Arg Pro Ser Tyr Val Leu Ser Gly Ser Ala Met Asn Val Val
            1130            1135            1140 ttc tct gag gat gag atg aaa aaa ttc cta gaa gag gcg act aga            3594
Phe Ser Glu Asp Glu Met Lys Lys Phe Leu Glu Glu Ala Thr Arg
            1145            1150            1155 gtt tct cag gag cac cca gtg gtc ctg aca aaa ttt gtt gaa ggg            3639
Val Ser Gln Glu His Pro Val Val Leu Thr Lys Phe Val Glu Gly
            1160            1165            1170 gcc cga gaa gta gaa atg gac gct gtt ggc aaa gat gga agg gtt            3684
Ala Arg Glu Val Glu Met Asp Ala Val Gly Lys Asp Gly Arg Val
            1175            1180            1185 atc tct cat gcc atc tct gaa cat gtt gaa gat gca ggt gtc cac            3729
Ile Ser His Ala Ile Ser Glu His Val Glu Asp Ala Gly Val His
            1190            1195            1200
```

```
tcg gga gat gcc act ctg atg ctg ccc aca caa acc atc agc caa      3774
Ser Gly Asp Ala Thr Leu Met Leu Pro Thr Gln Thr Ile Ser Gln
        1205                1210                1215 ggg gcc att gaa aag gtg aag gat gct acc cgg aag att gca aag      3819
Gly Ala Ile Glu Lys Val Lys Asp Ala Thr Arg Lys Ile Ala Lys
        1220                1225                1230 gct ttt gcc atc tct ggt cca ttc aac gtc caa ttt ctt gtc aaa      3864
Ala Phe Ala Ile Ser Gly Pro Phe Asn Val Gln Phe Leu Val Lys
        1235                1240                1245 gga aat gat gtc ttg gtg att gag tgt aac ttg aga gct tct cga      3909
Gly Asn Asp Val Leu Val Ile Glu Cys Asn Leu Arg Ala Ser Arg
        1250                1255                1260 tcc ttc ccc ttt gtt tcc aag act ctt ggg gtt gac ttc att gat      3954
Ser Phe Pro Phe Val Ser Lys Thr Leu Gly Val Asp Phe Ile Asp
        1265                1270                1275 gtg gcc acc aag gtg atg att gga gag aat gtt gat gag aaa cat      3999
Val Ala Thr Lys Val Met Ile Gly Glu Asn Val Asp Glu Lys His
        1280                1285                1290 ctt cca aca ttg gac cat ccc ata att cct gct gac tat gtt gca      4044
Leu Pro Thr Leu Asp His Pro Ile Ile Pro Ala Asp Tyr Val Ala
        1295                1300                1305 att aag gct ccc atg ttt tcc tgg ccc cgg ttg agg gat gct gac      4089
Ile Lys Ala Pro Met Phe Ser Trp Pro Arg Leu Arg Asp Ala Asp
        1310                1315                1320 ccc att ctg aga tgt gag atg gct tcc act gga gag gtg gct tgc      4134
Pro Ile Leu Arg Cys Glu Met Ala Ser Thr Gly Glu Val Ala Cys
        1325                1330                1335 ttt ggt gaa ggt att cat aca gcc ttc cta aag gca atg ctt tcc      4179
Phe Gly Glu Gly Ile His Thr Ala Phe Leu Lys Ala Met Leu Ser
        1340                1345                1350 aca gga ttt aag ata ccc cag aaa ggc atc ctg ata ggc atc cag      4224
Thr Gly Phe Lys Ile Pro Gln Lys Gly Ile Leu Ile Gly Ile Gln
        1355                1360                1365 caa tca ttc cgg cca aga ttc ctt ggt gtg gct gaa caa tta cac      4269
Gln Ser Phe Arg Pro Arg Phe Leu Gly Val Ala Glu Gln Leu His
        1370                1375                1380 aat gaa ggt ttc aag ctg ttt gcc acg gaa gcc aca tca gac tgg      4314
Asn Glu Gly Phe Lys Leu Phe Ala Thr Glu Ala Thr Ser Asp Trp
        1385                1390                1395 ctc aac gcc aac aat gtc cct gcc aac cca gtg gca tgg ccg tct      4359
Leu Asn Ala Asn Asn Val Pro Ala Asn Pro Val Ala Trp Pro Ser
        1400                1405                1410 caa gaa gga cag aat ccc agc ctc tct tcc atc aga aaa ttg att      4404
Gln Glu Gly Gln Asn Pro Ser Leu Ser Ser Ile Arg Lys Leu Ile
        1415                1420                1425 aga gat ggc agc att gac cta gtg att aac ctt ccc aac aac aac      4449
Arg Asp Gly Ser Ile Asp Leu Val Ile Asn Leu Pro Asn Asn Asn
        1430                1435                1440 act aaa ttt gtc cat gat aat tat gtg att cgg agg aca gct gtt      4494
Thr Lys Phe Val His Asp Asn Tyr Val Ile Arg Arg Thr Ala Val
        1445                1450                1455 gat agt gga atc cct ctc ctc act aat ttt cag gtg acc aaa ctt      4539
Asp Ser Gly Ile Pro Leu Leu Thr Asn Phe Gln Val Thr Lys Leu
        1460                1465                1470 ttt gct gaa gct gtg cag aaa tct cgc aag gtg gac tcc aag agt      4584
Phe Ala Glu Ala Val Gln Lys Ser Arg Lys Val Asp Ser Lys Ser
        1475                1480                1485 ctt ttc cac tac agg cag tac agt gct gga aaa gca gca tag          4626
Leu Phe His Tyr Arg Gln Tyr Ser Ala Gly Lys Ala Ala
        1490                1495                1500
```

-continued

```
agatgcagac accccagccc cattattaaa tcaacctgag ccacatgtta tctaaaggaa    4686
ctgattcaca actttctcag agatgaatat tgataactaa acttcatttc agtttacttt    4746
gttatgcctt aatattctgt gtcttttgca attaaattgt cagtcacttc ttcaaaacct    4806
tacagtcctt cctaagttac tcttcatgag atttcatcca tttactaata ctgtattttt    4866
ggtggactag gcttgcctat gtgcttatgt gtagcttttt acttttttatg gtgctgatta    4926 atggtgatca aggtaggaaa agttgctgtt ctattttctg aactctttct atactttaag    4986
atactctatt tttaaaacac tatctgcaaa ctcaggacac tttaacaggg cagaatactc    5046
taaaaacttg ataaaatgaa atatagattt aatttatgaa ccttccatca tgatgtttgt    5106
gtattgcttc tttttggatc ctcattctca cccatttggc taatccagga atattgttat    5166
cccttcccat tatattgaag ttgagaaatg tgacagaggc atttagagta tggacttttc    5226
ttttcttttt cttttcttt ttttcttttt gagatggagt cacactctcc aggctggagt    5286
gcagtggcac aatctcggct cactgcaatt tgcgtctccc aagttcaagc gattctcctg    5346
ctttagacta tggatttctt taaggaatac tggtttgcag ttttgttttc tggactatat    5406
cagcagatgg tagacagtgt ttatgtagat gtgttgttgt ttttatcatt ggattttaac    5466
ttggcccgag tgaaataatc agattttgt cattcacact ctcccccagt tttggaataa    5526
cttggaagta aggttcattc ccttaagacg atggattctg ttgaactatg gggtcccaca    5586
ctgcactatt aattccaccc actgtaaggg caaggacacc attccttcta catataagaa    5646
aaaagtctct ccccaagggc agcctttgtt acttttaaat attttctgtt attacaagtg    5706
ctctaattgt gaactttaa ataaaatact attaagaggt aaaaaaaaaa aaaaa         5761
```

<210> SEQ ID NO 12
<211> LENGTH: 1500
<212> TYPE: PRT
<213> ORGANISM: Homo sapiens

<400> SEQUENCE: 12

```
Met Thr Arg Leu Leu Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
    50                  55                  60

Ser Ser Val Ala Gly Glu Val Val Phe Asn Thr Gly Leu Gly Gly Tyr
65                  70                  75                  80

Pro Glu Ala Ile Thr Asp Pro Ala Tyr Lys Gly Gln Ile Leu Thr Met
                85                  90                  95

Ala Asn Pro Ile Ile Gly Asn Gly Gly Ala Pro Asp Thr Thr Ala Leu
            100                 105                 110

Asp Glu Leu Gly Leu Ser Lys Tyr Leu Glu Ser Asn Gly Ile Lys Val
        115                 120                 125

Ser Gly Leu Leu Val Leu Asp Tyr Ser Lys Asp Tyr Asn His Trp Leu
    130                 135                 140

Ala Thr Lys Ser Leu Gly Gln Trp Leu Gln Glu Glu Lys Val Pro Ala
145                 150                 155                 160

Ile Tyr Gly Val Asp Thr Arg Met Leu Thr Lys Ile Ile Arg Asp Lys
                165                 170                 175
```

-continued

```
Gly Thr Met Leu Gly Lys Ile Glu Phe Glu Gly Gln Pro Val Asp Phe
            180                 185                 190
Val Asp Pro Asn Lys Gln Asn Leu Ile Ala Glu Val Ser Thr Lys Asp
        195                 200                 205
Val Lys Val Tyr Gly Lys Gly Asn Pro Thr Lys Val Ala Val Asp
    210                 215                 220
Cys Gly Ile Lys Asn Asn Val Ile Arg Leu Leu Val Lys Arg Gly Ala
225                 230                 235                 240
Glu Val His Leu Val Pro Trp Asn His Asp Phe Thr Lys Met Glu Tyr
                245                 250                 255
Asp Gly Ile Leu Ile Ala Gly Gly Pro Gly Asn Pro Ala Leu Ala Glu
            260                 265                 270
Pro Leu Ile Gln Asn Val Arg Lys Ile Leu Glu Ser Asp Arg Lys Glu
        275                 280                 285
Pro Leu Phe Gly Ile Ser Thr Gly Asn Leu Ile Thr Gly Leu Ala Ala
    290                 295                 300
Gly Ala Lys Thr Tyr Lys Met Ser Met Ala Asn Arg Gly Gln Asn Gln
305                 310                 315                 320
Pro Val Leu Asn Ile Thr Asn Lys Gln Ala Phe Ile Thr Ala Gln Asn
                325                 330                 335
His Gly Tyr Ala Leu Asp Asn Thr Leu Pro Ala Gly Trp Lys Pro Leu
            340                 345                 350
Phe Val Asn Val Asn Asp Gln Thr Asn Glu Gly Ile Met His Glu Ser
        355                 360                 365
Lys Pro Phe Phe Ala Val Gln Phe His Pro Glu Val Thr Pro Gly Pro
    370                 375                 380
Ile Asp Thr Glu Tyr Leu Phe Asp Ser Phe Phe Ser Leu Ile Lys Lys
385                 390                 395                 400
Gly Lys Ala Thr Thr Ile Thr Ser Val Leu Pro Lys Pro Ala Leu Val
                405                 410                 415
Ala Ser Arg Val Glu Val Ser Lys Val Leu Ile Leu Gly Ser Gly Gly
            420                 425                 430
Leu Ser Ile Gly Gln Ala Gly Glu Phe Asp Tyr Ser Gly Ser Gln Ala
        435                 440                 445
Val Lys Ala Met Lys Glu Glu Asn Val Lys Thr Val Leu Met Asn Pro
    450                 455                 460
Asn Ile Ala Ser Val Gln Thr Asn Glu Val Gly Leu Lys Gln Ala Asp
465                 470                 475                 480
Thr Val Tyr Phe Leu Pro Ile Thr Pro Gln Phe Val Thr Glu Val Ile
                485                 490                 495
Lys Ala Glu Gln Pro Asp Gly Leu Ile Leu Gly Met Gly Gly Gln Thr
            500                 505                 510
Ala Leu Asn Cys Gly Val Glu Leu Phe Lys Arg Gly Val Leu Lys Glu
        515                 520                 525
Tyr Gly Val Lys Val Leu Gly Thr Ser Val Glu Ser Ile Met Ala Thr
    530                 535                 540
Glu Asp Arg Gln Leu Phe Ser Asp Lys Leu Asn Glu Ile Asn Glu Lys
545                 550                 555                 560
Ile Ala Pro Ser Phe Ala Val Glu Ser Ile Glu Asp Ala Leu Lys Ala
                565                 570                 575
Ala Asp Thr Ile Gly Tyr Pro Val Met Ile Arg Ser Ala Tyr Ala Leu
            580                 585                 590
```

-continued

```
Gly Gly Leu Gly Ser Gly Ile Cys Pro Asn Arg Glu Thr Leu Met Asp
            595                 600                 605

Leu Ser Thr Lys Ala Phe Ala Met Thr Asn Gln Ile Leu Val Glu Lys
        610                 615                 620

Ser Val Thr Gly Trp Lys Glu Ile Glu Tyr Glu Val Val Arg Asp Ala
625                 630                 635                 640

Asp Asp Asn Cys Val Thr Val Cys Asn Met Glu Asn Val Asp Ala Met
                645                 650                 655

Gly Val His Thr Gly Asp Ser Val Val Ala Pro Ala Gln Thr Leu
            660                 665                 670

Ser Asn Ala Glu Phe Gln Met Leu Arg Arg Thr Ser Ile Asn Val Val
        675                 680                 685

Arg His Leu Gly Ile Val Gly Glu Cys Asn Ile Gln Phe Ala Leu His
    690                 695                 700

Pro Thr Ser Met Glu Tyr Cys Ile Ile Glu Val Asn Ala Arg Leu Ser
705                 710                 715                 720

Arg Ser Ser Ala Leu Ala Ser Lys Ala Thr Gly Tyr Pro Leu Ala Phe
                725                 730                 735

Ile Ala Ala Lys Ile Ala Leu Gly Ile Pro Leu Pro Glu Ile Lys Asn
            740                 745                 750

Val Val Ser Gly Lys Thr Ser Ala Cys Phe Glu Pro Ser Leu Asp Tyr
        755                 760                 765

Met Val Thr Lys Ile Pro Arg Trp Asp Leu Asp Arg Phe His Gly Thr
770                 775                 780

Ser Ser Arg Ile Gly Ser Ser Met Lys Ser Val Gly Glu Val Met Ala
785                 790                 795                 800

Ile Gly Arg Thr Phe Glu Glu Ser Phe Gln Lys Ala Leu Arg Met Cys
                805                 810                 815

His Pro Ser Ile Glu Gly Phe Thr Pro Arg Leu Pro Met Asn Lys Glu
            820                 825                 830

Trp Pro Ser Asn Leu Asp Leu Arg Lys Glu Leu Ser Glu Pro Ser Ser
        835                 840                 845

Thr Arg Ile Tyr Ala Ile Ala Lys Ala Ile Asp Asp Asn Met Ser Leu
850                 855                 860

Asp Glu Ile Glu Lys Leu Thr Tyr Ile Asp Lys Trp Phe Leu Tyr Lys
865                 870                 875                 880

Met Arg Asp Ile Leu Asn Met Glu Lys Thr Leu Lys Gly Leu Asn Ser
                885                 890                 895

Glu Ser Met Thr Glu Glu Thr Leu Lys Arg Ala Lys Glu Ile Gly Phe
            900                 905                 910

Ser Asp Lys Gln Ile Ser Lys Cys Leu Gly Leu Thr Glu Ala Gln Thr
        915                 920                 925

Arg Glu Leu Arg Leu Lys Lys Asn Ile His Pro Trp Val Lys Gln Ile
930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
        995                 1000                1005

Lys Thr Val Val Val Asn Cys Asn Pro Glu Thr Val Ser Thr Asp
```

-continued

```
            1010                1015                1020

Phe Asp Glu Cys Asp Lys Leu Tyr Phe Glu Leu Ser Leu Glu
    1025                1030                1035

Arg Ile Leu Asp Ile Tyr His Gln Glu Ala Cys Gly Gly Cys Ile
    1040                1045                1050

Ile Ser Val Gly Gly Gln Ile Pro Asn Asn Leu Ala Val Pro Leu
    1055                1060                1065

Tyr Lys Asn Gly Val Lys Ile Met Gly Thr Ser Pro Leu Gln Ile
    1070                1075                1080

Asp Arg Ala Glu Asp Arg Ser Ile Phe Ser Ala Val Leu Asp Glu
    1085                1090                1095

Leu Lys Val Ala Gln Ala Pro Trp Lys Ala Val Asn Thr Leu Asn
    1100                1105                1110

Glu Ala Leu Glu Phe Ala Lys Ser Val Asp Tyr Pro Cys Leu Leu
    1115                1120                1125

Arg Pro Ser Tyr Val Leu Ser Gly Ser Ala Met Asn Val Val Phe
    1130                1135                1140

Ser Glu Asp Glu Met Lys Lys Phe Leu Glu Glu Ala Thr Arg Val
    1145                1150                1155

Ser Gln Glu His Pro Val Val Leu Thr Lys Phe Val Glu Gly Ala
    1160                1165                1170

Arg Glu Val Glu Met Asp Ala Val Gly Lys Asp Gly Arg Val Ile
    1175                1180                1185

Ser His Ala Ile Ser Glu His Val Glu Asp Ala Gly Val His Ser
    1190                1195                1200

Gly Asp Ala Thr Leu Met Leu Pro Thr Gln Thr Ile Ser Gln Gly
    1205                1210                1215

Ala Ile Glu Lys Val Lys Asp Ala Thr Arg Lys Ile Ala Lys Ala
    1220                1225                1230

Phe Ala Ile Ser Gly Pro Phe Asn Val Gln Phe Leu Val Lys Gly
    1235                1240                1245

Asn Asp Val Leu Val Ile Glu Cys Asn Leu Arg Ala Ser Arg Ser
    1250                1255                1260

Phe Pro Phe Val Ser Lys Thr Leu Gly Val Asp Phe Ile Asp Val
    1265                1270                1275

Ala Thr Lys Val Met Ile Gly Glu Asn Val Asp Glu Lys His Leu
    1280                1285                1290

Pro Thr Leu Asp His Pro Ile Ile Pro Ala Asp Tyr Val Ala Ile
    1295                1300                1305

Lys Ala Pro Met Phe Ser Trp Pro Arg Leu Arg Asp Ala Asp Pro
    1310                1315                1320

Ile Leu Arg Cys Glu Met Ala Ser Thr Gly Glu Val Ala Cys Phe
    1325                1330                1335

Gly Glu Gly Ile His Thr Ala Phe Leu Lys Ala Met Leu Ser Thr
    1340                1345                1350

Gly Phe Lys Ile Pro Gln Lys Gly Ile Leu Ile Gly Ile Gln Gln
    1355                1360                1365

Ser Phe Arg Pro Arg Phe Leu Gly Val Ala Glu Gln Leu His Asn
    1370                1375                1380

Glu Gly Phe Lys Leu Phe Ala Thr Glu Ala Thr Ser Asp Trp Leu
    1385                1390                1395

Asn Ala Asn Asn Val Pro Ala Asn Pro Val Ala Trp Pro Ser Gln
    1400                1405                1410
```

```
Glu Gly Gln Asn Pro Ser Leu Ser Ser Ile Arg Lys Leu Ile Arg
    1415                1420                1425

Asp Gly Ser Ile Asp Leu Val Ile Asn Leu Pro Asn Asn Asn Thr
    1430                1435                1440

Lys Phe Val His Asp Asn Tyr Val Ile Arg Arg Thr Ala Val Asp
    1445                1450                1455

Ser Gly Ile Pro Leu Leu Thr Asn Phe Gln Val Thr Lys Leu Phe
    1460                1465                1470

Ala Glu Ala Val Gln Lys Ser Arg Lys Val Asp Ser Lys Ser Leu
    1475                1480                1485

Phe His Tyr Arg Gln Tyr Ser Ala Gly Lys Ala Ala
    1490                1495                1500

<210> SEQ ID NO 13
<211> LENGTH: 5761
<212> TYPE: DNA
<213> ORGANISM: Homo sapiens
<220> FEATURE:
<221> NAME/KEY: CDS
<222> LOCATION: (124)..(4626)

<400> SEQUENCE: 13
gtcagcctta aacactgact gcacccctcc cagatttctt ttacattaac taaaaagtct    60
tatcacacaa tctcataaaa tttatgtaat ttcatttaat tttagccaca aatcatcttc   120 aaa atg acg agg att att aca gct ttc aaa gtg gtg agg aca ctg aag    168
    Met Thr Arg Ile Ile Thr Ala Phe Lys Val Val Arg Thr Leu Lys
    1               5                   10                  15 act ggt ttt ggc ttt acc aat gtg act gca cac caa aaa tgg aaa ttt    216
Thr Gly Phe Gly Phe Thr Asn Val Thr Ala His Gln Lys Trp Lys Phe
                20                  25                  30 tca aga cct ggc atc agg ctc ctt tct gtc aag gca cag aca gca cac    264
Ser Arg Pro Gly Ile Arg Leu Leu Ser Val Lys Ala Gln Thr Ala His
            35                  40                  45 att gtc ctg gaa gat gga act aag atg aaa ggt tac tcc ttt ggc cat    312
Ile Val Leu Glu Asp Gly Thr Lys Met Lys Gly Tyr Ser Phe Gly His
        50                  55                  60 cca tcc tct gtt gct ggt gaa gtg gtt ttt aat act ggc ctg gga ggg    360
Pro Ser Ser Val Ala Gly Glu Val Val Phe Asn Thr Gly Leu Gly Gly
    65                  70                  75 tac cca gaa gct att act gac cct gcc tac aaa gga cag att ctc aca    408
Tyr Pro Glu Ala Ile Thr Asp Pro Ala Tyr Lys Gly Gln Ile Leu Thr
80                  85                  90                  95 atg gcc aac cct att att ggg aat ggt gga gct cct gat act act gct    456
Met Ala Asn Pro Ile Ile Gly Asn Gly Gly Ala Pro Asp Thr Thr Ala
                100                 105                 110 ctg gat gaa ctg gga ctt agc aaa tat ttg gag tct aat gga atc aag    504
Leu Asp Glu Leu Gly Leu Ser Lys Tyr Leu Glu Ser Asn Gly Ile Lys
            115                 120                 125 gtt tca ggt ttg ctg gtg ctg gat tat agt aaa gac tac aac cac tgg    552
Val Ser Gly Leu Leu Val Leu Asp Tyr Ser Lys Asp Tyr Asn His Trp
        130                 135                 140 ctg gct acc aag agt tta ggg caa tgg cta cag gaa gaa aag gtt cct    600
Leu Ala Thr Lys Ser Leu Gly Gln Trp Leu Gln Glu Glu Lys Val Pro
    145                 150                 155 gca att tat gga gtg gac aca aga atg ctg act aaa ata att cgg gat    648
Ala Ile Tyr Gly Val Asp Thr Arg Met Leu Thr Lys Ile Ile Arg Asp
160                 165                 170                 175 aag ggt acc atg ctt ggg aag att gaa ttt gaa ggt cag cct gtg gat    696
```

-continued

| | | | | | | | | | | | | |
|---|---|---|---|---|---|---|---|---|---|---|---|---|
| Lys | Gly | Thr | Met | Leu | Gly | Lys | Ile | Glu | Phe | Glu | Gly | Gln | Pro | Val | Asp |
| | | | 180 | | | | | 185 | | | | | 190 | | |

```
ttt gtg gat cca aat aaa cag aat ttg att gct gag gtt tca acc aag        744
Phe Val Asp Pro Asn Lys Gln Asn Leu Ile Ala Glu Val Ser Thr Lys
            195                 200                 205 gat gtc aaa gtg tac ggc aaa gga aac ccc aca aaa gtg gta gct gta        792
Asp Val Lys Val Tyr Gly Lys Gly Asn Pro Thr Lys Val Val Ala Val
        210                 215                 220 gac tgt ggg att aaa aac aat gta atc cgc ctg cta gta aag cga gga        840
Asp Cys Gly Ile Lys Asn Asn Val Ile Arg Leu Leu Val Lys Arg Gly
    225                 230                 235 gct gaa gtg cac tta gtt ccc tgg aac cat gat ttc acc aag atg gag        888
Ala Glu Val His Leu Val Pro Trp Asn His Asp Phe Thr Lys Met Glu
240                 245                 250                 255 tat gat ggg att ttg atc gcg gga gga ccg ggg aac cca gct ctt gca        936
Tyr Asp Gly Ile Leu Ile Ala Gly Gly Pro Gly Asn Pro Ala Leu Ala
                260                 265                 270 gaa cca cta att cag aat gtc aga aag att ttg gag agt gat cgc aag        984
Glu Pro Leu Ile Gln Asn Val Arg Lys Ile Leu Glu Ser Asp Arg Lys
            275                 280                 285 gag cca ttg ttt gga atc agt aca gga aac tta ata aca gga ttg gct       1032
Glu Pro Leu Phe Gly Ile Ser Thr Gly Asn Leu Ile Thr Gly Leu Ala
        290                 295                 300 gct ggt gcc aaa acc tac aag atg tcc atg gcc aac aga ggg cag aat       1080
Ala Gly Ala Lys Thr Tyr Lys Met Ser Met Ala Asn Arg Gly Gln Asn
    305                 310                 315 cag cct gtt ttg aat atc aca aac aaa cag gct ttc att act gct cag       1128
Gln Pro Val Leu Asn Ile Thr Asn Lys Gln Ala Phe Ile Thr Ala Gln
320                 325                 330                 335 aat cat ggc tat gcc ttg gac aac acc ctc cct gct ggc tgg aaa cca       1176
Asn His Gly Tyr Ala Leu Asp Asn Thr Leu Pro Ala Gly Trp Lys Pro
                340                 345                 350 ctt ttt gtg aat gtc aac gat caa aca aat gag ggg att atg cat gag       1224
Leu Phe Val Asn Val Asn Asp Gln Thr Asn Glu Gly Ile Met His Glu
            355                 360                 365 agc aaa ccc ttc ttc gct gtg cag ttc cac cca gag gtc acc ccg ggg       1272
Ser Lys Pro Phe Phe Ala Val Gln Phe His Pro Glu Val Thr Pro Gly
        370                 375                 380 cca ata gac act gag tac ctg ttt gat tcc ttt tca ctg ata aag           1320
Pro Ile Asp Thr Glu Tyr Leu Phe Asp Ser Phe Phe Ser Leu Ile Lys
385                 390                 395 aaa gga aaa gct acc acc att aca tca gtc tta ccg aag cca gca cta       1368
Lys Gly Lys Ala Thr Thr Ile Thr Ser Val Leu Pro Lys Pro Ala Leu
400                 405                 410                 415 gtt gca tct cgg gtt gag gtt tcc aaa gtc ctt att cta gga tca gga       1416
Val Ala Ser Arg Val Glu Val Ser Lys Val Leu Ile Leu Gly Ser Gly
                420                 425                 430 ggt ctg tcc att ggt cag gct gga gaa ttt gat tac tca gga tct caa       1464
Gly Leu Ser Ile Gly Gln Ala Gly Glu Phe Asp Tyr Ser Gly Ser Gln
            435                 440                 445 gct gta aaa gcc atg aag gaa gaa aat gtc aaa act gtt ctg atg aac       1512
Ala Val Lys Ala Met Lys Glu Glu Asn Val Lys Thr Val Leu Met Asn
        450                 455                 460 cca aac att gca tca gtc cag acc aat gag gtg ggc tta aag caa gcg       1560
Pro Asn Ile Ala Ser Val Gln Thr Asn Glu Val Gly Leu Lys Gln Ala
    465                 470                 475 gat act gtc tac ttt ctt ccc atc acc cct cag ttt gtc aca gag gtc       1608
Asp Thr Val Tyr Phe Leu Pro Ile Thr Pro Gln Phe Val Thr Glu Val
480                 485                 490                 495
```

```
atc aag gca gaa cag cca gat ggg tta att ctg ggc atg ggt ggc cag      1656
Ile Lys Ala Glu Gln Pro Asp Gly Leu Ile Leu Gly Met Gly Gly Gln
            500                 505                 510 aca gct ctg aac tgt gga gtg gaa cta ttc aag aga ggt gtg ctc aag      1704
Thr Ala Leu Asn Cys Gly Val Glu Leu Phe Lys Arg Gly Val Leu Lys
            515                 520                 525 gaa tat ggt gtg aaa gtc ctg gga act tca gtt gag tcc att atg gct      1752
Glu Tyr Gly Val Lys Val Leu Gly Thr Ser Val Glu Ser Ile Met Ala
        530                 535                 540 acg gaa gac agg cag ctg ttt tca gat aaa cta aat gag atc aat gaa      1800
Thr Glu Asp Arg Gln Leu Phe Ser Asp Lys Leu Asn Glu Ile Asn Glu
545                 550                 555 aag att gct cca agt ttt gca gtg gaa tcg att gag gat gca ctg aag      1848
Lys Ile Ala Pro Ser Phe Ala Val Glu Ser Ile Glu Asp Ala Leu Lys
560                 565                 570                 575 gca gca gac acc att ggc tac cca gtg atg atc cgt tcc gcc tat gca      1896
Ala Ala Asp Thr Ile Gly Tyr Pro Val Met Ile Arg Ser Ala Tyr Ala
            580                 585                 590 ctg ggt ggg tta ggc tca ggc atc tgt ccc aac aga gag act ttg atg      1944
Leu Gly Gly Leu Gly Ser Gly Ile Cys Pro Asn Arg Glu Thr Leu Met
        595                 600                 605 gac ctc agc aca aag gcc ttt gct atg acc aac caa att ctg gtg gag      1992
Asp Leu Ser Thr Lys Ala Phe Ala Met Thr Asn Gln Ile Leu Val Glu
            610                 615                 620 aag tca gtg aca ggt tgg aaa gaa ata gaa tat gaa gtg gtt cga gat      2040
Lys Ser Val Thr Gly Trp Lys Glu Ile Glu Tyr Glu Val Val Arg Asp
625                 630                 635 gct gat gac aat tgt gtc act gtc tgt aac atg gaa aat gtt gat gcc      2088
Ala Asp Asp Asn Cys Val Thr Val Cys Asn Met Glu Asn Val Asp Ala
640                 645                 650                 655 atg ggt gtt cac aca ggt gac tca gtt gtt gtg gct cct gcc cag aca      2136
Met Gly Val His Thr Gly Asp Ser Val Val Val Ala Pro Ala Gln Thr
            660                 665                 670 ctc tcc aat gcc gag ttt cag atg ttg aga cgt act tca atc aat gtt      2184
Leu Ser Asn Ala Glu Phe Gln Met Leu Arg Arg Thr Ser Ile Asn Val
        675                 680                 685 gtt cgc cac ttg ggc att gtg ggt gaa tgc aac att cag ttt gcc ctt      2232
Val Arg His Leu Gly Ile Val Gly Glu Cys Asn Ile Gln Phe Ala Leu
            690                 695                 700 cat cct acc tca atg gaa tac tgc atc att gaa gtg aat gcc aga ctg      2280
His Pro Thr Ser Met Glu Tyr Cys Ile Ile Glu Val Asn Ala Arg Leu
705                 710                 715 tcc cga agc tct gct ctg gcc tca aaa gcc act ggc tac cca ttg gca      2328
Ser Arg Ser Ser Ala Leu Ala Ser Lys Ala Thr Gly Tyr Pro Leu Ala
720                 725                 730                 735 ttc att gct gca aag att gcc cta gga atc cca ctt cca gaa att aag      2376
Phe Ile Ala Ala Lys Ile Ala Leu Gly Ile Pro Leu Pro Glu Ile Lys
            740                 745                 750 aac gtc gta tcc ggg aag aca tca gcc tgt ttt gaa cct agc ctg gat      2424
Asn Val Val Ser Gly Lys Thr Ser Ala Cys Phe Glu Pro Ser Leu Asp
        755                 760                 765 tac atg gtc acc aag att ccc cgc tgg gat ctt gac cgt ttt cat gga      2472
Tyr Met Val Thr Lys Ile Pro Arg Trp Asp Leu Asp Arg Phe His Gly
            770                 775                 780 aca tct agc cga att ggt agc tct atg aaa agt gta gga gag gtc atg      2520
Thr Ser Ser Arg Ile Gly Ser Ser Met Lys Ser Val Gly Glu Val Met
785                 790                 795 gct att ggt cgt acc ttt gag gag agt ttc cag aaa gct tta cgg atg      2568
Ala Ile Gly Arg Thr Phe Glu Glu Ser Phe Gln Lys Ala Leu Arg Met
800                 805                 810                 815
```

-continued

```
tgc cac cca tct ata gaa ggt ttc act ccc cgt ctc cca atg aac aaa        2616
Cys His Pro Ser Ile Glu Gly Phe Thr Pro Arg Leu Pro Met Asn Lys
            820                 825                 830 gaa tgg cca tct aat tta gat ctt aga aaa gag ttg tct gaa cca agc        2664
Glu Trp Pro Ser Asn Leu Asp Leu Arg Lys Glu Leu Ser Glu Pro Ser
                835                 840                 845 agc acg cgt atc tat gcc att gcc aag gcc att gat gac aac atg tcc        2712
Ser Thr Arg Ile Tyr Ala Ile Ala Lys Ala Ile Asp Asp Asn Met Ser
        850                 855                 860 ctt gat gag att gag aag ctc aca tac att gac aag tgg ttt ttg tat        2760
Leu Asp Glu Ile Glu Lys Leu Thr Tyr Ile Asp Lys Trp Phe Leu Tyr
    865                 870                 875 aag atg cgt gat att tta aac atg gaa aag aca ctg aaa ggg ctc aac        2808
Lys Met Arg Asp Ile Leu Asn Met Glu Lys Thr Leu Lys Gly Leu Asn
880                 885                 890                 895 agt gag tcc atg aca gaa gaa acc ctg aaa agg gca aag gag att ggg        2856
Ser Glu Ser Met Thr Glu Glu Thr Leu Lys Arg Ala Lys Glu Ile Gly
                900                 905                 910 ttc tca gat aag cag att tca aaa tgc ctt ggg ctc act gag gcc cag        2904
Phe Ser Asp Lys Gln Ile Ser Lys Cys Leu Gly Leu Thr Glu Ala Gln
            915                 920                 925 aca agg gag ctg agg tta aag aaa aac atc cac cct tgg gtt aaa cag        2952
Thr Arg Glu Leu Arg Leu Lys Lys Asn Ile His Pro Trp Val Lys Gln
        930                 935                 940 att gat aca ctg gct gca gaa tac cca tca gta aca aac tat ctc tat        3000
Ile Asp Thr Leu Ala Ala Glu Tyr Pro Ser Val Thr Asn Tyr Leu Tyr
    945                 950                 955 gtt acc tac aat ggt cag gag cat gat gtc aat ttt gat gac cat gga        3048
Val Thr Tyr Asn Gly Gln Glu His Asp Val Asn Phe Asp Asp His Gly
960                 965                 970                 975 atg atg gtg cta ggc tgt ggt cca tat cac att ggc agc agt gtg gaa        3096
Met Met Val Leu Gly Cys Gly Pro Tyr His Ile Gly Ser Ser Val Glu
                980                 985                 990 ttt gat tgg tgt gct gtc tct agt atc cgc aca ctg cgt caa ctt ggc        3144
Phe Asp Trp Cys Ala Val Ser Ser Ile Arg Thr Leu Arg Gln Leu Gly
            995                1000                1005 aag aag acg gtg gtg gtg aat tgc aat cct gag act gtg     agc aca        3189
Lys Lys Thr Val Val Val Asn Cys Asn Pro Glu Thr Val     Ser Thr
        1010                1015                1020 gac ttt gat gag tgt gac aaa ctg tac ttt gaa gag ttg tcc ttg           3234
Asp Phe Asp Glu Cys Asp Lys Leu Tyr Phe Glu Glu Leu Ser Leu
    1025                1030                1035 gag aga atc cta gac atc tac cat cag gag gca tgt ggt ggc tgc           3279
Glu Arg Ile Leu Asp Ile Tyr His Gln Glu Ala Cys Gly Gly Cys
    1040                1045                1050 atc ata tca gtt gga ggc cag att cca aac aac ctg gca gtt cct           3324
Ile Ile Ser Val Gly Gly Gln Ile Pro Asn Asn Leu Ala Val Pro
    1055                1060                1065 cta tac aag aat ggt gtc aag atc atg ggc aca agc ccc ctg cag           3369
Leu Tyr Lys Asn Gly Val Lys Ile Met Gly Thr Ser Pro Leu Gln
    1070                1075                1080 atc gac agg gct gag gat cgc tcc atc ttc tca gct gtc ttg gat           3414
Ile Asp Arg Ala Glu Asp Arg Ser Ile Phe Ser Ala Val Leu Asp
    1085                1090                1095 gag ctg aag gtg gct cag gca cct tgg aaa gct gtt aat act ttg           3459
Glu Leu Lys Val Ala Gln Ala Pro Trp Lys Ala Val Asn Thr Leu
    1100                1105                1110 aat gaa gca ctg gaa ttt gca aag tct gtg gac tac ccc tgc ttg           3504
Asn Glu Ala Leu Glu Phe Ala Lys Ser Val Asp Tyr Pro Cys Leu
```

```
                    1115                 1120                 1125
ttg agg cct tcc tat gtt ttg agt ggg tct gct atg aat gtg gta    3549
Leu Arg Pro Ser Tyr Val Leu Ser Gly Ser Ala Met Asn Val Val
            1130                 1135                 1140 ttc tct gag gat gag atg aaa aaa ttc cta gaa gag gcg act aga    3594
Phe Ser Glu Asp Glu Met Lys Lys Phe Leu Glu Glu Ala Thr Arg
            1145                 1150                 1155 gtt tct cag gag cac cca gtg gtc ctg aca aaa ttt gtt gaa ggg    3639
Val Ser Gln Glu His Pro Val Val Leu Thr Lys Phe Val Glu Gly
            1160                 1165                 1170 gcc cga gaa gta gaa atg gac gct gtt ggc aaa gat gga agg gtt    3684
Ala Arg Glu Val Glu Met Asp Ala Val Gly Lys Asp Gly Arg Val
            1175                 1180                 1185 atc tct cat gcc atc tct gaa cat gtt gaa gat gca ggt gtc cac    3729
Ile Ser His Ala Ile Ser Glu His Val Glu Asp Ala Gly Val His
            1190                 1195                 1200 tcg gga gat gcc act ctg atg ctg ccc aca caa acc atc agc caa    3774
Ser Gly Asp Ala Thr Leu Met Leu Pro Thr Gln Thr Ile Ser Gln
            1205                 1210                 1215 ggg gcc att gaa aag gtg aag gat gct acc cgg aag att gca aag    3819
Gly Ala Ile Glu Lys Val Lys Asp Ala Thr Arg Lys Ile Ala Lys
            1220                 1225                 1230 gct ttt gcc atc tct ggt cca ttc aac gtc caa ttt ctt gtc aaa    3864
Ala Phe Ala Ile Ser Gly Pro Phe Asn Val Gln Phe Leu Val Lys
            1235                 1240                 1245 gga aat gat gtc ttg gtg att gag tgt aac ttg aga gct tct cga    3909
Gly Asn Asp Val Leu Val Ile Glu Cys Asn Leu Arg Ala Ser Arg
            1250                 1255                 1260 tcc ttc ccc ttt gtt tcc aag act ctt ggg gtt gac ttc att gat    3954
Ser Phe Pro Phe Val Ser Lys Thr Leu Gly Val Asp Phe Ile Asp
            1265                 1270                 1275 gtg gcc acc aag gtg atg att gga gag aat gtt gat gag aaa cat    3999
Val Ala Thr Lys Val Met Ile Gly Glu Asn Val Asp Glu Lys His
            1280                 1285                 1290 ctt cca aca ttg gac cat ccc ata att cct gct gac tat gtt gca    4044
Leu Pro Thr Leu Asp His Pro Ile Ile Pro Ala Asp Tyr Val Ala
            1295                 1300                 1305 att aag gct ccc atg ttt tcc tgg ccc cgg ttg agg gat gct gac    4089
Ile Lys Ala Pro Met Phe Ser Trp Pro Arg Leu Arg Asp Ala Asp
            1310                 1315                 1320 ccc att ctg aga tgt gag atg gct tcc act gga gag gtg gct tgc    4134
Pro Ile Leu Arg Cys Glu Met Ala Ser Thr Gly Glu Val Ala Cys
            1325                 1330                 1335 ttt ggt gaa ggt att cat aca gcc ttc cta aag gca atg ctt tcc    4179
Phe Gly Glu Gly Ile His Thr Ala Phe Leu Lys Ala Met Leu Ser
            1340                 1345                 1350 aca gga ttt aag ata ccc cag aaa ggc atc ctg ata ggc atc cag    4224
Thr Gly Phe Lys Ile Pro Gln Lys Gly Ile Leu Ile Gly Ile Gln
            1355                 1360                 1365 caa tca ttc cgg cca aga ttc ctt ggt gtg gct gaa caa tta cac    4269
Gln Ser Phe Arg Pro Arg Phe Leu Gly Val Ala Glu Gln Leu His
            1370                 1375                 1380 aat gaa ggt ttc aag ctg ttt gcc acg gaa gcc aca tca gac tgg    4314
Asn Glu Gly Phe Lys Leu Phe Ala Thr Glu Ala Thr Ser Asp Trp
            1385                 1390                 1395 ctc aac gcc aac aat gtc cct gcc aac cca gtg gca tgg ccg tct    4359
Leu Asn Ala Asn Asn Val Pro Ala Asn Pro Val Ala Trp Pro Ser
            1400                 1405                 1410 caa gaa gga cag aat ccc agc ctc tct tcc atc aga aaa ttg att    4404
```

| | | | | | | | | | | | |
|---|---|---|---|---|---|---|---|---|---|---|---|
| Gln | Glu | Gly | Gln | Asn | Pro | Ser | Leu | Ser | Ser | Ile | Arg | Lys | Leu | Ile |
| | | 1415 | | | | | 1420 | | | | | 1425 | | |

```
aga gat ggc agc att gac cta gtg att aac ctt ccc aac aac aac      4449
Arg Asp Gly Ser Ile Asp Leu Val Ile Asn Leu Pro Asn Asn Asn
        1430                1435                1440 act aaa ttt gtc cat gat aat tat gtg att cgg agg aca gct gtt      4494
Thr Lys Phe Val His Asp Asn Tyr Val Ile Arg Arg Thr Ala Val
        1445                1450                1455 gat agt gga atc cct ctc ctc act aat ttt cag gtg acc aaa ctt      4539
Asp Ser Gly Ile Pro Leu Leu Thr Asn Phe Gln Val Thr Lys Leu
        1460                1465                1470 ttt gct gaa gct gtg cag aaa tct cgc aag gtg gac tcc aag agt      4584
Phe Ala Glu Ala Val Gln Lys Ser Arg Lys Val Asp Ser Lys Ser
        1475                1480                1485 ctt ttc cac tac agg cag tac agt gct gga aaa gca gca tag          4626
Leu Phe His Tyr Arg Gln Tyr Ser Ala Gly Lys Ala Ala
        1490                1495                1500 agatgcagac accccagccc cattattaaa tcaacctgag ccacatgtta tctaaaggaa   4686
ctgattcaca actttctcag agatgaatat tgataactaa acttcatttc agtttacttt   4746
gttatgcctt aatattctgt gtcttttgca attaaattgt cagtcacttc ttcaaaacct   4806
tacagtcctt cctaagttac tcttcatgag atttcatcca tttactaata ctgtattttt   4866
ggtggactag gcttgcctat gtgcttatgt gtagcttttt acttttatg gtgctgatta    4926 atggtgatca aggtaggaaa agttgctgtt ctatttctg aactctttct atactttaag    4986
atactctatt tttaaaacac tatctgcaaa ctcaggacac tttaacaggg cagaatactc   5046
taaaaacttg ataaaatgaa atatagattt aatttatgaa ccttccatca tgatgtttgt   5106
gtattgcttc tttttggatc ctcattctca cccatttggc taatccagga atattgttat   5166
cccttcccat tatattgaag ttgagaaatg tgacagaggc atttagagta tggacttttc   5226
ttttcttttt cttttcttt ttttcttttt gagatggagt cacactctcc aggctggagt    5286
gcagtggcac aatctcggct cactgcaatt tgcgtctccc aagttcaagc gattctcctg   5346
ctttagacta tggatttctt taaggaatac tggtttgcag ttttgttttc tggactatat   5406
cagcagatgg tagacagtgt ttatgtagat gtgttgttgt ttttatcatt ggattttaac   5466
ttggcccgag tgaataatc agatttttgt cattcacact ctcccccagt tttggaataa    5526
cttggaagta aggttcattc ccttaagacg atggattctg ttgaactatg ggtcccaca    5586 ctgcactatt aattccaccc actgtaaggg caaggacacc attccttcta catataagaa   5646
aaaagtctct ccccaagggc agcctttgtt acttttaaat attttctgtt attacaagtg   5706
ctctaattgt gaacttttaa ataaaatact attaagaggt aaaaaaaaaa aaaaa        5761
```

<210> SEQ ID NO 14
<211> LENGTH: 1500
<212> TYPE: PRT
<213> ORGANISM: Homo sapiens

<400> SEQUENCE: 14

```
Met Thr Arg Ile Ile Thr Ala Phe Lys Val Val Arg Thr Leu Lys Thr
1               5                   10                  15

Gly Phe Gly Phe Thr Asn Val Thr Ala His Gln Lys Trp Lys Phe Ser
            20                  25                  30

Arg Pro Gly Ile Arg Leu Leu Ser Val Lys Ala Gln Thr Ala His Ile
        35                  40                  45

Val Leu Glu Asp Gly Thr Lys Met Lys Gly Tyr Ser Phe Gly His Pro
```

```
            50                  55                  60
Ser Ser Val Ala Gly Glu Val Phe Asn Thr Gly Leu Gly Gly Tyr
 65                  70                  75                  80

Pro Glu Ala Ile Thr Asp Pro Ala Tyr Lys Gly Gln Ile Leu Thr Met
                 85                  90                  95

Ala Asn Pro Ile Ile Gly Asn Gly Gly Ala Pro Asp Thr Thr Ala Leu
                100                 105                 110

Asp Glu Leu Gly Leu Ser Lys Tyr Leu Glu Ser Asn Gly Ile Lys Val
                115                 120                 125

Ser Gly Leu Leu Val Leu Asp Tyr Ser Lys Asp Tyr Asn His Trp Leu
130                 135                 140

Ala Thr Lys Ser Leu Gly Gln Trp Leu Gln Glu Lys Val Pro Ala
145                 150                 155                 160

Ile Tyr Gly Val Asp Thr Arg Met Leu Thr Lys Ile Ile Arg Asp Lys
                165                 170                 175

Gly Thr Met Leu Gly Lys Ile Glu Phe Glu Gly Gln Pro Val Asp Phe
                180                 185                 190

Val Asp Pro Asn Lys Gln Asn Leu Ile Ala Glu Val Ser Thr Lys Asp
                195                 200                 205

Val Lys Val Tyr Gly Lys Gly Asn Pro Thr Lys Val Val Ala Val Asp
210                 215                 220

Cys Gly Ile Lys Asn Asn Val Ile Arg Leu Leu Val Lys Arg Gly Ala
225                 230                 235                 240

Glu Val His Leu Val Pro Trp Asn His Asp Phe Thr Lys Met Glu Tyr
                245                 250                 255

Asp Gly Ile Leu Ile Ala Gly Gly Pro Gly Asn Pro Ala Leu Ala Glu
                260                 265                 270

Pro Leu Ile Gln Asn Val Arg Lys Ile Leu Glu Ser Asp Arg Lys Glu
                275                 280                 285

Pro Leu Phe Gly Ile Ser Thr Gly Asn Leu Ile Thr Gly Leu Ala Ala
                290                 295                 300

Gly Ala Lys Thr Tyr Lys Met Ser Met Ala Asn Arg Gly Gln Asn Gln
305                 310                 315                 320

Pro Val Leu Asn Ile Thr Asn Lys Gln Ala Phe Ile Thr Ala Gln Asn
                325                 330                 335

His Gly Tyr Ala Leu Asp Asn Thr Leu Pro Ala Gly Trp Lys Pro Leu
                340                 345                 350

Phe Val Asn Val Asn Asp Gln Thr Asn Glu Gly Ile Met His Glu Ser
                355                 360                 365

Lys Pro Phe Phe Ala Val Gln Phe His Pro Glu Val Thr Pro Gly Pro
                370                 375                 380

Ile Asp Thr Glu Tyr Leu Phe Asp Ser Phe Ser Leu Ile Lys Lys
385                 390                 395                 400

Gly Lys Ala Thr Thr Ile Thr Ser Val Leu Pro Lys Pro Ala Leu Val
                405                 410                 415

Ala Ser Arg Val Glu Val Ser Lys Val Leu Ile Leu Gly Ser Gly Gly
                420                 425                 430

Leu Ser Ile Gly Gln Ala Gly Glu Phe Asp Tyr Ser Gly Ser Gln Ala
                435                 440                 445

Val Lys Ala Met Lys Glu Glu Asn Val Lys Thr Val Leu Met Asn Pro
                450                 455                 460

Asn Ile Ala Ser Val Gln Thr Asn Glu Val Gly Leu Lys Gln Ala Asp
465                 470                 475                 480
```

-continued

```
Thr Val Tyr Phe Leu Pro Ile Thr Pro Gln Phe Val Thr Glu Val Ile
                485                 490                 495
Lys Ala Glu Gln Pro Asp Gly Leu Ile Leu Gly Met Gly Gly Gln Thr
                500                 505                 510
Ala Leu Asn Cys Gly Val Glu Leu Phe Lys Arg Gly Val Leu Lys Glu
            515                 520                 525
Tyr Gly Val Lys Val Leu Gly Thr Ser Val Glu Ser Ile Met Ala Thr
        530                 535                 540
Glu Asp Arg Gln Leu Phe Ser Asp Lys Leu Asn Glu Ile Asn Glu Lys
545                 550                 555                 560
Ile Ala Pro Ser Phe Ala Val Glu Ser Ile Glu Asp Ala Leu Lys Ala
                565                 570                 575
Ala Asp Thr Ile Gly Tyr Pro Val Met Ile Arg Ser Ala Tyr Ala Leu
                580                 585                 590
Gly Gly Leu Gly Ser Gly Ile Cys Pro Asn Arg Glu Thr Leu Met Asp
            595                 600                 605
Leu Ser Thr Lys Ala Phe Ala Met Thr Asn Gln Ile Leu Val Glu Lys
        610                 615                 620
Ser Val Thr Gly Trp Lys Glu Ile Glu Tyr Glu Val Val Arg Asp Ala
625                 630                 635                 640
Asp Asp Asn Cys Val Thr Val Cys Asn Met Glu Asn Val Asp Ala Met
                645                 650                 655
Gly Val His Thr Gly Asp Ser Val Val Ala Pro Ala Gln Thr Leu
                660                 665                 670
Ser Asn Ala Glu Phe Gln Met Leu Arg Arg Thr Ser Ile Asn Val Val
            675                 680                 685
Arg His Leu Gly Ile Val Gly Glu Cys Asn Ile Gln Phe Ala Leu His
        690                 695                 700
Pro Thr Ser Met Glu Tyr Cys Ile Ile Glu Val Asn Ala Arg Leu Ser
705                 710                 715                 720
Arg Ser Ser Ala Leu Ala Ser Lys Ala Thr Gly Tyr Pro Leu Ala Phe
                725                 730                 735
Ile Ala Ala Lys Ile Ala Leu Gly Ile Pro Leu Pro Glu Ile Lys Asn
                740                 745                 750
Val Val Ser Gly Lys Thr Ser Ala Cys Phe Glu Pro Ser Leu Asp Tyr
            755                 760                 765
Met Val Thr Lys Ile Pro Arg Trp Asp Leu Asp Arg Phe His Gly Thr
        770                 775                 780
Ser Ser Arg Ile Gly Ser Ser Met Lys Ser Val Gly Glu Val Met Ala
785                 790                 795                 800
Ile Gly Arg Thr Phe Glu Glu Ser Phe Gln Lys Ala Leu Arg Met Cys
                805                 810                 815
His Pro Ser Ile Glu Gly Phe Thr Pro Arg Leu Pro Met Asn Lys Glu
                820                 825                 830
Trp Pro Ser Asn Leu Asp Leu Arg Lys Glu Leu Ser Glu Pro Ser Ser
            835                 840                 845
Thr Arg Ile Tyr Ala Ile Ala Lys Ala Ile Asp Asp Asn Met Ser Leu
        850                 855                 860
Asp Glu Ile Glu Lys Leu Thr Tyr Ile Asp Lys Trp Phe Leu Tyr Lys
865                 870                 875                 880
Met Arg Asp Ile Leu Asn Met Glu Lys Thr Leu Lys Gly Leu Asn Ser
                885                 890                 895
```

-continued

```
Glu Ser Met Thr Glu Glu Thr Leu Lys Arg Ala Lys Glu Ile Gly Phe
        900                 905                 910

Ser Asp Lys Gln Ile Ser Lys Cys Leu Gly Leu Thr Glu Ala Gln Thr
        915                 920                 925

Arg Glu Leu Arg Leu Lys Lys Asn Ile His Pro Trp Val Lys Gln Ile
        930                 935                 940

Asp Thr Leu Ala Ala Glu Tyr Pro Ser Val Thr Asn Tyr Leu Tyr Val
945                 950                 955                 960

Thr Tyr Asn Gly Gln Glu His Asp Val Asn Phe Asp Asp His Gly Met
                965                 970                 975

Met Val Leu Gly Cys Gly Pro Tyr His Ile Gly Ser Ser Val Glu Phe
            980                 985                 990

Asp Trp Cys Ala Val Ser Ser Ile Arg Thr Leu Arg Gln Leu Gly Lys
        995                 1000                1005

Lys Thr Val Val Val Asn Cys Asn Pro Glu Thr Val Ser Thr Asp
    1010                1015                1020

Phe Asp Glu Cys Asp Lys Leu Tyr Phe Glu Glu Leu Ser Leu Glu
    1025                1030                1035

Arg Ile Leu Asp Ile Tyr His Gln Glu Ala Cys Gly Gly Cys Ile
    1040                1045                1050

Ile Ser Val Gly Gly Gln Ile Pro Asn Asn Leu Ala Val Pro Leu
    1055                1060                1065

Tyr Lys Asn Gly Val Lys Ile Met Gly Thr Ser Pro Leu Gln Ile
    1070                1075                1080

Asp Arg Ala Glu Asp Arg Ser Ile Phe Ser Ala Val Leu Asp Glu
    1085                1090                1095

Leu Lys Val Ala Gln Ala Pro Trp Lys Ala Val Asn Thr Leu Asn
    1100                1105                1110

Glu Ala Leu Glu Phe Ala Lys Ser Val Asp Tyr Pro Cys Leu Leu
    1115                1120                1125

Arg Pro Ser Tyr Val Leu Ser Gly Ser Ala Met Asn Val Val Phe
    1130                1135                1140

Ser Glu Asp Glu Met Lys Lys Phe Leu Glu Glu Ala Thr Arg Val
    1145                1150                1155

Ser Gln Glu His Pro Val Val Leu Thr Lys Phe Val Glu Gly Ala
    1160                1165                1170

Arg Glu Val Glu Met Asp Ala Val Gly Lys Asp Gly Arg Val Ile
    1175                1180                1185

Ser His Ala Ile Ser Glu His Val Glu Asp Ala Gly Val His Ser
    1190                1195                1200

Gly Asp Ala Thr Leu Met Leu Pro Thr Gln Thr Ile Ser Gln Gly
    1205                1210                1215

Ala Ile Glu Lys Val Lys Asp Ala Thr Arg Lys Ile Ala Lys Ala
    1220                1225                1230

Phe Ala Ile Ser Gly Pro Phe Asn Val Gln Phe Leu Val Lys Gly
    1235                1240                1245

Asn Asp Val Leu Val Ile Glu Cys Asn Leu Arg Ala Ser Arg Ser
    1250                1255                1260

Phe Pro Phe Val Ser Lys Thr Leu Gly Val Asp Phe Ile Asp Val
    1265                1270                1275

Ala Thr Lys Val Met Ile Gly Glu Asn Val Asp Glu Lys His Leu
    1280                1285                1290

Pro Thr Leu Asp His Pro Ile Ile Pro Ala Asp Tyr Val Ala Ile
```

-continued

|      |      |      |      |      |      |      |      |      |      |      |      |
|------|------|------|------|------|------|------|------|------|------|------|------|
|      | 1295 |      |      | 1300 |      |      | 1305 |      |      |      |      |

Lys Ala Pro Met Phe Ser Trp Pro Arg Leu Arg Asp Ala Asp Pro
    1310                     1315                   1320

Ile Leu Arg Cys Glu Met Ala Ser Thr Gly Glu Val Ala Cys Phe
    1325                     1330                   1335

Gly Glu Gly Ile His Thr Ala Phe Leu Lys Ala Met Leu Ser Thr
    1340                     1345                   1350

Gly Phe Lys Ile Pro Gln Lys Gly Ile Leu Ile Gly Ile Gln Gln
    1355                     1360                   1365

Ser Phe Arg Pro Arg Phe Leu Gly Val Ala Glu Gln Leu His Asn
    1370                     1375                   1380

Glu Gly Phe Lys Leu Phe Ala Thr Glu Ala Thr Ser Asp Trp Leu
    1385                     1390                   1395

Asn Ala Asn Asn Val Pro Ala Asn Pro Val Ala Trp Pro Ser Gln
    1400                     1405                   1410

Glu Gly Gln Asn Pro Ser Leu Ser Ser Ile Arg Lys Leu Ile Arg
    1415                     1420                   1425

Asp Gly Ser Ile Asp Leu Val Ile Asn Leu Pro Asn Asn Asn Thr
    1430                     1435                   1440

Lys Phe Val His Asp Asn Tyr Val Ile Arg Arg Thr Ala Val Asp
    1445                     1450                   1455

Ser Gly Ile Pro Leu Leu Thr Asn Phe Gln Val Thr Lys Leu Phe
    1460                     1465                   1470

Ala Glu Ala Val Gln Lys Ser Arg Lys Val Asp Ser Lys Ser Leu
    1475                     1480                   1485

Phe His Tyr Arg Gln Tyr Ser Ala Gly Lys Ala Ala
    1490                     1495                   1500

<210> SEQ ID NO 15
<211> LENGTH: 20
<212> TYPE: DNA
<213> ORGANISM: Homo sapiens

<400> SEQUENCE: 15
cggaagccac atcagactgg                                              20

<210> SEQ ID NO 16
<211> LENGTH: 24
<212> TYPE: DNA
<213> ORGANISM: Homo sapiens

<400> SEQUENCE: 16
ggagagtgaa acttgacaat catc                                         24

<210> SEQ ID NO 17
<211> LENGTH: 19
<212> TYPE: DNA
<213> ORGANISM: Homo sapiens

<400> SEQUENCE: 17
tactgctcag aatcatggc                                               19

<210> SEQ ID NO 18
<211> LENGTH: 19
<212> TYPE: DNA
<213> ORGANISM: Homo sapiens

<400> SEQUENCE: 18

```
tcatcaccaa ctgaacagg                                             19

<210> SEQ ID NO 19
<211> LENGTH: 21
<212> TYPE: DNA
<213> ORGANISM: Homo sapiens

<400> SEQUENCE: 19
ggttaagaga aggaggagct g                                          21

<210> SEQ ID NO 20
<211> LENGTH: 21
<212> TYPE: DNA
<213> ORGANISM: Homo sapiens

<400> SEQUENCE: 20
aaccagtctt cagtgtcctc a                                          21

<210> SEQ ID NO 21
<211> LENGTH: 15
<212> TYPE: DNA
<213> ORGANISM: Homo sapiens

<400> SEQUENCE: 21
cctgccaccc cagtg                                                 15

<210> SEQ ID NO 22
<211> LENGTH: 15
<212> TYPE: DNA
<213> ORGANISM: Homo sapiens

<400> SEQUENCE: 22
cctgccaacc cagtg                                                 15

<210> SEQ ID NO 23
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: X is A or S
<220> FEATURE:
<221> NAME/KEY: MISC_FEATURE
<222> LOCATION: (6)..(6)
<223> OTHER INFORMATION: X is T or S
<220> FEATURE:
<221> NAME/KEY: MISC_FEATURE
<222> LOCATION: (7)..(7)
<223> OTHER INFORMATION: X is A or Q

<400> SEQUENCE: 23

Pro Val Xaa Trp Pro Xaa Xaa Glu
1               5
```